(12) United States Patent
Puranen et al.

(10) Patent No.: US 8,580,552 B2
(45) Date of Patent: Nov. 12, 2013

(54) METHOD FOR TREATING CELLULOSIC MATERIAL AND CBHII/CEL6A ENZYMES USEFUL THEREIN

(75) Inventors: Terhi Puranen, Nurmijarvi (FI); Sauli Toikka, Jarvenpaa (FI); Kim Langfelder, Darmstadt (DE); Jari Vehmaanpera, Klaukkala (FI)

(73) Assignee: Royal Oy, Rajamaki (FI)

( * ) Notice: Subject to any disclaimer, the term of this patent is extended or adjusted under 35 U.S.C. 154(b) by 146 days.

(21) Appl. No.: 12/930,189

(22) Filed: Dec. 30, 2010

(65) Prior Publication Data
US 2011/0159544 A1 Jun. 30, 2011

Related U.S. Application Data

(60) Provisional application No. 61/335,063, filed on Dec. 30, 2009.

(51) Int. Cl.
| | |
|---|---|
| *C12N 9/42* | (2006.01) |
| *C12N 9/24* | (2006.01) |
| *C12N 1/00* | (2006.01) |
| *C12N 1/20* | (2006.01) |
| *C12P 21/04* | (2006.01) |
| *C12P 7/06* | (2006.01) |
| *C12P 7/10* | (2006.01) |
| *C12P 19/12* | (2006.01) |
| *C07H 21/04* | (2006.01) |
| *C11D 3/00* | (2006.01) |
| *C02F 3/34* | (2006.01) |
| *D06M 16/00* | (2006.01) |

(52) U.S. Cl.
USPC .......... 435/209; 435/100; 435/69.7; 435/165; 435/200; 435/252.3; 435/254.21; 435/262; 435/263; 435/161; 510/392; 536/23.2

(58) Field of Classification Search
None
See application file for complete search history.

(56) References Cited

U.S. PATENT DOCUMENTS

2006/0218671 A1* 9/2006 Brown et al. ................. 800/284

FOREIGN PATENT DOCUMENTS

| WO | WO2004/056981 | 7/2004 |
| WO | WO2006/074435 | 7/2006 |
| WO | WO2007/071818 | 6/2007 |
| WO | WO2009/085859 | 7/2009 |

OTHER PUBLICATIONS

UniProt Accession No. O93837, (Cellobiohydrolase II, created May 1, 1999.*
Voutilainen, S. P. et al., "Cloning, Expression, and Characterization of Novel Thermostable Family 7 Cellobiohydrolases", *Biotechnology and Bioengineering*, 101 (3):515-528 (2008).
Partial International Search Report in International Application No. PCT/EP2010/070927 dated Apr. 20, 2011, 3 pages.

* cited by examiner

*Primary Examiner* — Anand Desai
*Assistant Examiner* — Iqbal H Chowdhury
(74) *Attorney, Agent, or Firm* — Fish & Richardson P.C.

(57) ABSTRACT

The present invention relates to the production of sugar hydrolysates from cellulosic material. The method may be used, for example for producing fermentable sugars for the production of bioethanol from lignocellulosic material. Cellulolytic enzymes and their production by recombinant technology are described, as well as uses of the enzymes and enzyme preparations.

55 Claims, 7 Drawing Sheets

METHOD FOR TREATING CELLULOSIC MATERIAL AND CBHII/CEL6A ENZYMES USEFUL THEREIN

FIELD OF THE INVENTION

The present invention relates to a method for treating cellulosic material with a fungal CBHII/Cel6A cellobiohydrolase enzyme or an enzyme preparation comprising said enzyme. The enzyme is useful in various industrial applications, particularly in production of biofuels, where production of fermentable sugars from lignocellulosic material at moderate to elevated temperature ranges is advantageous. The invention further relates to fungal CBHII/Cel6A polypeptides and isolated nucleic acid molecules encoding said enzymes, a recombinant vector, host cells for producing said enzymes, enzyme compositions comprising said enzymes as well as a process for preparing such compositions. The invention relates also to various uses of said enzymes or enzyme compositions, in which enzymatic conversion of cellulosic or lignocellulosic material is desired.

BACKGROUND OF THE INVENTION

Limited resources of fossil fuels and increasing amounts of $CO_2$ released from them and causing the greenhouse phenomenon have raised a need for using biomass as a renewable and clean source of energy. One promising, alternative technology is the production of biofuels, such as ethanol, butanol or propanol from cellulosic materials. In the transportation sector biofuels are for the time being the only option, which could reduce the $CO_2$ emissions by an order of magnitude. The ethanol can be used in existing vehicles and distribution systems and thus it does not require expensive infrastructure investments. Sugars derived from cellulosic and lignocellulosic renewable raw materials can also be used as raw materials for a variety of chemical products that can replace oil-based chemicals.

Most of the carbohydrates in plants are in the form of lignocellulose, which essentially consists of cellulose, hemicellulose and lignin. In a conventional lignocellulose-to-ethanol process the lignocellulosic material is first pretreated either chemically or physically, using acid hydrolysis, steam explosion, ammonia fiber expansion, alkaline wet oxidation or ozone pretreatment, to make the cellulose fraction more accessible to enzymatic hydrolysis. The cellulose fraction is then hydrolyzed to obtain sugars that can be fermented by yeast into ethanol and distilled to obtain pure ethanol. Lignin is obtained as a main co-product that may be used as a solid fuel. In this separate hydrolysis and fermentation (SHF) process the temperature of enzymatic hydrolysis is typically higher than that of fermentation. The use of thermostable enzymes in hydrolysis offer potential benefits, such as higher reaction rates at elevated temperatures, reduction of enzyme load due to higher specific activity and life-time of enzymes, increased flexibility with respect to process configuration and better hygiene.

There is continuous research for making the bioethanol production process more economical. One of the options is the simultaneous saccharification and fermentation (SSF) process. The principal benefits are the reduced end-product inhibition of the enzymatic hydrolysis and the reduced investment costs. The challenges are in finding favorable conditions, e.g. temperature and pH, for both the enzymatic hydrolysis and fermentation. In the consolidated bioprocess (CBP), the amount of externally added enzymes can be significantly reduced by exploiting a fermentative organism or ethanolgen, which is capable of producing a set of lignocellulolytic enzymes.

In recent years, metabolic engineering for microorganisms used in ethanol production has shown significant progress. Besides *Saccharomyces cerevisiae*, microorganisms such as the bacterial species *Zymomonas* and *Escherichia coli* and yeasts such as *Pichia stipitis* and *Kluyveromyces fragilis* have been targeted for ethanol production from cellulose. In the SSF process, the inhibitor and temperature tolerance as well as the ability to utilize multiple sugars are important properties of the fermenting microorganism. Engineered yeasts have been developed that are able to ferment pentose sugars xylose and arabinose in addition to glucose. Thermophilic microbes, like *Thermoanaerobacterium saccharolyticum* or *Clostridium thermocellum* have been engineered to ferment sugars, including xylose, to ethanol at elevated temperatures of 50° C.-60° C. (thermophilic SSF or TSSF). Such fermentative organisms have also potential as CBPs (Shaw et al. 2008).

Enzymatic hydrolysis is considered the most promising technology for converting cellulosic biomass into fermentable sugars. However, enzymatic hydrolysis is used only to a limited amount at industrial scale, and especially when using strongly lignified material such as wood or agricultural waste the technology is not satisfactory. Efforts have been made to improve the efficiency of the enzymatic hydrolysis of the cellulosic material (Badger 2002; Kurabi et al., 2005).

WO2001060752 (Forskningscenter Risø, DK) describes a continuous process for converting solid lignocellulosic biomass into combustible fuel products. After pretreatment by wet oxidation or steam explosion the biomass is partially separated into cellulose, hemicellulose and lignin, and is then subjected to partial hydrolysis using one or more carbohydrase enzymes (EC 3.2).

WO2002024882 (Iogen Bio-Products Corp., CA) pertains a method of converting cellulose to glucose by treating a pretreated lignocellulosic substrate with an enzyme mixture comprising cellulase and a modified cellobiohydrolase I (CBHI) obtained by inactivating its cellulose binding domain (CBD). US2004/0005674 (Athenix Corp., US) describes novel enzyme mixtures that can be used directly on lignocellulose substrate. The synergistic enzyme mixture contains a cellulase and an auxiliary enzyme such as cellulase, xylanase, ligninase, amylase, protease, lipidase or glucuronidase, or any combination thereof. Cellulase is considered to include endoglucanase (EG), beta-glucosidase (BG) and cellobiohydrolase (CBH) enzymes.

US20050164355 (Novozymes Biotech Inc., US) describes a method for degrading lignocellulosic material with one or more cellulolytic enzymes selected from EG, BG and CBH and in the presence of at least one surfactant. Additional enzymes such as hemicellulases, esterase, peroxidase, protease, laccase or mixture thereof may also be used.

The best-investigated and most widely applied cellulolytic enzymes of fungal origin have been derived from *Trichoderma reesei* (the anamorph of *Hypocrea jecorina*). Cellulases from less known fungi have also been disclosed.

Hong et al. (2003a and 2003b) characterize EG and CBHI of *Thermoascus aurantiacus* and their production in yeast. Tuohy et al. (2002) describe three forms of cellobiohydrolases, including CBHI and CBHII from *Talaromyces emersonii*.

Use of cellobiohydrolase I (CBHI), a member of family 7 of glycosyl hydrolases in enzymatic conversion of cellulosic material is known, for example from WO03/000941 (Novozymes A/S, DK), which relates to CBHI enzymes obtained from various fungi. WO2005074656 (Novozymes Inc., US) discloses polypeptides having cellulolytic activity derived e.g. from *Thermoascus aurantiacus*.

WO2007071818 (Roal Oy, FI) describes production of sugar hydrolysates from cellulosic material by enzymatic conversion and enzyme preparations comprising said enzymes. Enzymes useful in the method include thermostable cellobiohydrolase, endoglucanase, beta-glucosidase and optionally xylanase deriving from *Thermoascus aurantiacus, Acremonium thermophilum* or *Chaetomium thermophilum*.

Cellobiohydrolases II have been disclosed in several applications. WO2004056981 (Novozymes A/S, DK) discloses polypeptides having cellobiohydrolase II activity and polynucleotides encoding the polypeptides as well as methods for producing and using the polypeptides in applications, such as in production of ethanol. Full length DNA sequences are disclosed from *Aspergillus tubigensis, Chaetomium thermophilum, Myceliophtora thermophila*, species of *Thielavia, Acremonium thermophilum, Trichophaea saccata, Stibella anualata* and *Malbrancheae cinnamonea*. EP1578964 B1 (Novozymes A/S, DK) discloses the full length amino acid sequence of *C. thermophilum* CBHII and a polypeptide encoded by a nucleotide sequence hybridizing under stringent conditions with a fragment of the nucleotide sequence encoding said enzyme.

CN1757709 (Shandong Agricultural Univ., CN) discloses the nucleotide sequence of a thermophilic CBHII enzyme of *Chaetomium thermophilum* CT2 and its expression in *Pichia pastoris* yeast. The enzyme is capable of converting the rejected fiber material.

WO2006074005 (Genencor Int., Inc., US) discloses a variant of *Hypocrea jecorina* (*Trichoderma reesei*) CBHII/Cel6A enzyme. The variant enzyme is useful, for example in bioethanol production.

WO2007094852 (Diversa Corp., US; Verenium Corp., US) discloses cellulolytic enzymes, nucleic acids encoding them and methods for their production and use. The enzyme may be an endoglucanase, a cellobiohydrolase, a beta-glucosidase, a xylanase, a mannanase, a beta-xylosidase, an arabinofuranosidase or an oligomerase. The enzyme and enzyme mixtures are useful, for example in making fuel or bioethanol.

WO2008095033 (Syngenta, CH, Verenium Corp., US) discloses enzymes having lignocellulolytic activity, including cellobiohydrolases useful, for example in making fuels and processing biomass materials. WO2009045627 (Verenium Corp., US) discloses methods for breaking down hemicellulose by using enzymes having xylanase, mannanase and/or glucanase activity and increased activity and stability at increased pH and temperature.

WO2009089630 (Iogen Energy Corp., CA) discloses a variant of a family 6 cellulase with reduced inhibition by glucose, comprising one or more amino acid substitutions.

WO2009059234 (Novozymes Inc., US) discloses methods of producing cellulosic material reduced in a redox active metal ion useful in degrading or converting a cellulosic material and producing a fermentation product. The application discloses, e.g. a CBHII polypeptide of *Chaetomium thermophilum*.

WO2009085868 (Novozymes A/S, DK) discloses polypeptides, polynucleotides encoding the enzyme and a method for producing a fermentation product, comprising saccharification of a cellulosic material with a cellulolytic enzyme composition comprising said polypeptide. Such cellobiohydrolases may derive from *Trichoderma reesei, Humicola insolens, Myceliophtora thermophila, Thielavia terrestris* and *Chaetomium thermophilum*.

WO2006074435 and US2006218671 (Novozymes Inc., US) disclose nucleotide and amino acid sequences of *Thielavia terrestris* Cel6A cellobiohydrolase. U.S. Pat. No. 7,220,565 (Novozymes Inc., US) discloses polypeptides having cellulolytic enhancing activity and identity to the mature amino acid sequence of *Myceliophtora thermophila* CBHII.

US20070238155 and US20090280105 (Dyadic Int., Inc., US) disclose enzyme compositions comprising novel enzymes from *Chrysosporium lucknowense*, comprising e.g. the CBHIIa and CBHIIb enzymes assigned to family 6 of glycosyl hydrolases. The enzyme compositions are effective in hydrolysis of the lignocellulosic material.

The genome sequence of *Neurospora crassa* OR74A is disclosed in Galagan et al. (2003), including a sequence of exoglucanase 2 precursor. Collins et al. (2003) disclose the coding sequence of *Talaromyces emersonii* CBHII/Cel6A.

The market in biofuels such as renewable transportation fuels is expected to increase considerably in near future. As a result, there is a rapidly growing interest in the use of alternative feedstock for biofuel production. Fermentation of cellulosic biomass present in plants and woods or municipal waste to ethanol and other alcohols is an attractive route to fuels that supplement fossil fuels. One barrier of production of biofuels from cellulosic and lignocellulosic biomass is the robustness of the cell walls and the presence of sugar monomers in the form of inaccessible polymers that require a great amount of processing to make the sugar monomers available to the microorganisms that are typically used to produce alcohol by fermentation. Thus, there is a continuous need for new methods as well as new enzymes and enzyme mixtures, which enhance the efficiency of the degradation of the cellulosic and lignocellulosic substrates. Particularly, enzymes and enzyme mixtures are needed which are able to attack different glycosidic linkages of the crystalline cellulosic material and thus provide almost complete hydrolysis of the varying materials to be treated. There is also a need for enzymes, which are stable at elevated process temperatures, thus enabling the use of high biomass consistency and leading to high sugar and ethanol concentrations. This approach may lead to significant savings in energy and investments costs. The high temperature also decreases the risk of contamination during hydrolysis. The present invention aims to meet at least part of these needs.

SUMMARY OF THE INVENTION

The aim of the present invention is to provide new enzymes and enzyme compositions for enhancing the efficiency of cellulose hydrolysis. The cellobiohydrolases and particularly cellobiohydrolases II obtainable from *Acremonium thermophilum, Melanocarpus albomyces, Chaetomium thermophilum* or *Talaromyces emersonii* are useful in hydrolyzing and degrading cellulosic material. The enzymes are kinetically very effective over a broad range of temperatures, and although they have high activity at high temperatures, they are also very efficient at standard hydrolysis temperatures. This makes them extremely well suited for varying cellulosic substrate hydrolysis processes carried out both at conventional temperatures and at elevated temperatures.

The present invention relates to a method for treating cellulosic material with a CBHII/Cel6A polypeptide or an enzyme preparation comprising said polypeptide or a fermentative microorganism producing said polypeptide, said method comprising the steps: i) production of a CBHII/Cel6A polypeptide of the invention or an enzyme preparation comprising said polypeptide or a fermentative microorganism producing said polypeptide; ii) reacting the cellulosic material with the CBHII/Cel6A polypeptide of the invention or the enzyme preparation comprising said polypeptide or the fermentative microorganism producing said polypeptide; and iii) obtaining partially or fully hydrolyzed cellulosic material. The CBHII/Cel6A polypeptide useful in said method has cellobiohydrolase activity and comprises an amino acid sequence having at least 76% identity to the full-length polypeptide of SEQ ID NO: 12, at least 76% identity to the full-length polypeptide of SEQ ID NO:14, at least 95% identity to the full-length polypeptide of SEQ ID NO:15, or at least 91% identity to the full-length polypeptide of SEQ ID NO:16. The CBHII/Cel6A polypeptide may also be a fragment or variant having similar properties, such as similar substrate specificity and pH and temperature dependence or stability. The CBHII/Cel6A cellobiohydrolase useful in the method is a cellobiohydrolase II enzyme of family 6 of glycosyl hydrolases and has both a conserved fold and stereochemistry of the hydrolysis reaction.

The CBHII/Cel6A cellobiohydrolases applicable in the method may be obtained from a genus of *Acremonium, Melanocarpus, Chaetomium* or *Talaromyces*, more preferably from *A. thermophilum, M. albomyces, C. thermophilum* or *T. emersonii*, most preferably from the deposited strain *A. thermophilum* CBS 116240, *M. albomyces* CBS 685.95, *C. thermophilum* CBS 730.95 or *T. emersonii* DSM 2432.

The CBHII/Cel6A cellobiohydrolase applicable in the method is capable of hydrolyzing different cellulosic materials at moderate to elevated temperatures, particularly in combination with other enzymes used in hydrolysis of various cellulosic or lignocellulosic materials.

The CBHII/Cel6A cellobiohydrolase of the invention is applicable in various uses, particularly in production of biofuel.

The present invention relates also to novel CBHII/Cel6A cellobiohydrolases, which have cellobiohydrolase activity and comprise an amino acid sequence having at least 76% identity to the full-length polypeptide of SEQ ID NO: 12, at least 76% identity to the full-length polypeptide of SEQ ID NO: 14, at least 95% identity to the full-length polypeptide of SEQ ID NO:15 or at least 91% identity to the full-length polypeptide of SEQ ID NO:16. Said CBHII/Cel6A polypeptide may also be a fragment or variant having similar properties, such as similar substrate specificity and pH and temperature dependence or stability. Said CBHII/Cel6A cellobiohydrolase is capable of hydrolyzing cellulosic material at moderate to elevated temperatures.

Said enzyme is encoded by an isolated nucleic acid molecule, which comprises a polynucleotide sequence encoding a polypeptide of the invention. Preferably, said nucleic acid molecule comprises the polynucleotide sequence defined in SEQ ID NO: 11, SEQ ID NO:13, SEQ ID NO:9 or SEQ ID NO:10 or a subsequence thereof.

The CBHII/Cel6A cellobiohydrolase of the invention may be encoded by an isolated nucleic acid molecule, which hybridizes under stringent conditions to a polynucleotide sequence included in SEQ ID NO:11, SEQ ID NO:13, SEQ ID NO:9, SEQ ID NO:10, SEQ ID NO:7, SEQ ID NO:8 or a subsequence thereof.

Said enzyme is encoded by an isolated polynucleotide included in plasmid pALK2582 deposited in *Escherichia coli* under accession number DSM 22946, plasmid pALK2581 deposited in *E. coli* under accession number DSM 22945, plasmid pALK2904 deposited in *E. coli* under accession number DSM 22947 or plasmid pALK3006 deposited in *E. coli* under accession number DSM 23185

The CBHII/Cel6A cellobiohydrolase of the invention may be produced from a recombinant expression vector comprising the nucleic acid molecule or nucleotide sequence encoding said cellobiohydrolase. Said cellobiohydrolase polypeptide may be produced in a heterologous host, preferably in a microbial host.

The invention relates also to an isolated nucleic acid molecule comprising a polynucleotide sequence encoding a fungal CBHII/Cel6A polypeptide selected from the group consisting of:

(a) a nucleic acid molecule or polynucleotide sequence encoding a polypeptide having cellobiohydrolase activity and comprising the full-length amino acid sequence as depicted in SEQ ID NO:12, SEQ ID NO:14, SEQ ID NO:15 or SEQ ID NO:16, or a fragment or variant thereof having similar properties;

(b) a nucleic acid molecule or polynucleotide sequence encoding a polypeptide having cellobiohydrolase activity and at least 76% identity to the full-length amino acid sequence of SEQ ID NO:12, at least 76% identity to the full-length amino acid sequence of SEQ ID NO:14, at least 95% identity to the full-length amino acid sequence of SEQ ID NO:15 or at least 91% identity to the full-length amino acid sequence of SEQ ID NO:16, or a fragment or variant thereof having similar properties;

c) a nucleic acid molecule comprising the coding sequence of the polynucleotide sequence depicted as SEQ ID NO:11, SEQ ID NO:13, SEQ ID NO:9 or SEQ ID NO:10;

(d) a nucleic acid molecule comprising the coding sequence of the polynucleotide sequence contained in DSM 22946, DSM 22945, DSM 22947 or DSM 23185;

(e) a nucleic acid molecule the coding sequence of which differs from the coding sequence of a nucleic acid molecule of any one of (c) to (d) due to the degeneracy of the genetic code; and (f) a nucleic acid molecule hybridizing under stringent conditions to a nucleic acid molecule contained in DSM 22946, DSM 22945, DSM 22947 or DSM 23185, and encoding a polypeptide having cellobiohydrolase activity and an amino acid sequence which shows at least 76% identity to the full-length amino acid sequence as depicted in SEQ ID NO:12, at least 76% identity to the full-length amino acid sequence of SEQ ID NO:14, at least 95% identity to the full-length amino acid sequence of SEQ ID NO:15 or at least 91% identity to the full-length amino acid sequence of SEQ ID NO:16, or a fragment or variant thereof having similar properties.

The invention further relates to a recombinant expression vector comprising the nucleic acid molecule or polynucleotide sequence of the invention operably linked to regulatory sequences capable of directing expression of the gene encoding the CBHII/Cel6A cellobiohydrolase of the invention and production of said CBHII/Cel6A cellobiohydrolase in a suitable host.

The invention relates also to a host cell comprising the recombinant expression vector as described above. Preferably, the host is a microbial host, such as a filamentous fungal host. Preferred hosts are *Trichoderma, Aspergillus, Fusarium, Humicola, Chrysosporium, Neurospora, Rhizopus, Penicillium* and *Mortiriella*. More preferably the host is *Trichoderma* or *Aspergillus*, most preferably a filamentous fungus *T. reesei*.

The present invention relates to a process of producing a polypeptide of the invention having cellobiohydrolase activity, said process comprising the steps of culturing the host cell of the invention and recovering the polypeptide. Also within the invention is a polypeptide having cellobiohydrolase activity encoded by the nucleic acid molecule of the invention and which is obtainable by the process described above.

The invention relates also to a process for obtaining an enzyme preparation comprising the steps of culturing a host cell of the invention and preparing the whole culture broth, or separating the cells from the spent culture medium and obtaining the supernatant. Within the invention is also an enzyme preparation obtainable by the process described above. The invention relates also to an enzyme preparation, which comprises the CBHII/Cel6A cellobiohydrolase of the invention.

The enzyme preparation may further comprise other enzymes selected from the group: cellobiohydrolase, endoglucanase, beta-glucosidase, beta-glucanase, xyloglucanase, xylanase, beta-xylosidase, mannanase, beta-mannosidase, α-glucuronidase, acetyl xylan esterase, α-arabinofuranosidase, α-galactosidase, pectinase, involving endo- and exo-α-L-arabinases, α-galactosidase, endo- and exo-galactoronase, endopectinlyase, pectate lyase and pectinesterase, phenol esterase, ligninase involving lignin peroxidase, manganese-dependent peroxidase, $H_2O_2$-generating enzyme and laccase with or without a mediator.

The enzyme preparation may be in the form of whole culture broth or spent culture medium. It may be in the form of liquid, powder or granulate.

Also within the invention is the use of the CBHII/Cel6A polypeptide or enzyme preparation of the invention for production of biofuel, for detergents, for treating fibers, for treating food or feed, for pulp and paper, for beverage or for any applications involving hydrolysis or modification of cellulosic material.

Particularly, the CBHII/Cel6A polypeptide or enzyme composition comprising said polypeptide is useful for production of biofuel.

BRIEF DESCRIPTION OF DRAWINGS

FIG. 4 shows results from hydrolysis of steam exploded hardwood material performed with enzyme mixtures comprising the CBHII/Cel6A cellobiohydrolase of the invention. The hardwood substrate was hydrolyzed using different enzyme mixtures at a dosage of 5 mg of protein per g of total solids both at 55° C. and 37° C. The composition of the thermophilic enzyme mixture (MIXTURE 2) and the mesophilic enzyme mixtures (MIXTURE *T. REESEI* ENZYMES and MIXTURE ACC), comprising the At_ALKO4245Cel6A, Ma_ALKO4237_Cel6A or Ct_ALKO4265_Cel6A are described in more detail in Example 4. Samples from duplicated shake flasks were taken after a 72 hours hydrolysis time and quantified by HPLC, in which the concentration of glucose and xylose were determined. The results from the substrate blanks, containing buffer instead of the enzyme sample, were subtracted from the results obtained with the enzyme mixtures. The combined concentration of glucose and xylose is presented.

SEQUENCE LISTING

Figure 1:
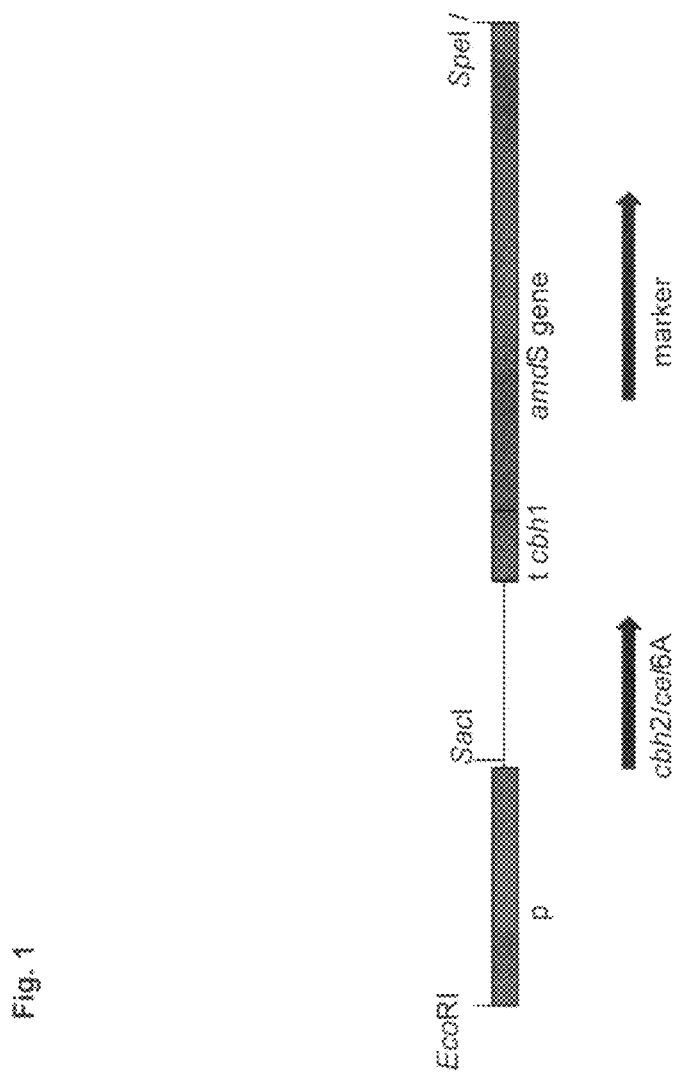
FIG. 1 schematically shows the expression cassettes used in the transformation of *Trichoderma reesei* protoplasts for overproducing the recombinant CBHII/Cel6A proteins. The cbh2/cel6A genes were under the control of *T. reesei* cbh1/cel7A promoter (p cbh1) and the termination of the transcription was ensured by using *T. reesei* cbh1/cel7A terminator sequence (t cbh1). The amdS gene was included as a transformation marker.

SEQ ID NO: 1 Sequence of the oligonucleotide primer CBH_1S

SEQ ID NO: 2 Sequence of the oligonucleotide primer CBH_1AS

SEQ ID NO: 3 Sequence of the oligonucleotide primer CBH_8

SEQ ID NO: 4 Sequence of the oligonucleotide primer CBH_9

SEQ ID NO: 5 Sequence of the oligonucleotide primer Te_CBH_A

SEQ ID NO: 6 Sequence of the oligonucleotide primer Te_CBH_B

SEQ ID NO: 7 Sequence of the PCR fragment obtained from *Acremonium thermophilum* ALKO4245 (CBS 116240) using the primers CBH_1S and CBH_1AS.

SEQ ID NO: 8 Sequence of the PCR fragment obtained from *Melanocarpus albomyces* ALKO4237 (CBS 685.95) using the primers CBH_1S and CBH_1AS.

SEQ ID NO: 9 The nucleotide sequence of the *Chaetomium thermophilum* ALKO4265 (CBS 730.95) cbh2/cel6A gene.

SEQ ID NO: 10 The nucleotide sequence of the *Talaromyces emersonii* RF8069 (DSM 2432) cbh2/cel6A gene.

SEQ ID NO: 11 The nucleotide sequence of the *Acremonium thermophilum* ALKO4245 (CBS 116240) cbh2/cel6A gene.

SEQ ID NO: 12 The deduced amino acid sequence of the *Acremonium thermophilum* ALKO4245 (CBS 116240) CBHII/Cel6A.

SEQ ID NO: 13 The nucleotide sequence of the *Melanocarpus albomyces* ALKO4237 (CBS 685.95) cbh2/cel6A gene.

SEQ ID NO: 14 The deduced amino acid sequence of the *Melanocarpus albomyces* ALKO4237 (CBS 685.95) CBHII/Cel6A.

SEQ ID NO: 15 The deduced amino acid sequence of the *Chaetomium thermophilum* ALKO4265 (CBS 730.95) CBHII/Cel6A.

SEQ ID NO: 16 The deduced amino acid sequence of the *Talaromyces emersonii* RF8069 (DSM 2432) CBHII/Cel6A.

DEPOSITIONS

*Acremonium thermophilum* ALKO4245 was deposited at the Centraalbureau Voor Schimmelcultures at Upsalalaan 8, 3584 CT, Utrecht, the Netherlands on 20 Sep. 2004 and assigned accession number CBS 116240.

*Chaetomium thermophilum* ALKO4265 was deposited at the Centraalbureau Voor Schimmelcultures at Oosterstraat 1, 3742 SK BAARN, the Netherlands on 8 Nov. 1995 and assigned accession number CBS 730.95. After termination of the current deposit period, samples will be stored under agreements as to make the strain available beyond the enforceable time of the patent.

*Melanocarpus albomyces* ALKO4237 was deposited at the Centraalbureau Voor Schimmelcultures at Oosterstraat 1, 3740 AG BAARN, the Netherlands on 11 Oct. 1995 and assigned accession number CBS 685.95. After termination of the current deposit period, samples will be stored under agreements as to make the strain available beyond the enforceable time of the patent.

The *Escherichia coli* strain RF8175 including the plasmid pALK2582 was deposited at the Deutsche Sammlung von Mikroorganismen and Zellkulturen GmbH (DSMZ), Inhoffenstrasse 7B, D-38124 Braunschweig, Germany on 9 Sep. 2009 and assigned accession number DSM 22946.

The *E. coli* strain RF8174 including the plasmid pALK2581 was deposited at the Deutsche Sammlung von Mikroorganismen und Zellkulturen GmbH (DSMZ), Inhoffenstrasse 7B, D-38124 Braunschweig, Germany on 9 Sep. 2009 and assigned accession number DSM 22945.

The *E. coli* strain RF8214 including the plasmid pALK2904 was deposited at the Deutsche Sammlung von Mikroorganismen und Zellkulturen GmbH (DSMZ), Inhoffenstrasse 7B, D-38124 Braunschweig, Germany on 9 Sep. 2009 and assigned accession number DSM 22947.

The *E. coli* strain RF8333 including the plasmid pALK3006 was deposited at the Deutsche Sammlung von Mikroorganismen und Zellkulturen GmbH (DSMZ), Inhoffenstrasse 7B, D-38124 Braunschweig, Germany on 10 Dec. 2009 and assigned accession number DSM 23185.

DETAILED DESCRIPTION OF THE INVENTION

The present invention provides a method for treating cellulosic material with a CBHII/Cel6A cellobiohydrolase polypeptide or an enzyme composition comprising said polypeptide. The invention provides also fungal CBHII/Cel6A cellobiohydrolase polypeptides and enzyme compositions comprising said CBHII/Cel6A polypeptides, which polypeptides show broad substrate specificity, and are stable at broad pH and temperature ranges. They have good performance both at moderate and elevated temperatures. Particularly, the CBHII/Cel6A cellobiohydrolase polypeptides are stable for at least 21 hours up to 70° C., preferably at a temperature range from 40° C. to 60° C. The polypeptides and enzyme compositions comprising said polypeptides are ideal in different applications requiring efficient hydrolysis of complex cellulosic or lignocellulosic materials, where cellulose is one of the major components. The polypeptides and enzyme compositions are useful, for example in hydrolysis of cellulosic material in order to produce sugar monomers from the polymeric starting material, which then can be fermented by microorganisms in the production of biofuel. Thus, the present invention provides alternative CBHII/Cel6A cellobiohydrolases for use in biofuel and other applications. The fungal CBHII/Cel6A cellobiohydrolases can be produced in high-yielding fungal hosts with or without down-stream processing, e.g. separation of fermentation broth and mycelia is easy to perform, or in fermentative organisms.

"Cellulose" or "cellulosic material" as used herein relates to any material comprising cellulose as a significant component. Cellulose is the major structural component of higher plants. It provides plant cells with high tensile strength helping them to resist mechanical stress and osmotic pressure. Cellulose is a β-1,4-glucan composed of linear chains of glucose residues joined by β-1,4-glycosidic linkages. Cellobiose is the smallest repeating unit of cellulose. Examples of cellulosic material include textile fibers derived e.g. from cotton, linen, hemp, jute and the manmade cellulosic fibers such as modal, viscose, lyocel.

The term "cellulose" or "cellulosic material" refers also to "lignocellulose" or "lignocellulosic material" comprising cellulose as a significant component.

In cell walls cellulose is packed in variously oriented sheets, which are embedded in a matrix of hemicellulose, pectin and/or polymers of phenol propanol units such as lignin to form "lignocellulosic material" or "lignocellulose". Lignocellulose is physically hard, dense, and inaccessible. Lignocellulose containing materials include, e.g. plant materials such as wood, including hardwood and softwood, hardwood and softwoods chips, wood pulp, sawdust and forestry and wood industrial waste; herbaceous crops, agricultural biomass as cereal straws, sugar beet pulp, corn fiber, corn stover and cobs, cereal beta-glucans, sugar cane bagasse, stems, leaves, hulls, husks, and the like; waste products as municipal solid waste, newspaper and waste office paper, waste fiber, paper sludge, milling waste of e.g. grains; dedicated energy crops (e.g., willow, poplar, switchgrass or reed canarygrass, and the like).

Cellulosic and lignocellulosic material is degraded in nature by a number of various organisms including bacteria and fungi which produce enzymes capable of hydrolyzing carbohydrate polymers. Degradation usually requires the action of many enzymes which typically act sequentially or simultaneously. The biological conversion of cellulose to glucose generally requires three major types of hydrolytic enzymes: (1) Endoglucanases (EG) which cut internal beta-1,4-glycosidic bonds mainly in the amorphous regions of cellulose; (2) Exoglucanases or cellobiohydrolases (CBH) that cut the dissaccharide cellobiose from the reducing or non-reducing end of the crystalline cellulose polymer chain; (3) Beta-1,4-glucosidases (BG) which hydrolyze the cellobiose and other short cello-oligosaccharides to glucose. Glucose and cellobiose act as end-product inhibitors of the hydrolysis reaction.

"Cellulase" or "cellulolytic enzyme" is an enzyme having "cellulase activity" or "cellulolytic activity", which means that it is capable of hydrolyzing cellulosic material. One of the most studied cellulolytic enzyme systems is that of the filamentous fungus *Trichoderma reesei* which is known to exhibit at least 2 CBHs, 8 EGs and 5 BGs.

"Lignocellulolytic enzymes" are enzymes having "lignocellulase activity" or "lignocellulolytic activity", which means that they are capable of hydrolyzing lignocellulosic material, such as celluloses, hemicelluloses, or derivatives thereof into smaller saccharides.

The "beta-glucans" are mixed-linkage (1→3),(1→4)-beta-D-glucans. They are common in, e.g., cereals.

"Beta-glucanase" as used herein refers to enzymes that can cleave at least partly the linkages in beta-glucan.

"Cellobiohydrolase" or "CBH" as used herein refers to enzymes that cleave the 1,4-beta-D-glucosidic linkages of polymers such as cellulose from the reducing or non-reducing end and produce mainly cellobiose. They are also called exoglucanases or 1,4-beta-D-glucan cellobiohydrolases or cellulose 1,4-beta-cellobiosidases. CBHs have a modular structure consisting of distinct domains, such as a catalytic domain and an N- or C-terminal cellulose-binding domain (CBD). There are also cellobiohydrolases in nature which lack CBD. CBHs may also have additional domains of unknown function. Different domains are usually joined together by an O-glycosylated linker or hinge peptide rich in glycine, proline, serine or threonine.

By "cellobiohydrolase II" or "CBHII cellobiohydrolase" or "CBHII/Cel6A cellobiohydrolase" or "CBHII/Cel6A cellulase" or "CBHII/Cel6A polypeptide" or "CBHII/Cel6A enzyme" is in connection of this invention meant an 1,4-β-D-glucan cellobiohydrolase enzyme classified as EC 3.2.1.91 by the Nomenclature of the International Union of Biochemistry and Molecular Biology (IUBMB). Based on their structural similarities, cellobiohydrolases II or CBHII/Cel6A cellobiohydrolases of the present invention are classified into family 6 of glycosyl hydrolases (GH6) having similar amino acid sequences and three-dimensional structures (Henrissat 1991; Henrissat and Bairoch 1993, 1996; Henrissat et al. 1998). Because there is a direct relationship between sequence and folding similarities, such a classification is believed to reflect the structural features of the enzymes better than their sole substrate specificity, help to reveal the evolutionary relationships between the enzymes, and provide a convenient tool to derive mechanistic information.

By the term "cellobiohydrolase activity" or "CBH activity" as used in the invention is meant hydrolytic activity acting on 1,4-beta-D-glycosidic linkages in cellulose, cellotriose, cellotetraose or in any beta-1,4-linked glucose polymer releasing primarily cellobiose from the reducing or non-reducing end of the polymeric chain. The enzymatic break-down of a glycosidic bond is a stereoselective process, in which the configuration about the anomeric center (C1 carbon) can either be inverted or retained. Both mechanisms contain a pair of carboxylic acid residues disposed on either side of the bond to be cleaved. Inverting enzymes use a single-displacement mechanism, whereas the retaining enzymes involve a double-displacement reaction (Sinnott, 1990; Withers and Aebersold, 1995). The stereo chemical course of the hydrolysis is usually determined by proton NMR, in which the α- and β-anomeric protons give different chemical shifts (Withers et al., 1986).

By the term "cellobiohydrolase II activity" or "CBHII/Cel6A activity" as used in the invention is meant hydrolytic activity acting on 1,4-beta-D-glycosidic linkages in cellulose, cellotriose, cellotetraose or in any beta-1,4-linked glucose polymer releasing primarily cellobiose from the non-reducing end of the polymeric chain. The reaction mechanism of CBHII/Cel6A cellobiohydrolases is inverting.

The methods for analyzing cellulase activity are well-known in the literature and are referred, e.g. by Ghose (1987), Tomme et al. (1988) and van Tilbeurgh et al. (1988). Overall cellulase activity is commonly measured as filter paper-degrading activity (FPU). Cellobiohydrolase activity may be analyzed using small, soluble cellodextrins and their chromogenic glycosides, such as 4-methylumbelliferyl-beta-D-glycosides. CBHII/Cel6A cellobiohydrolases can be identified based on the outcome of the hydrolysis reaction; CBHII/Cel6A enzymes cannot cleave the heterosidic linkage of small chromogenic oligosaccharides (van Tilbeurgh et al., 1988). Cellobiohydrolase activity can be analyzed also on microcrystalline cellulose such as Avicel Ph 101, as used in Example 3. The formation of soluble reducing sugars after hydrolysis may be determined by para-hydroxybenzoic-acidhydrazide (PAHBAH) method (Lever, 1972) using a cellobiose standard curve, the Somogyi-Nelson method (Somogyi, 1952), alkaline ferricyanide method (Robyt and Whelan, 1972), the 2,2'-bichinconinate method (Waffenschmidt and Jaenicke, 1987) or the dinitrosalisylic acid (DNS) method of Miller (1959). Other cellulosic substrates include, e.g. Solka floc cellulose or phosphoric acid swollen cellulose (Karlsson et al., 2001).

Cellobiohydrolase II can be identified also in a Western or ELISA assay using polyclonal or monoclonal antibodies raised against the purified CBHII/Cel6A protein.

The term "CBHII/Cel6A cellobiohydrolase" thus means cellobiohydrolase II enzymes which are members of family 6 of glycosyl hydrolases, having both a conserved fold and stereochemistry of the hydrolysis reaction.

The term "moderate temperature" or "conventional temperature" in context of the present invention means temperatures commonly used in cellulose hydrolysis and corresponding to the optimal temperatures or thermal stabilities of the enzymes used in such processes. Thus, the terms refer to temperature ranges from 30° C. to 45° C.

The term "elevated temperature" or "high temperature" refers to temperature ranges from 45° C. to 70° C. In short term hydrolysis processes the enzymes may be effective even up to 80° C. Enzymes active or stable at such elevated temperature ranges are also called "thermostable" or "thermophilic" enzymes.

Microorganism strains capable of producing CBHII/Cel6A cellobiohydrolase polypeptide or CBHII/Cel6A cellobiohydrolase activity can be screened on different substrates. First the chosen strains are cultivated on a suitable medium. After a sufficient amount of an interesting cellobiohydrolase has been produced, the enzyme can be isolated or purified and its properties can be more thoroughly characterized. Alternatively, genes encoding cellobiohydrolases or CBHII/Cel6A cellobiohydrolases in various organisms can be isolated and the amino acid sequence encoded by the genes can be compared with the amino acid sequences of the CBHII/Cel6A cellobiohydrolases isolated and characterized in Example 1.

The produced cellobiohydrolase enzymes, particularly the CBHII/Cel6A cellobiohydrolase enzymes can be purified by using conventional methods of enzyme chemistry, such as salt preparation, ultrafiltration, ion exchange chromatography, affinity chromatography, gel filtration and hydrophobic interaction chromatography. Purification can be monitored by protein determination, enzyme activity assays and by SDS polyacrylamide gel electrophoresis. The enzyme activity and stability of the purified enzyme at various temperature and pH values as well as the molecular mass and the isoelectric point can be determined. Alternatively, the properties of CBHII/Cel6A cellobiohydrolases of the invention may be identified by producing the enzymes in a recombinant host, and purifying and characterizing the recombinant CBHII/Cel6A cellobiohydrolases enzyme. Also, the properties of the recombinant enzyme preparation comprising the CBHII/Cel6A cellobiohydrolase of the invention as one of the major enzyme components may be characterized as described in Example 3.

The molecular mass of the purified CBHII/Cel6A cellobiohydrolase can be determined by mass spectrometry or on SDS-PAGE according to Laemmli (1970). The molecular mass can also be predicted from the amino acid sequence of the enzyme using the pI/MW tool at ExPASy server (http://expasy.org/tools/pi_tool.html; Gasteiger et al., 2003).

The temperature dependency or thermostability of the CBHII/Cel6A cellobiohydrolase enzyme can be determined in a suitable buffer at different temperatures by using e.g. Avicel cellulose as a substrate as described in Example 3 or by using other substrates and buffer systems described in the literature. Determination of the pH dependency and pH stability can be carried out in a suitable buffer at different pH values by following the activity on a cellulosic substrate.

pI can be determined by isoelectric focusing on an immobilized pH gradient gel composed of polyacrylamide, starch or agarose or by estimating the pI from the amino acid sequence, for example by using the pI/MW tool at ExPASy server (http://expasy.org/tools/pi_tool.html; Gasteiger et al., 2003).

The N-terminus of the purified recombinant CBHII/Cel6A enzyme as well as internal peptides can be sequenced according to Edman degradation chemistry (Edman and Begg, 1967) or by predicting the cleavage site of the secretion signal sequence from the amino acid sequence, e.g. by using the program SignalP V3.0 (Nielsen et al., 1997; Nielsen and Krogh, 1998; Bendtsen et al., 2004) as described in Example 1 or other methods described in the literature.

The term "full-length" means the form of enzyme translated from the coding DNA sequence, beginning with the ATG start codon, which encodes the first methionine in the amino acid sequence and ending at the TGA, TAG or TAA stop codon.

The term "mature" means the form of enzyme which after removal of the signal sequence (secretion signal peptide or prepeptide) comprises the essential amino acids for enzymatic or catalytic activity. In filamentous fungi it is the form secreted into the culture medium as a result, for example of N-terminal processing of the signal sequence and other N-terminal processing, and post-translational glycosylation. In addition, the mature form means an enzyme which has been cleaved from its carrier protein in fusion constructions.

Many of the bacterial and fungal cellobiohydrolases are produced as modular enzymes (Srisodsuk et al., 1993; Suurnäkki et al., 2000). In addition to a catalytic or core domain expressing cellulolytic activity these enzymes may comprise one or more cellulose binding domains (CBDs), also named as carbohydrate binding domains/modules (CBD/CBM), which can be located either at the N- or C-terminus of the catalytic domain. CBDs have carbohydrate-binding activity and they mediate the binding of the cellulase enzyme to crystalline cellulose but have little or no effect on cellulase hydrolytic activity of the enzyme on soluble substrates. These two domains are typically connected via a flexible and highly glycosylated linker or hinge region as is evident from the amino acid sequences of SEQ ID NO:12, SEQ ID NO:14, SEQ ID NO:15 and SEQ ID NO:16.

"Fragment" as used in the invention means a polypeptide lacking one or more amino acid residues from the N- and/or C-terminus of the full-length polypeptide of SEQ ID NO:12, SEQ ID NO:14, SEQ ID NO:15 or SEQ ID NO:16, such as the mature form of the polypeptide or other enzymatically active portion of the polypeptide. The fragment still has the essential catalytic activity or cellobiohydrolase activity of the full-length CBHII/Cel6A cellobiohydrolase and substantially similar properties such as pH and temperature dependence and stability and substrate specificity. The polypeptides of the invention disclosed in SEQ ID NO: 12, SEQ ID NO:14, SEQ ID:15 and SEQ ID NO:16 naturally contain a N-terminal CBD and a linker. These native linker or CBD regions may be replaced by, e.g. a CBD from a *Trichoderma* or *Chaetomium* species. The CBHII/Cel6A enzymes of the invention may be used in the applications also without a signal sequence and/or CBD or the signal sequence and/or CBD may derive from different enzymes of the above microorganisms or different microorganism or be synthetically or recombinantly incorporated to the catalytic domain of the above enzymes.

The term "identity" as used herein means the identity between two amino acid sequences compared to each other within the corresponding sequence region having approximately the same amount of amino acids. For example, the identity of a full-length or a mature sequence of the two amino acid sequences may be compared. Also, the identity of a full-length or a mature sequence lacking the N-terminal CBD of the two amino acid sequences may be compared. Thus, comparison of e.g. the CBHII/Cel6A sequences including CBD and/or signal sequences with sequences lacking those elements is not within the context of the invention. The identity of the full-length sequences may be measured by using, for example ClustalW alignment (e.g. in www.ebi.ac.uk/Tools/Clustalw) with a matrix as follows: BLOSUM, Gap open:10, Gap extension: 0.5, or using a program of Clone Manager (version 9) (Scientific and Educational Software, Cary, USA), including the functions "Compare Two Sequences/Global/Compare sequences as amino acids/BLOSUM62 scoring matrix as described in Example 1.

The amino acid sequences of the two molecules to be compared may differ in one or more positions, which however do not alter the biological function or structure of the molecules. Such "variants" may occur naturally because of different host organisms or mutations in the amino acid sequence, e.g. as an allelic variant within the same strain, species or genus, or they may be achieved by specific mutagenesis. They may comprise amino acid substitutions, deletions, combinations or insertions of one or more positions in the amino acid sequence, but they still function in a substantially similar manner to the enzymes defined in SEQ ID NO:12, SEQ ID NO:14, SEQ ID NO:15 or SEQ ID NO:16, i.e. they comprise a variant having cellulolytic activity.

The present invention relates to a method for treating cellulosic material, including also lignocellulosic material with a CBHII/Cel6A polypeptide or an enzyme composition comprising said polypeptide or as in a consolidated bioprocess, the cellulosic material may be treated with a fermentative microorganism producing said polypeptide, wherein the CBHII/Cel6A polypeptide exhibits cellobiohydrolase activity and comprises an amino acid sequence having at least 76% identity to the full-length polypeptide of SEQ ID NO: 12, at least 76% identity to the full-length polypeptide of SEQ ID NO:14, at least 95% identity to the full-length polypeptide of SEQ ID NO:15, or at least 91% identity to the full-length polypeptide of SEQ ID NO:16, or a fragment or variant thereof having similar properties. Said enzyme is capable in hydrolyzing cellulosic material, including lignocellulose at moderate to elevated temperatures. Said method comprises the following steps: i) production of a CBHII/Cel6A polypeptide of the invention or an enzyme composition comprising said polypeptide or a fermentative microorganism producing said polypeptide; ii) reacting the cellulosic material with the CBHII/Cel6A polypeptide of the invention or the enzyme composition comprising said polypeptide or the fermentative microorganism producing said polypeptide; and iii) obtaining partially or fully hydrolyzed cellulosic material, including hydrolyzed lignocellulosic material.

CBHII/Cel6A cellobiohydrolase enzymes useful for treating or hydrolyzing cellulosic material are "obtainable from" any organism including plants. Preferably CBHII/Cel6A enzymes originate from microorganisms, e.g. bacteria or fungi. The bacteria may be, for example from a genus selected from *Bacillus, Azospirillum, Streptomyces* and *Pseudomonas*.

More preferably the enzyme originates from fungi (including filamentous fungi and yeasts), for example from a genus selected from the group consisting of yeasts *Schizosaccharomyces, Kluyveromyces, Pichia, Saccharomyces, Candida* and *Yarrowia* or filamentous fungi *Achaetomium, Acremonium, Aspergillus, Aureobasidium, Botrytis, Chaetomium, Chrysosporium, Cryptococcus, Collybia, Fomes, Fusarium, Humicola, Hypocrea, Lentinus, Magnaporthea, Melanocarpus, Mucor, Myceliophthora, Myriococcum, Neocallimastix, Neurospora, Paecilomyces, Penicillium, Phanerochaete, Phlebia, Pleurotus, Podospora, Polyporus, Pycnoporus, Rhizoctonia, Schizophyllum, Scytalidium, Talaromyces, Thermoascus, Thielavia, Trametes* and *Trichoderma*. Preferably the CBHII/Cel6A enzymes derive from *Acremonium thermophilum, Melanocarpus albomyces, Chaetomium thermophilum* or *Talaromyces emersonii*.

According to a preferred embodiment of the invention the enzymes are obtainable from a filamentous fungal strain ALKO4245 deposited as CBS 116240 and presently classified as *Acremonium thermophilium, Melanocarpus albomyces* strain ALKO4237 deposited as CBS 685.95, *Talaromyces emersonii* strain DSM 2432 (in applicant's culture collection under the number RF8069) or *Chaetomium thermophilum* strain ALKO4265 deposited as CBS 730.95.

The CBHII/Cel6A cellobiohydrolases of the present invention are marked as At_ALKO4245_Cel6A, Ma_ALKO4237_Cel6A, Ct_ALKO4265_Cel6A and Te_RF8069_Cel6A, being the CBHII/Cel6A cellobiohydrolases originating from the strains *Acremonium thermophilum* CBS 116240, *Melanocarpus albomyces* CBS 685.95, *Chaetomium thermophilum* CBS 730.95 or *Talaromyces emersonii* DSM 2432 and members of family 6 of glycoside hydrolases.

TABLE 1

The CBHII/Cel6A cellobiohydrolases of the invention

| Cellobio-hydrolase II | Gene | Obtainable from | nucleic acid SEQ ID NO: | amino acid SEQ ID NO: |
|---|---|---|---|---|
| At_ALKO4245_Cel6A | At_ALKO4245_cel6A | *Acremonium thermophilum* | 11 | 12 |
| Ma_ALKO4237_Cel6A | Ma_ALKO4237_cel6A | *Melanocarpus albomyces* | 13 | 14 |
| Ct_ALKO4265_Cel6A | Ct_ALKO4265_cel6A | *Chaetomium thermophilum* | 9 | 15 |
| Te_RF8069_Cel6A | Te_RF8069_cel6A | *Talaromyces emersonii* | 10 | 16 |

According to a preferred embodiment of the invention the fungal CBHII/Cel6A cellobiohydrolase enzyme useful in the method is a polypeptide having cellobiohydrolase activity and comprising the enzyme of At_ALKO4245_Cel6A having the full-length amino acid sequence of SEQ ID NO: 12 or an amino acid sequence having at least 76% identity to the amino acid sequence SEQ ID NO: 12. Preferred enzymes show at least 78%, 80% or 82%, preferably at least 84%, 86% or 88%, more preferably at least 90%, even more preferably at least 92% identity. Still more preferably the amino acid sequences show at least 94% or at least 96% or 97%, more preferably at least 98%, most preferably 99% identity to the amino acid sequence of SEQ ID NO: 12. The identities of the two enzymes are compared within the corresponding sequence regions, i.e. within the full-length region of the CBHII/Cel6A cellobiohydrolase.

Another preferred embodiment of the invention is a fungal CBHII/Cel6A cellobiohydrolase enzyme useful in the method having cellobiohydrolase activity and comprising the enzyme of Ma_ALKO4237_Cel6A having the full-length amino acid sequence of SEQ ID NO:14 or an amino acid sequence having at least 76% identity to the amino acid sequence SEQ ID NO:14. Preferred enzymes show at least 78%, 80% or 82%, preferably at least 84%, 86% or 88%, more preferably at least 90%, even more preferably at least 92% identity. Still more preferably the amino acid sequences show at least 94% or at least 96% or 97%, more preferably at least 98%, most preferably 99% identity to the amino acid sequence of SEQ ID NO: 14. The identities of the two enzymes are compared within the corresponding sequence regions, i.e. within the full-length region of the CBHII/Cel6A cellobiohydrolase.

A further preferred embodiment of the invention is a fungal CBHII/Cel6A cellobiohydrolase enzyme useful in the method having cellobiohydrolase activity and comprising the enzyme of Ct_ALKO4265_Cel6A having the full-length amino acid sequence of SEQ ID NO:15 or an amino acid sequence having at least 95% identity to the amino acid sequence SEQ ID NO:15. Preferred enzymes show at least 96%, preferably at least 97%, more preferably at least 98%, most preferably at least 99% identity to the amino acid sequence of SEQ ID NO: 15. The identities of the two enzymes are compared within the corresponding sequence regions, i.e. within the full-length region of the CBHII/Cel6A cellobiohydrolase.

Still further preferred embodiment of the invention is a fungal CBHII/Cel6A cellobiohydrolase enzyme useful in the method having cellobiohydrolase activity and to comprising the enzyme of Te_RF8069_Cel6A having the full-length amino acid sequence of SEQ ID NO:16 or an amino acid sequence having at least 91% identity to the amino acid sequence SEQ ID NO:16. Preferred enzymes show at least 92%, more preferably at least 93%, even more preferably at least 94% identity. Still more preferably the amino acid sequences show at least 95% or at least 96% or 97%, more preferably at least 98%, most preferably 99% identity to the amino acid sequence of SEQ ID NO: 16. The identities of the two enzymes are compared within the corresponding sequence regions, i.e. within the full-length region of the CBHII/Cel6A cellobiohydrolase.

The fungal CBHII/Cel6A cellobiohydrolases of the invention are active or stable over a broad pH range of at least pH 3 to pH 10 and more preferably at a pH range of at least pH 3 to pH 7 when assayed at 50° C. for 21 hours using Avicel cellulose as a substrate, as described in Example 3.

In particular, the At_ALKO4245_Cel6A is active between pH 3 and pH 7, preferably between pH 4 and pH 6, and more preferably between pH 4 and pH 5. The maximum activity of At_ALKO4245_Cel6A is at pH 5 when assayed at 50° C. for 21 hours using Avicel cellulose as a substrate.

The Ma_ALKO4237_Cel6A is active at a pH range between pH 3 and pH 10, preferably between pH 4 and pH 8, more preferably between pH 4 and pH 7, still more preferably between pH 4 and pH 6, and even more preferably between pH 4 and pH 5. The maximum activity of Ma_ALKO4237_Cel6A is at pH 4 when assayed at 50° C. for 21 hours using Avicel cellulose as a substrate.

The Ct_ALKO4265_Cel6A is active at a pH range between pH 3 and pH 10, preferably between pH 3 and pH 8, more preferably between pH 3 and pH 7, still more preferably between pH 4 and pH 7, and even more preferably between pH 4 and pH 6. The maximum activity of Ct_ALKO4265_Cel6A is at pH 5 when assayed at 50° C. for 21 hours using Avicel cellulose as a substrate.

The Te_RF8089_Cel6A is active at a pH range between pH 3 and pH 7, preferably between pH 3 and pH 6, and more preferably between pH 4 and pH 6. The maximum activity of Te_RF8089_Cel6A is at pH 4 when assayed at 50° C. for 21 hours using Avicel cellulose as a substrate.

The enzymes of the invention are effective in degrading cellulosic or lignocellulosic material at a broad temperature range. The CBHII/Cel6A cellobiohydrolases of the invention are active or stable for up to 21 hours in a temperature range between 40° C. and 70° C. when assayed at the optimum pH of the enzymes using Avicel cellulose as a substrate, as described in Example 3.

The At_ALKO4245_Cel6A cellobiohydrolase is active between 40° C. and 70° C., preferably between 40° C. and 60° C., more preferably between 50° C. and 60° C. At optimal pH the maximum activity of At_ALKO4245_Cel6A is at 60° C. when using a 21 hours incubation time and Avicel cellulose as a substrate.

The Ma_ALKO4237_Cel6A cellobiohydrolase is active in a temperature range between 40° C. and 60° C. The enzyme shows maximum activity at 50° C. when incubated for 21 hours at the optimal pH using Avicel cellulose as a substrate. The Ct_ALKO4265_Cel6A cellobiohydrolase is active in a temperature range between 40° C. and 70° C., preferably in the range of 50° C. to 60° C. At the optimal pH the maximum activity is at 60° C. when using a 21 hours incubation time and Avicel cellulose as a substrate. The Te_RF8089_Cel6A cellobiohydrolase is active between 40° C. and 70° C., preferably between 40° C. and 60° C., more preferably between 50° C. and 60° C. The maximum activity is at 60° C. when incubated for 21 hours at the optimal pH using Avicel cellulose as a substrate.

The cellulolytic enzymes presently in use in hydrolysis of cellulosic material and production of fermentable sugars for, e.g. bioethanol applications derive mainly from the well-studied microorganisms, such as the filamentous fungus *Trichoderma reesei* (e.g. the Accellerase® product line, Genencor Int., Inc., US). The cellulolytic enzymes are conventionally used at temperatures in the range of 30° C. to 45° C. The CBHII/Cel6A cellobiohydrolases of the present invention are efficient at these temperatures too, but in addition they work extremely well even at temperatures up to 70° C., such as between 40° C. and 70° C., e.g. between 40° C. and 70° C. or between 40° C. and 60° C. or between 50° C. and 60° C., as shown in Example 3. For short hydrolysis times enzyme compositions may be functional up to 80° C. For total hydrolysis longer incubation times are required and, therefore, lower temperatures are normally used. This makes the CBHII/Cel6A cellobiohydrolases of the invention extremely well suited for varying cellulosic substrate hydrolysis processes carried out both at conventional or moderate temperatures and at elevated temperatures.

Figure 4A:
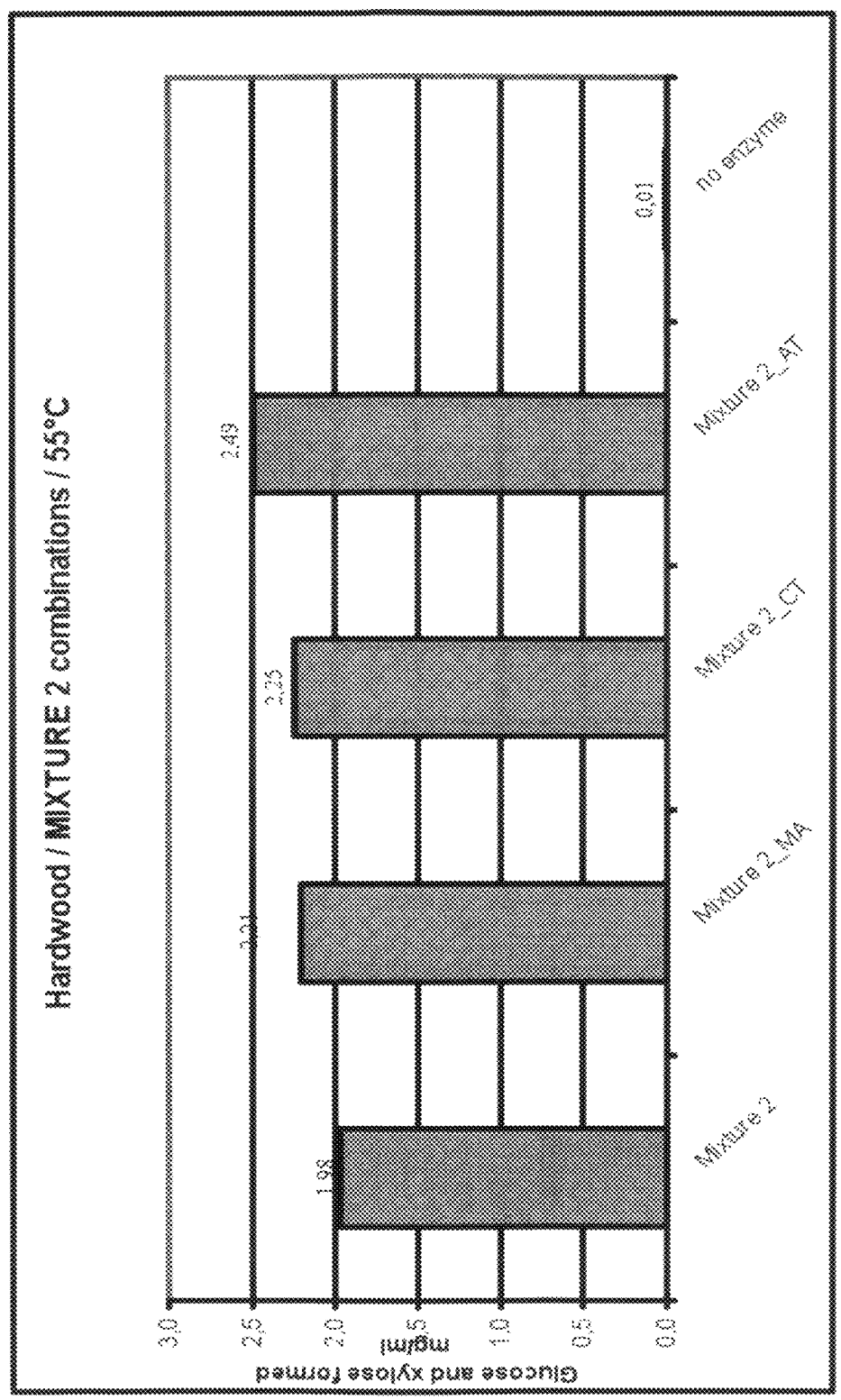
FIG. 4A shows the hydrolysis results of steam exploded hardwood performed at 55° C. with a thermophilic enzyme mixture (MIXTURE 2) supplemented with the At_ALKO4245_Cel6A (MIXTURE 2_AT), Ma_ALKO4237_Cel6A (MIXTURE 2_MA) or Ct_ALKO4265_Cel6A (MIXTURE 2_CT).
Figure 4B:
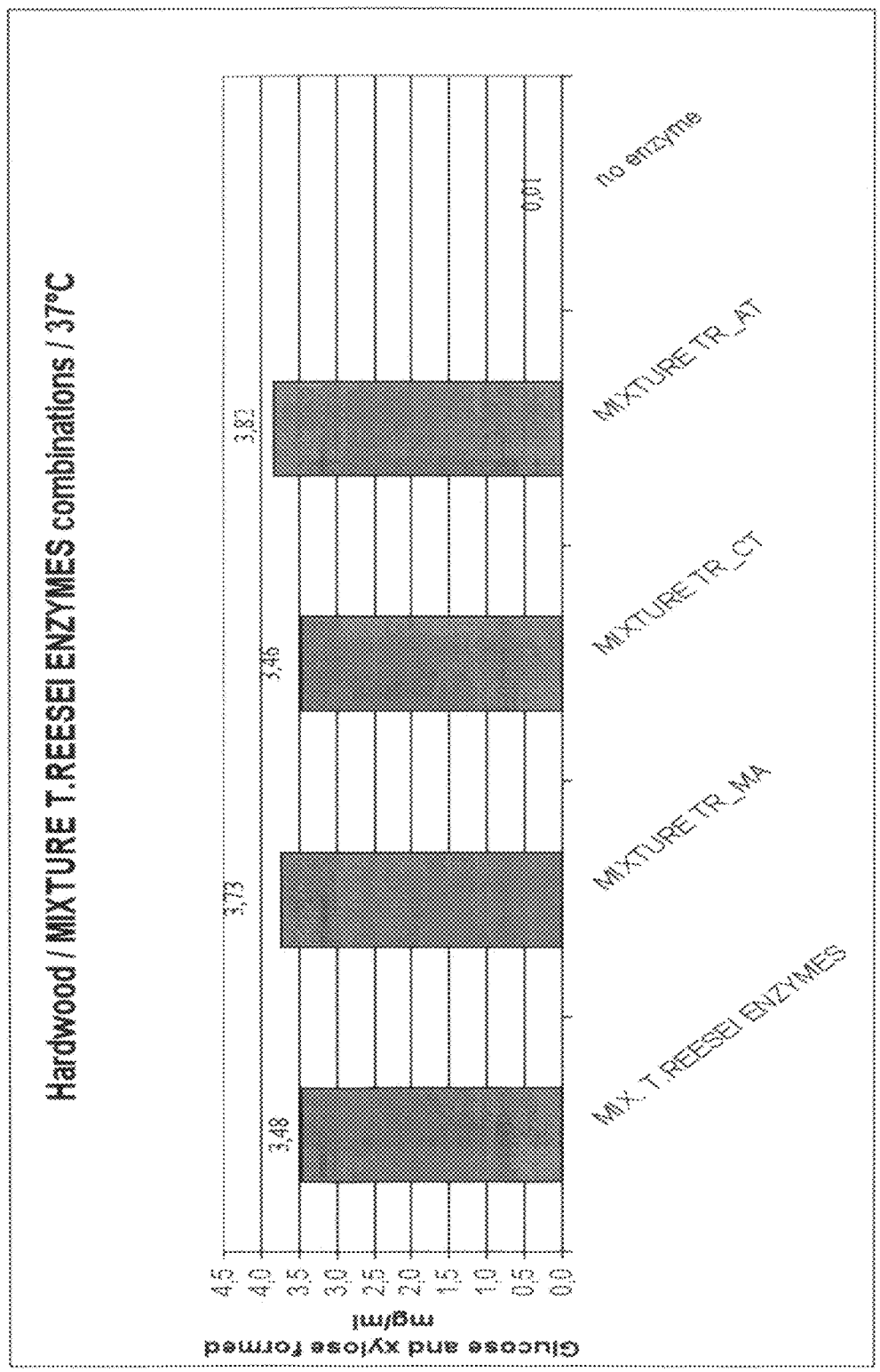
FIG. 4B shows the hydrolysis results of steam exploded hardwood performed at 37° C. with a mesophilic enzyme mixture (MIXTURE *T. REESEI* ENZYMES) supplemented with the At_ALKO4245_Cel6A (MIXTURE TR_AT), Ma_ALKO4237_Cel6A (MIXTURE TR_MA) or Ct_ALKO4265_Cel6A (MIXTURE TR_CT).
Figure 4C:
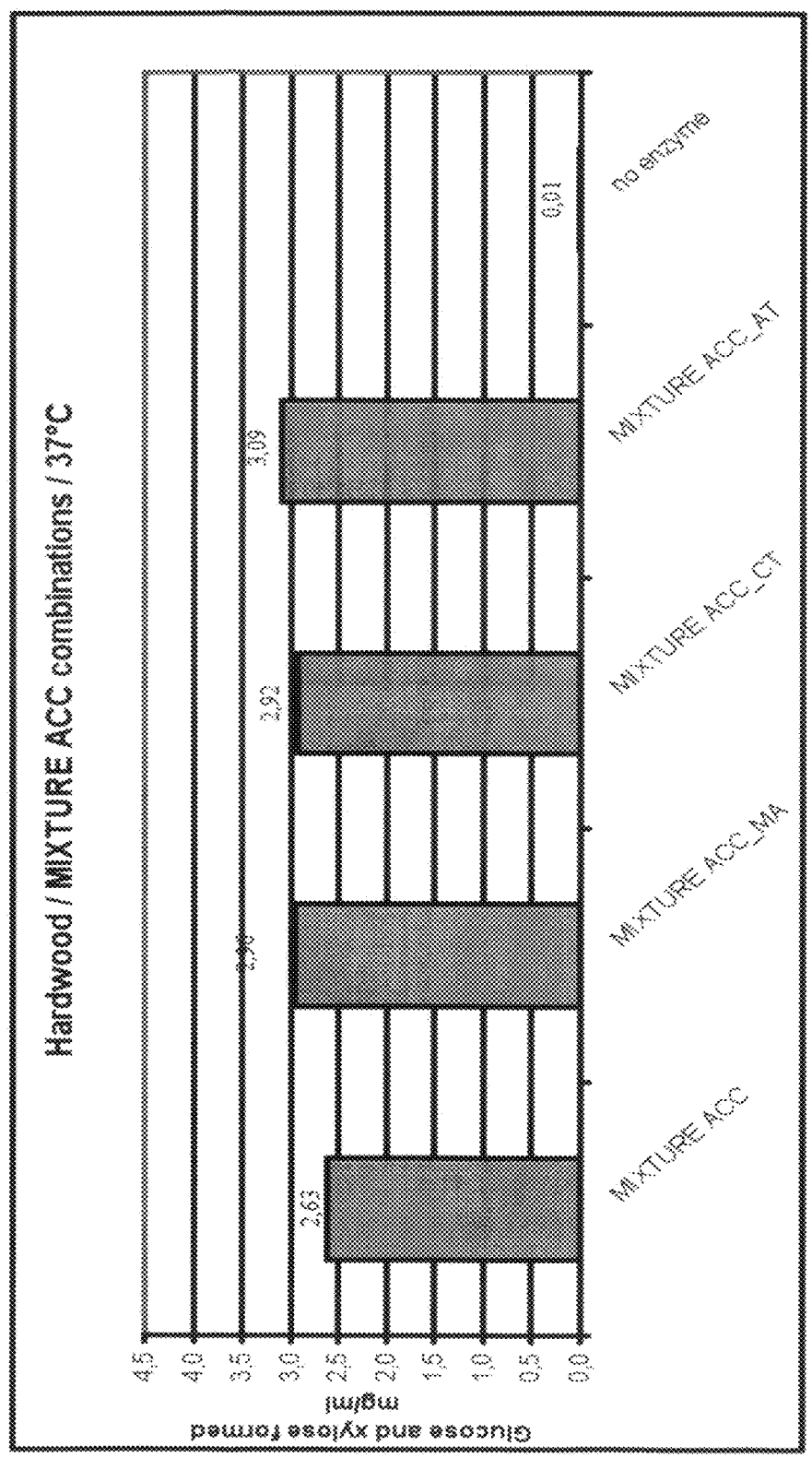
FIG. 4C shows the hydrolysis results of steam exploded hardwood performed at 37° C. with a mesophilic enzyme mixture (MIXTURE ACC) supplemented with the At_ALKO4245_Cel6A (MIXTURE ACC_AT), Ma_ALKO4237_Cel6A (MIXTURE ACC_MA) or Ct_ALKO4265_Cel6A (MIXTURE ACC_CT).

In Examples 4 and 5, experiments performed on various cellulosic materials, such as hardwood and corn cobs are described. From FIG. 4 it is evident that the performance of the enzyme mixtures supplemented with the fungal CBHII/Cel6A cellobiohydrolases At_ALKO4245_Cel6A, Ma_ALKO4237_Cel6A or Ct_ALKO4265_Cel6A in hydrolysis of steam exploded hardwood is by far better than the performance of the enzyme mixtures without such supplementation. In the experiments performed at 55° C. (FIG. 4A), the amount of sugars released from the hardwood substrate was found to increase 12%, 14% and 26% by supplementing with Ma_ALKO4237_Cel6A, Ct_ALKO4265_Cel6A or At_ALKO4245_Cel6A enzymes in the MIXTURE 2, respectively. *Acremonium thermophilum* ALKO4245 enzyme was found to be best-performing CBHII/Cel6A herein studied. At_ALKO4245_Cel6A shows increased hydrolysis also at 37° C. added either in the state-of-the-art *Trichoderma* mixture (MIXTURE *T. REESEI* ENZYMES) (FIG. 4B) or in the commercial product (MIXTURE ACC) (FIG. 4C).

Figure 5:
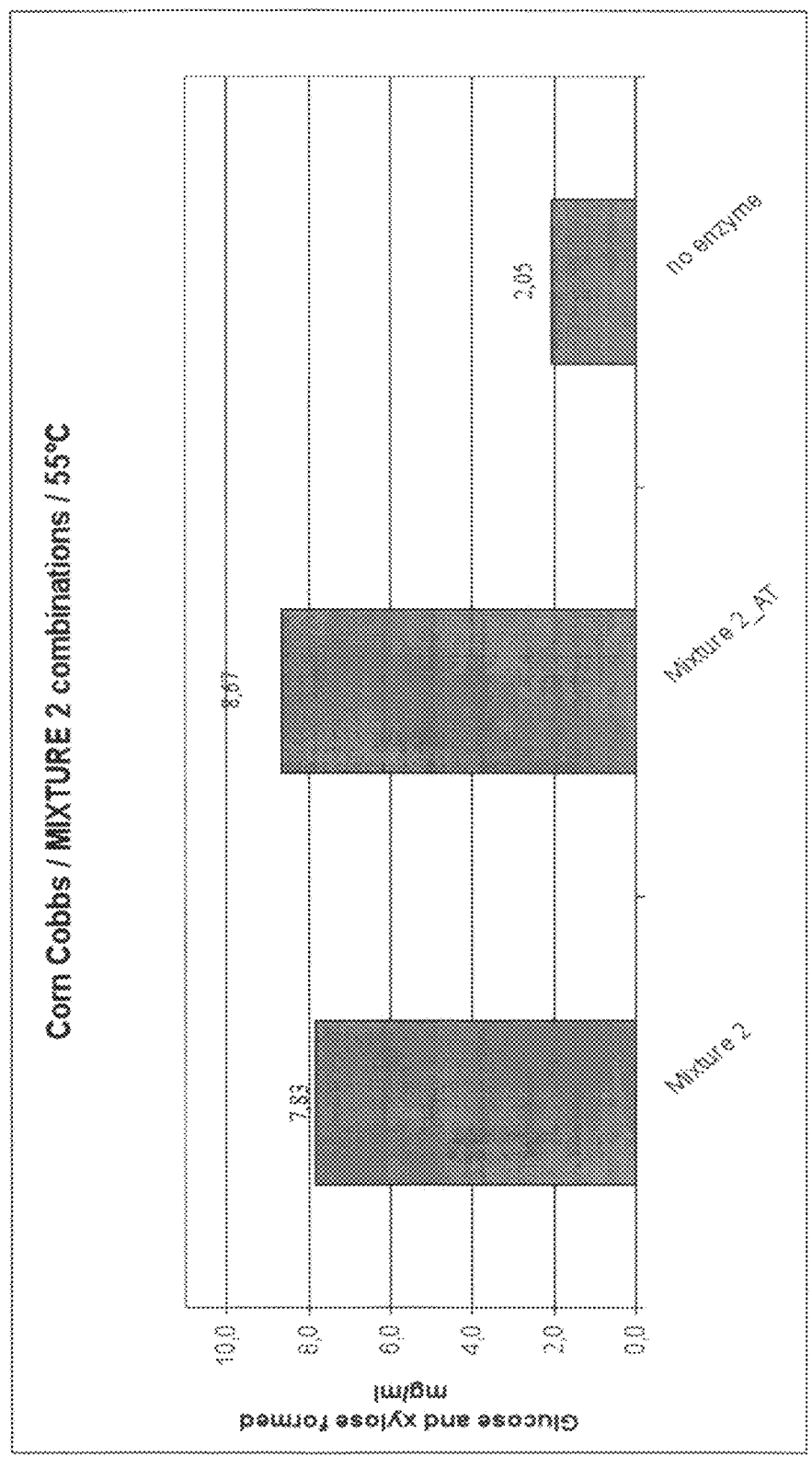
FIG. 5 shows results from hydrolysis of steam exploded corn cobs material performed with enzyme mixtures comprising a CBHII/Cel6A cellobiohydrolase of the invention. The corn cobs substrate was hydrolysed using different enzyme mixtures at a dosage of 5 mg of protein per g of total solids at 55° C. The composition of the thermophilic enzyme mixture (MIXTURE 2) comprising the At_ALKO4245_Cel6A polypeptide of the invention (MIXTURE 2_AT) is described in more detail in Example 5. Samples from duplicated shake flasks were taken after a 72 hours hydrolysis time and quantified by HPLC, in which the concentration of glucose and xylose were determined. The results from the substrate blanks, containing buffer instead of the enzyme sample, were subtracted from the results obtained with the enzyme mixtures. The combined concentration of glucose and xylose is presented.

Similar results were obtained also on steam exploded corn cobs (FIG. 5). The thermophilic enzyme MIXTURE 2 was supplemented with the At_ALKO4245_Cel6A enzyme of the invention. The combined amount of glucose and xylose after 72 hours hydrolysis was remarkably higher than without such supplementation.

According to one preferred embodiment of the invention the method for treating cellulosic and lignocellulosic material, such as the lignocellulosic material including hemicellulose, pectin and lignin involves use of one or more of the CBHII/Cel6A cellobiohydrolases of the invention as an "enzyme composition" or "enzyme preparation" comprising at least one further enzyme capable of hydrolyzing said material. The additional enzymes may be selected from a group of cellobiohydrolase, endoglucanase, beta-glucosidase, beta-glucanase, xyloglucanase, xylanase, beta-xylosidase, mannanase, beta-mannosidase, α-glucuronidase, acetyl xylan esterase, α-arabinofuranosidase, α-galactosidase, pectinase, involving endo- and exo-α-L-arabinases, α-galactosidase, endo- and exo-galactoronase, endopectinlyase, pectinesterase, pectate lyase, phenol esterase, ligninase involving lignin peroxidase, manganese-dependent peroxidase, $H_2O_2$-generating enzyme and laccase with or without a mediator.

The enzyme preparation or composition comprises at least one of the enzymes defined above. It may contain the enzymes in at least partially purified and isolated form. It may even essentially consist of the desired enzyme or enzymes. Alternatively the preparation may be a spent culture medium or filtrate containing one or more of the desired enzymes. Preferably the enzyme preparation is spent culture medium. "Spent culture medium" refers to the culture medium of the host comprising the produced enzymes. Preferably the host cells are separated from said medium after the production. The enzyme preparation or composition may also be a "whole culture broth" obtained, optionally after killing the production host(s) or microorganism(s) without any further downstream processing or purification of the desired cellulolytic enzyme(s). In the "consolidated bioprocess" the enzyme composition or at least some of the enzymes of the enzyme composition may be produced by the fermentative microorganism.

"Isolated polypeptide" in the present context may simply mean that the cells and cell debris have been removed from the culture medium containing the polypeptide. Conveniently the polypeptides are isolated, e.g. by adding anionic and/or cationic polymers to the spent culture medium to enhance precipitation of cells, cell debris and some enzymes that have unwanted side activities. The medium is then filtrated using an inorganic filtering agent and a filter to remove the precipitants formed. After this the filtrate is further processed using a semi-permeable membrane to remove excess of salts, sugars and metabolic products.

In addition to the enzymatic activity, the preparation may contain additives, such as mediators, stabilizers, buffers, preservatives, surfactants and/or culture medium components. Preferred additives are such, which are commonly used in enzyme preparations intended for a particular application. The enzyme preparation may be in the form of liquid, powder or granulate.

According to one embodiment of the invention the enzyme preparation comprises a mixture of CBHs, EGs and BGs, optionally together with hemicellulose degrading enzymes in combination with the CBHII/Cel6A cellobiohydrolases of the invention. Different enzyme mixtures and combinations may be used to suit different substrate materials and process conditions. For example if the degradation process is to be carried out at a high temperature, thermostable enzymes are chosen.

"Hemicellulose" is a heterogeneous group of carbohydrate polymers containing mainly different glucans, xylans and mannans. Hemicellulose consists of a linear backbone with β-1,4-linked residues substituted with short side chains usually containing acetyl acid, 4-O-glucuronic acid, L-arabinose and galactosyl groups. Hemicellulose may be chemically cross-linked to lignin and cellulose. "Xylan degrading enzymes" or "xylanases" include both exohydrolytic and endohydrolytic enzymes such as endo-1,4-beta-D-xylanase (EC 3.2.1.8) or exo-1,4-beta-D-xylosidase (EC 3.2.1.37), which break down hemicellulose to xylose. Gluco- and galactomannans are hydrolyzed by endo-1,4-beta-mannanases (EC3.2.1.78) and beta-mannosidase (EC 3.2.1.25) to yield beta-D-mannose. Enzymes capable of removing side chain substituents include α-glucuronidases, acetyl xylan esterases, α-arabinofuranosidases and α-galactosidases which act cooperatively with the backbone degrading enzymes (Biely et al. 1997; Sundberg and Poutanen, 1991; Stålbrand et al., 1995).

Enzymes involved in degradation of the "pectin" involve endo- and exo-α-L-arabinases and α-galactosidase, endo- and exo-galactoronases, endopectinlyases and pectinesterases (Del Cañizo et al., 1994).

"Lignin" is a complex cross-linked polymer of variously substituted p-hydroxyphenylpropane units. Its hydrolysis involves lignin peroxidases, phenol esterases, manganese-dependent peroxidases, $H_2O_2$-generating enzymes and laccases (Cullen and Kersten, 2004).

The enzymes of the enzyme composition may be added to the lignocellulosic material either simultaneously or sequentially.

According to one preferred embodiment of the invention, the method is applicable on various cellulose, lignocellulose and beta-glucan containing materials, such as plant materials, e.g. wood, including hardwood and softwood, hardwood and softwoods chips, wood pulp, sawdust and forestry and wood industrial waste; herbaceous crops, agricultural biomass as cereal straws, sugar beet pulp, corn fiber, corn stover and cobs, cereal beta-glucans, sugar cane bagasse, stems, leaves, hulls, husks, and the like; waste products as municipal solid waste, newspaper and waste office paper, waste fiber, paper sludge, milling waste of e.g. grains; dedicated energy crops (e.g., willow, poplar, switchgrass or reed canarygrass, and the like).

According to one embodiment of the invention, the method is applicable for production of biofuels, such as ethanol, propanol and butanol and alike from cellulosic material.

Within the context of the invention is a method, wherein the CBHII/Cel6A polypeptide used in the hydrolysis of the cellulosic material derives from *Acremonium thermophilum* CBS 116240 strain and has the amino acid sequence of SEQ ID NO:12 or at least 78%, 80%, 82%, 84%, 86%, 88%, 90%, 92%, 94%, 96%, 97%, 98% or 99% identity with the amino acid sequence of SEQ ID NO:12, or a fragment or variant thereof having cellobiohydrolase activity.

The present invention relates also to a fungal CBHII/Cel6A polypeptide having cellobiohydrolase activity and comprising an amino acid sequence having at least 76% identity to the full-length polypeptide of SEQ ID NO: 12, at least 76% identity to the full-length polypeptide of SEQ ID NO:14, at least 95% identity to the full-length polypeptide of SEQ ID NO:15, or at least 91% identity to the full-length polypeptide of SEQ ID NO:16, or a fragment or variant thereof having similar properties.

The CBHII/Cel6A polypeptide may be obtainable from the filamentous fungal genus *Acremonium, Melanocarpus, Chaetomium* or *Talaromyces*. Preferable species include *Acremonium thermophilum, Melanocarpus albomyces, Chaetomium thermophilum* or *Talaromyces emersonii*.

According to a preferred embodiment of the invention the enzymes are obtainable from a filamentous fungal strain ALKO4245 deposited as CBS 116240 presently classified as *Acremonium thermophilium, Melanocarpus albomyces* strain ALKO4237 deposited as CBS 685.95, *Chaetomium thermophilum* strain ALKO4265 deposited as CBS 730.95 or *Talaromyces emersonii* strain DSM 2432 (in the applicant's culture collection under number RF8069).

According to a preferred embodiment of the invention the fungal CBHII/Cel6A cellobiohydrolase enzyme is a polypeptide having cellobiohydrolase activity and comprising the enzyme of At_ALKO4245_Cel6A having the full-length amino acid sequence of SEQ ID NO: 12.

Another preferred embodiment of the invention is a fungal CBHII/Cel6A cellobiohydrolase enzyme having cellobiohydrolase activity and comprising the enzyme of Ma_ALKO4237_Cel6A with the full-length amino acid sequence of SEQ ID NO: 14.

A further preferred embodiment of the invention is a fungal CBHII/Cel6A cellobiohydrolase enzyme having cellobiohydrolase activity and comprising the enzyme of Ct_ALKO4265_Cel6A with the full-length amino acid sequence of SEQ ID NO: 15.

Still further preferred embodiment of the invention is a fungal CBHII/Cel6A cellobiohydrolase enzyme having cellobiohydrolase activity and comprising the enzyme of Te_RF8069_Cel6A with the full-length amino acid sequence of SEQ ID NO: 16.

According to one preferred embodiment of the invention, the CBHII/Cel6A cellobiohydrolase enzyme is capable in hydrolyzing cellulosic material at moderate to elevated temperatures. The CBHII/Cel6A cellobiohydrolases of the invention are active or stable even at temperatures up to 70° C., such as between 40° C. and 70° C., e.g. between 40° C. and 60° C. or between 50° C. and 60° C., when assayed at the optimum pH of the enzymes using Avicel Ph101 cellulose as a substrate, as described in Example 3. For short hydrolysis times enzyme compositions may be functional up to 80° C. For total hydrolysis longer incubation times are required and, therefore, lower temperatures are normally used. This makes the CBHII/Cel6A cellobiohydrolases of the invention extremely well suited for varying cellulosic substrate hydrolysis processes carried out both at conventional or moderate temperatures and at elevated temperatures requiring thermostability of the enzymes.

According to a preferred embodiment of the invention the fungal CBHII/Cel6A is encoded by an isolated nucleic acid molecule which comprises a polynucleotide sequence, which encodes a polypeptide comprising the amino acid sequence characterized in SEQ ID NO:12, SEQ ID NO:14, SEQ ID NO:15 or SEQ ID NO:16. Thus, within the scope of the invention is CBHII/Cel6A cellobiohydrolase enzyme or polypeptide comprising the amino acid sequence of the full-length form of the At_ALKO4245_Cel6A enzyme characterized in SEQ ID NO: 12, Ma_ALKO4237_Cel6A enzyme characterized in SEQ ID NO: 14, Ct_ALKO4265 characterized in SEQ ID NO:15 or Te_RF8069_Cel6A characterized in SEQ ID NO:16.

Further, within the scope of the present invention are polypeptides encoded by nucleic acid molecules encoding a CBHII/Cel6A polypeptide having cellobiohydrolase activity and at least 76% identity to the full-length amino acid sequence of SEQ ID NO: 12, at least 76% identity to the full-length amino acid sequence of SEQ ID NO: 14, at least 95% identity to the full-length amino acid sequence of SEQ ID NO:15 or at least 91% to the full-length amino acid sequence of SEQ ID NO:16. The identities of the two enzymes are compared within the corresponding sequence regions, i.e. within the full-length region of the CBHII/Cel6A polypeptide.

Within the scope of the invention is a polypeptide sequence, which is encoded by a nucleic acid molecule coding for a fragment of the polypeptide, which polypeptide fragment lacks one or more amino acid residues from the N- and/or C-terminus of the full-length polypeptide of SEQ ID NO: 12, SEQ ID NO: 14, SEQ ID NO:15 or SEQ ID NO:16. The fragment still has the essential catalytic activity or cellobiohydrolase activity of the full-length CBHII/Cel6A cellobiohydrolase and substantially similar properties such as pH and temperature dependence and substrate specificity. The fragment may, for example be an enzyme which lacks the secretion signal sequence or carbohydrate binding domain or CBD.

Also included are natural or synthetic variants of the CBHII/Cel6A cellobiohydrolases, which have properties similar to the polypeptides defined in SEQ ID NO: 12, SEQ ID NO: 14, SEQ ID NO:15 or SEQ ID NO:16. The variation may result from deletion, substitution, insertion, addition or combination of one or more positions in the amino acid sequence.

One preferred embodiment of the invention is a CBHII/Cel6A cellobiohydrolase which is encoded by an isolated nucleic acid molecule comprising a polynucleotide sequence included in SEQ ID NO:11, SEQ ID NO:13, SEQ ID NO:9 or SEQ ID NO:10 or a subsequence thereof.

Within the context of the invention is a CBHII/Cel6A cellobiohydrolase, which is encoded by a nucleic acid molecule or polynucleotide sequence hybridizing under stringent conditions to a polynucleotide sequence or a subsequence thereof included in SEQ ID NO:11, SEQ ID NO:13, SEQ ID NO:9 or SEQ ID NO:10. Also, a preferred embodiment is a polypeptide encoded by a nucleic acid molecule or polynucleotide sequence hybridizing with a probe prepared using PCR, such as the PCR fragment included in SEQ ID NO:7 or SEQ ID NO:8.

Standard molecular biology methods can be used in isolation of cDNA or a genomic DNA of the host organism, e.g. the methods described in the molecular biology handbooks, such as Sambrook and Russell, 2001. The cDNA or a genomic gene encoding the CBHII/Cel6A cellobiohydrolase of the invention may be isolated using DNA probes, which have been prepared based on the amino acid sequence of N-terminal or tryptic peptides of the purified CBHII/Cel6A enzyme. Alternatively, the probe may be designed based on the known nucleotide or amino acid sequences of homologous cellobiohydrolases. The CBHII/Cel6A clones may also be screened based on activity on plates containing a specific substrate for the enzyme or by using antibodies specific for a CBHII/Ce6A cellobiohydrolase.

Hybridization with a DNA probe, such as for example SEQ ID NO: 7 consisting of more than 100-200 nucleotides, is usually performed at "high stringency" conditions, i.e. hybridization at a temperature, which is 20-25° C. below the calculated melting temperature (Tm) of a perfect hybrid, the Tm calculated according to Bolton and McCarthy (1962) and posthybridization washes in low salt concentration. Usually prehybridization and hybridization are performed at least at 65° C. in 6×SSC (or 6×SSPE), 5×Denhardt's reagent, 0.5% (w/v) SDS, 100 µg/ml denatured, fragmented salmon sperm DNA. Addition of 50% formamide lowers the prehybridization and hybridization temperatures to 42° C. High stringency washes are performed in low salt concentration, e.g. in 2×SSC-0.1% SDS (w/v) at RT, and finally in 0.1×SSC-0.1% SDS (w/v) at least at 65° C., e.g. at 68° C.

In the present invention the At_ALKO4245_cel6A, Ma_ALKO4237_cel6A, Ct_ALKO4265_cel6A and Te_RF8069_cel6A genes were isolated with a probe prepared by PCR using stringent hybridization conditions as described in Example 1. Genomic cbh2/cel6A genes were isolated by using oligonucleotide primers designed based on the published nucleotide sequences or using degenerate oligonucleotide primers planned based on the alignment of the previously known amino acid sequences of CBHII/Cel6A proteins.

According to one preferred embodiment of the invention the fungal CBHII/Cel6A cellobiohydrolase enzyme is encoded by an isolated nucleic acid molecule, which comprises the nucleotide sequence of SEQ ID NO:11 encoding the full-length form of the At_ALKO4245_Cel6A enzyme of SEQ ID NO:12. Another preferred embodiment of the invention is a fungal CBHII/Cel6A cellobiohydrolase encoded by an isolated nucleic acid molecule comprising the nucleotide sequence of SEQ ID NO:13, which encodes the full-length form of the Ma_ALKO4237_Cel6A enzyme having the amino acid sequence of SEQ ID NO:14. Another preferred embodiment of the invention is a fungal CBHII/Cel6A cellobiohydrolase encoded by an isolated nucleic acid molecule comprising the nucleotide sequence of SEQ ID NO:9, which encodes the full-length form of the Ct_ALKO4265_Cel6A enzyme having the amino acid sequence of SEQ ID NO:15. Further preferred embodiment of the invention is a fungal CBHII/Cel6A cellobiohydrolase encoded by an isolated nucleic acid molecule comprising the nucleotide sequence of SEQ ID NO:10, which encodes the full-length form of the Te_RF8069_Cel6A enzyme having the amino acid sequence of SEQ ID NO:16.

According to another preferred embodiment of the invention the fungal CBHII/Cel6A cellobiohydrolase is encoded by the polynucleotide sequence included in plasmid pALK2582 deposited in *Escherichia coli* RF8175 under accession number DSM 22946, plasmid pALK2581 deposited in *Escherichia coli* RF8174 under accession number DSM 22945, plasmid pALK2904 deposited in *Escherichia coli* RF8214 under accession number DSM 22947, or plasmid pALK3006 deposited in *Escherichia coli* RF8333 under accession number DSM 23185.

One embodiment of the invention is the CBHII/Cel6A cellobiohydrolase produced from a recombinant expression vector comprising the nucleic acid molecule, which encodes the fungal CBHII/Cel6A cellobiohydrolase as characterized above, operably linked to regulatory sequences capable of directing the expression of a gene encoding said CBHII/Cel6A cellobiohydrolase enzyme in a suitable host. Construction of said recombinant expression vector and use of said vector is described in more detail in Example 2.

Suitable hosts for production of the fungal CBHII/Cel6A cellobiohydrolase are homologous or heterologous hosts, such as the microbial hosts including bacteria, yeasts and fungi. Filamentous fungi, such as *Trichoderma, Aspergillus, Fusarium, Humicola, Chrysosporium, Neurospora, Rhizopus, Penicillium* and *Mortiriella*, are preferred production hosts due to the ease of down-stream processing and recovery of the enzyme product. Suitable hosts include species such as *T. reesei, A. niger, A oryzae, A. sojae, A. awamori* or *A. japonicus* type of strains, *F. venenatum* or *F. oxysporum, H. insolens* or *H. lanuginosa, N. crassa* and *C. lucknowense*, some of which are listed as enzyme production host organisms in e.g. AMFEP 2007 list of commercial enzymes (http://www.amfep.org/list.html). More preferably, the enzyme is produced in a filamentous fungal host of the genus *Trichoderma* or *Aspergillus*, such as *T. reesei*, or *A. niger, A. oryzae* or *A. awamori*. According the most preferred embodiment of the invention the fungal CBHII/Cel6A cellobiohydrolase enzyme is produced in *T. reesei*.

According to the preferred embodiment of the invention the CBHII/Cel6A polypeptide is At_ALKO4245_Cel6A deriving from *Acremonium thermophilum* CBS 116240 and having the amino acid sequence of SEQ ID NO: 12.

The present invention relates also to an isolated nucleic acid molecule comprising a polynucleotide sequence encoding the fungal CBHII/Cel6A cellobiohydrolase selected from the group consisting of:

(a) a nucleic acid molecule or polynucleotide sequence encoding a polypeptide having cellobiohydrolase activity and comprising the full-length amino acid sequence as depicted in SEQ ID NO:12, SEQ ID NO:14, SEQ ID NO:15 or SEQ ID NO:16, or a fragment or variant thereof having similar properties;

(b) a nucleic acid molecule or polynucleotide sequence encoding a polypeptide having cellobiohydrolase activity and at least 76% identity to the full-length amino acid sequence of SEQ ID NO:12, at least 76% identity to the full-length amino acid sequence of SEQ ID NO:14, at least 95% identity to the full-length amino acid sequence of SEQ ID NO:15 or at least 91% identity to the full-length amino acid sequence of SEQ ID NO:16, or a fragment or variant thereof having similar properties;

(c) a nucleic acid molecule comprising the coding sequence of the nucleotide sequence as depicted in SEQ ID NO: 11, SEQ ID NO:13, SEQ ID NO:9 or SEQ ID NO:10;

(d) a nucleic acid molecule comprising the coding sequence of the polynucleotide sequence contained in DSM 22946, DSM 22945, DSM 22947 or DSM 23185;

(e) a nucleic acid molecule the coding sequence of which differs from the coding sequence of a nucleic acid molecule of any one of (c) to (d) due to the degeneracy of the genetic code; and (f) a nucleic acid molecule hybridizing under stringent conditions to a nucleic acid molecule contained in DSM 22946, DSM 22945, DSM 22947 or DSM 23185 or a subsequence thereof, and encoding a polypeptide having cellobiohydrolase activity and an amino acid sequence which shows at least 76% identity to the full-length amino acid sequence as depicted in SEQ ID NO:12, at least 76% to the full-length amino acid sequence of SEQ ID NO:14, at least 95% to the full-length amino acid sequence of SEQ ID NO:15 or at least 91% to the full-length amino acid sequence of SEQ ID NO:16.

The nucleic acid molecule of the invention may be RNA or DNA, wherein the DNA may constitute of the genomic DNA or cDNA.

Standard molecular biology methods can be used in isolation and enzyme treatments of the polynucleotide sequence encoding the fungal CBHII/Cel6A cellobiohydrolase of the invention, including isolation of genomic and plasmid DNA, digestion of DNA to produce DNA fragments, sequencing, *E. coli* transformations etc. The basic methods are described in the standard molecular biology handbooks, e.g. Sambrook and Russell, 2001.

Isolation of the At_ALKO4245_cel6A, Ma_ALKO4237_cel6A, Ct_ALKO4265_cel6A and Te_RF8069_cel6A gene encoding the At_ALKO4245_Cel6A, Ma_ALKO4237_Cel6A, Ct_ALKO4265_Cel6A and Te_RF8069_Cel6A polypeptides is described in Example 1. Briefly, the 1032 bp PCR fragment (SEQ ID NO: 7) and the 831 bp PCR fragment (SEQ ID NO:8) obtained by using the sequences of the degenerate oligonucleotide primers (SEQ ID NO:1 and SEQ ID NO:2) were used to isolate the At_ALKO4245_cel6A gene from *Acremonium thermophilum* ALKO4245 and the Ma_ALKO4237_cel6A gene from *Melanocarpus albomyces* ALKO4237 in pCR®4Blunt-TOPO® vector. The full-length *A. thermophilum* cel6A gene was included in the plasmid pALK2582 deposited in *E. coli* to the DSMZ culture collection under accession number DSM 22946. The full-length *M. albomyces* cel6A gene was included in the plasmid pALK2581 deposited in *E. coli* to the DSMZ culture collection under accession number DSM 22945.

The Ct_ALKO4265_cel6A gene was isolated using the primer pairs of SEQ ID NO:3 and SEQ ID NO:4 and the Te_RF8069_cel6A gene was isolated using the primer pairs of SEQ ID NO:5 and SEQ ID NO:6 as described in Example 1. The PCR fragments containing the full-length cel6A genes from *Chaetomium thermophilum* ALKO4265 and *Talaromyces emersonii* RF8069 were included in plasmids pALK2904 and pALK3006 deposited in *E. coli* to the DSMZ culture collection under accession numbers DSM 22947 and DSM 23185, respectively.

The deduced amino acid sequences of the CBHII/Cel6A cellobiohydrolases were analyzed from the DNA sequences as described in Example 1.

The length of the At_ALKO4245_cel6A (SEQ ID NO: 11) gene, encoding the *Acremonium thermophilum* CBHII/Cel6A cellobiohydrolase (SEQ ID NO: 12), is 1830 by (including the stop codon). Four putative introns were found having the length of 79, 72, 117 and 126 bps. Thus, the coding region of At_ALKO4245_cel6A is 1434 by (stop codon not included) and the deduced protein sequence consists of 478 amino acids including a predicted signal sequence of 18 amino acids (SignalP V3.0; Nielsen et al., 1997; Nielsen and Krogh, 1998 and Bendtsen et al., 2004). The deduced amino acid sequence had homology to the published CBHII/Cel6A sequences when analyzed using the BLAST program, version 2.2.9 at NCBI, National Center for Biotechnology Information; Altschul et al., 1990). The predicted molecular mass of the mature enzyme excluding the signal sequence was 48 918 Da and the predicted pI was 4.82. These predictions were made using the Compute pI/MW tool at ExPASy server (Gasteiger et al., 2003). The identity values of the full-length At_ALKO4245_Cel6A sequence to the corresponding regions of homologous sequences were obtained by using a Clone Manager program (version 9) including the functions "Compare two Sequences/Global/Compare sequences as amino acids/BLOSUM62 scoring matrix". The values (%) showing identity with the other CBHII/Cel6A cellobiohydrolases of the present invention is shown in Table 6. Identity with the published CBHII/Cel6A amino acid sequences is presented in Table 7 and Table 8.

The At_ALKO4245_Cel6A of the invention showed highest homology to the full-length polypeptides of *Thielavia terrestris* NRRL 8126 (SEQ ID NO: 2 in U.S. Pat. No. 7,220,565, Novozymes Inc., US and SEQ ID NO: 49 in WO2009085868, Novozymes A/S, DK), the unnamed protein product of *Podospora anserina* DSM 980 (EMBL accession no. XP_001903170), and the deduced endoglucanase 2 precursor of *Neurospora crassa* OR74A (XM_955677). The identity with the *T. terrestris* protein was within the full-length polypeptide 75%. Identities with *P. anserina* and *N. crassa* polypeptides were 69%.

The length of the Ma_ALKO4237_cel6A (SEQ ID NO: 13) gene, encoding the *Melanocarpus albomyces* CBHII/Cel6A cellobiohydrolase (SEQ ID NO: 14), is 1607 bp (including the stop codon). Two putative introns were found having the length of 93 and 95 bps. Thus, the coding region of Ma_ALKO4237_cel6A is 1416 bp (stop codon not included) and the deduced protein sequence consists of 472 amino acids including a predicted signal sequence of 17 amino acids (SignalP V3.0; Nielsen et al., 1997; Nielsen and Krogh, 1998 and Bendtsen et al., 2004). The predicted molecular mass of the mature enzyme excluding the signal sequence was 48 627 Da and the predicted pI was 4.50. These predictions were made using the Compute pI/MW tool at ExPASy server (Gasteiger et al., 2003). The Ma_ALKO4237_Cel6A of the invention showed highest homology to the full-length polypeptide of an uncharacterized organism, disclosed as an amino acid sequence SEQ ID NO: 413 in WO2008095033 (Syngenta Inc., US) (72%), to the CBHII polypeptide of *Thielavia terrestris* NRRL 8126 (SEQ ID NO:49 in WO2009085868, Novozymes A/S, DK) (71%) and the hypothetical protein CHGG_10762 of *Chaetomium globosum* CBS 148.151 (EMBL accession no. XP001226029) (75% identity).

The length of the Ct_ALKO4265_cel6A (SEQ ID NO: 9) gene, encoding the *Chaetomium thermophilum* CBHII/Cel6A cellobiohydrolase (SEQ ID NO: 15) is 1757 bp (including the stop codon). Three putative introns were found having the length of 77, 196 and 56 bps. Thus, the coding region of Ct_ALKO4265_cel6A is 1425 bp (stop codon not included) and the deduced protein sequence consists of 475 amino acids including a predicted signal sequence of 17 amino acids (SignalP V3.0; Nielsen et al., 1997; Nielsen and Krogh, 1998 and Bendtsen et al., 2004). The predicted molecular mass of the mature enzyme excluding the signal sequence was 49 408 Da and the predicted pI was 5.31. The Ct_ALKO4265_Cel6A of the invention showed highest homology to the deduced cellobiohydrolase of family 6 of *Chaetomium thermophilum* CT2 (EMBL accession no. AY861348; CN 1757709, Shandong Agricultural University, CN), to the polypeptide of *C. thermophilum* CGMCC0859 having cellobiohydrolase II activity (SEQ ID NO: 2 in EP1578964B1, Novozymes A/S, DK) and to the *Chaetomium thermophilum* CBHII of SEQ ID NO: 36 (the amino acid sequence of Sequence listing) or SEQ ID NO:46 (the amino acid sequence of description) or SEQ ID NO:45 (the nucleotide sequence of description) in WO2009059234, Novozymes Inc., US. The identities within the full-length polypeptides were 94%.

The length of the Te_RF8069_cel6A (SEQ ID NO: 10) gene, encoding the *Talaromyces emersonii* CBHII/Cel6A cellobiohydrolase (SEQ ID NO: 16), is 1754 bp (including the stop codon). Seven putative introns were found having the length of 50, 44, 52, 56, 53, 59 and 60 bps. Thus, the coding region of Te_RF8069_cel6A is 1377 bp (stop codon not included) and the deduced protein sequence consists of 459 amino acids including a predicted signal sequence of 19 amino acids (SignalP V3.0; Nielsen et al., 1997; Nielsen and Krogh, 1998 and Bendtsen et al., 2004). The predicted molecular mass of the mature enzyme excluding the signal sequence was 46 618 Da and the predicted pI was 4.27. The Te_RF8069_Cel6A of the invention showed highest homology to the polypeptide of *Talaromyces emersonii* (Q8N1B5 in FIG. 3A-C of WO2006074005, Novozymes Inc., US) and the cellobiohydrolase II of *Talaromyces emersonii* (AY075018). The identities within the full-length amino acid sequences were 90%.

Thus, within the scope of the invention is an isolated polynucleotide sequence or isolated nucleic acid molecule, which encodes a CBHII/Cel6A cellobiohydrolase enzyme or polypeptide comprising the amino acid sequence of the full-length form of the At_ALKO4245_Cel6A enzyme characterized in SEQ ID NO: 12, Ma_ALKO4237_Cel6A enzyme characterized in SEQ ID NO:14, Ct_ALKO4265 characterized in SEQ ID NO:15 or Te_RF8069_Cel6A characterized in SEQ ID NO:16.

Further, within the scope of the present invention are nucleic acid molecules or polynucleotide sequences which encode a CBHII/Cel6A polypeptide having cellobiohydrolase activity and at least 76%, preferably at least 78%, 80%, 82%, 84%, 86%, 88%, 90%, 92%, 94%, 96% or 97%, more preferably at least 98%, most preferably 99% identity to the full-length amino acid sequence of SEQ ID NO: 12. The identities of the two enzymes are compared within the corresponding sequence regions, i.e. within the full-length region of the CBHII/Cel6A polypeptide.

Another preferred embodiment of the invention is a fungal CBHII/Cel6A cellobiohydrolase enzyme showing at least 76%, preferably at least 78%, 80%, 82%, 84%, 86%, 88%, 90%, 92%, 94%, 96% or 97%, more preferably at least 98%, most preferably 99% identity to the full-length amino acid sequence of SEQ ID NO:14.

Further, preferred CBHII/Cel6A cellobiohydrolases show at least 95%, preferably at least 96% or least 97%, even more preferably at least 98% identity, most preferably at least 99% identity to the full-length amino acid sequence of SEQ ID NO: 15.

Other preferred CBHII/Cel6a polypeptides show at least 91%, preferably at least 92%, 93%, 94%, 95%, 96% or 97%, more preferably at least 98%, and most preferably 99% identity to the full-length amino acid sequence of SEQ ID NO: 16.

Within the scope of the invention is an isolated nucleic acid molecule which comprises a polynucleotide sequence encoding a polypeptide, which has the amino acid sequence of the full-length CBHII/Cel6A cellobiohydrolase of the invention as well as fragments or natural or synthetic variants of the polypeptides of the invention which have cellobiohydrolase activity and properties similar to the full-length polypeptides. Such fragment may, for example be an enzyme which lacks the secretion signal sequence or carbohydrate binding domain or CBD.

One preferred embodiment of the invention is an isolated nucleic acid molecule comprising a "coding sequence" of the polynucleotide sequence included in SEQ ID NO:11, SEQ ID NO:13, SEQ ID NO:9 or SEQ ID NO:10 or a subsequence thereof. According to one preferred embodiment of the invention the polypeptide is encoded by the nucleic acid molecule having the nucleotide sequence SEQ ID NO: 11 comprising the coding sequence for the At_ALKO4245_Cel6A enzyme. The expression "coding sequence" means the nucleotide sequence which initiates from the translation start codon (ATG) and stops at the translation stop codon (TAA, TAG or TGA) and may comprise intron regions. The translated full-length polypeptide starts usually with methionine.

According to another preferred embodiment of the invention the isolated nucleic acid molecule comprises a coding sequence of a polynucleotide sequence included in plasmid pALK2582 deposited in *Escherichia coli* RF8175 under accession number DSM 22946, plasmid pALK2581 deposited in *Escherichia coli* RF8174 under accession number DSM 22945, plasmid pALK2904 deposited in *Escherichia coli* RF8214 under accession number DSM 22947, or plasmid pALK3006 deposited in *Escherichia coli* RF8333 under accession number DSM 23185, said polynucleotide sequences encoding the At_ALKO4245_Cel6A, Ma_ALKO4237_Cel6A, Ct_ALKO4265_Cel6A and Te_RF8069_Cel6A cellobiohydrolases, respectively.

The nucleic acid molecule of the invention may also be an analogue of the nucleotide sequence characterized above. The "degeneracy" means analogues of the nucleotide sequence, which differ in one or more nucleotides or codons, but which encode the recombinant CBHII/Cel6A of the invention.

The nucleic acid molecule may also be a nucleic acid molecule or polynucleotide sequence hybridizing under stringent conditions to a polynucleotide sequence contained in plasmids pALK2582, pALK2581, pALK2904 or pALK3006 deposited in *E. coli* under the accession numbers DSM 22946, DSM 22945, DSM 22947 or DSM 23185 or a subsequence thereof, and encoding a polypeptide having cellobiohydrolase activity and an amino acid sequence which within the corresponding sequence region shows at least 76% identity to the full-length amino acid sequence as depicted in SEQ ID NO:12, at least 76% identity to the full-length amino acid sequence of SEQ ID NO:14, at least 95% identity to the full-length amino acid sequence of SEQ ID NO:15 or at least 91% to the full-length amino acid sequence of SEQ ID NO:16. The hybridizing DNA may originate from a fungus belonging to genus *Acremonium, Melanocarpus, Chaetomium* or *Talaromyces* or it may originate from other fungal species.

According to a preferred embodiment of the invention the fungal CBHII/Cel6A cellobiohydrolase enzyme is encoded by an isolated nucleic acid molecule, which comprises the nucleotide sequence of SEQ ID NO:11 encoding the full-length form of the At_ALKO4245_Cel6A enzyme of SEQ ID NO:12.

The present invention relates also to a recombinant expression vector or recombinant expression construct, which can be used to propagate or express the nucleic acid molecule or polynucleotide sequence encoding the chosen CBHII/Cel6A cellobiohydrolase in a suitable prokaryotic or eukaryotic host. The recombinant expression vector comprises DNA or nucleic acid sequences which facilitate or direct expression and secretion of the CBHII/Cel6A polypeptide encoding sequence or gene in a suitable host, such as promoters, enhancers, terminators (including transcription and translation termination signals) and signal sequences operably linked the polynucleotide sequence encoding said polypeptide. The expression vector may further comprise marker genes for selection of the transformant strains or the selection marker may be introduced to the host in another vector construct by co-transformation. Said regulatory sequences may be homologous or heterologous to the production organism or they may originate from the organism, from which the gene encoding the CBHII/Cel6A polypeptide is isolated.

Examples of promoters for expressing the CBHII/Cel6A of the invention in filamentous fungal hosts are the promoters of *A. oryzae* TAKA amylase, alkaline protease ALP and triose phosphate isomerase, *Rhizopus miehei* lipase, *Aspergillus niger* or *A. awamori* glucoamylase (glaA), *Fusarium oxysporum* trypsin-like protease, *Chrysosporium lucknowense* cellobiohydrolase 1 promoter, *Trichoderma reesei* cellobiohydrolase I (Cel7A) etc.

In yeast, for example promoters of *S. cerevisiae* enolase (ENO-1), galactokinase (GAL1), alcohol dehydrogenase (ADH2) and 3-phosphoglycerate kinase can be used to provide expression.

Examples of promoter sequences for directing the transcription of the CBHII/Cel6A polypeptide of the invention in a bacterial host are the promoter of lac operon of *Escherichia coli*, the *Streptomyces coelicolor* agarase dagA promoter, the promoter of the *B. licheniformis* alpha-amylase gene (amyL), the promoter of the *B. stearothermophilus* maltogenic amylase gene (amyM), the promoters of the *B. sublitis* xylA and xylB genes, etc.

Suitable terminators include those of the above mentioned genes or any other characterized terminator sequences.

Suitable transformation or selection markers include those which complement a defect in or adds a new feature, e.g. enzyme activity to the host, for example the dal genes from *B. subtilis* or *B. licheniformis* or *Aspergillus* amdS and niaD. The selection may be based also on a to marker conferring antibiotic resistance, such as ampicillin, kanamycin, chloramphenicol, tetracycline, phleomycin or hygromycin resistance.

Extracellular production of the CBHII/Cel6A of the invention is preferable. Thus, the recombinant vector comprises sequences facilitating secretion in the selected host. The signal sequence of the CBHII/Cel6A cellobiohydrolase of the invention or the presequence or prepeptide may be included in the recombinant expression vector or the natural signal sequence may be replaced with another signal sequence capable of facilitating expression in the selected host. Thus, the chosen signal sequence may be homologous or heterologous to the expression host.

Examples of suitable signal sequences are those of the fungal or yeast organisms, e.g. signal sequences from well-expressed genes. Such signal sequences are well known from the literature.

The recombinant vector may further comprise sequences facilitating integration of the vector into the host chromosomal DNA to obtain stable expression. The vector may also be a fusion construct and comprise sequences encoding a carrier polypeptide, which is genetically fused with the same coding sequence as the coding sequence of the protein of interest and which improves secretion of the polypeptide in a heterologous host organism or which facilitates the protein purification after production. Such carriers include, e.g. the proteins produced in high amounts by the native host, such as the cellulases of *T. reesei* or glucoamylases of *Aspergillus* species. The carrier polypeptide may also be an intact domain of the secretable protein, such as the CBD. The carrier protein and the protein of interest may remain as a fusion after the secretion, or are separated by a proteolytic processing during the protein export process in the host, or are separated chemically or biochemically after the secretion into the supernatant.

The At_ALKO4245_Cel6A, Ma_ALKO4237_Cel6A, Ct_ALKO4265_Cel6A and Te_RF8069_Cel6A cellobiohydrolase of the invention were expressed with their own signal sequence from the *Trichoderma reesei* cbh1 (cel7A) promoter as described in Example 2. The expression construct used to transform the *T. reesei* host included also cbh1 terminator and amdS marker for selecting transformants from untransformed cells.

The present invention relates also to host cells comprising the recombinant expression vector as described above. Suitable hosts for production of the fungal CBHII/Cel6A cellobiohydrolase are homologous or heterologous hosts, such as the microbial hosts including bacteria, yeasts and fungi. Production systems in plant or mammalian cells are also possible.

Filamentous fungi, such *Trichoderma, Aspergillus, Fusarium, Humicola, Chrysosporium, Neurospora, Rhizopus, Penicillium* and *Mortiriella*, are preferred production hosts due to the ease of down-stream processing and recovery of the enzyme product. Suitable expression and production host systems are for example the production system developed for the filamentous fungus host *Trichoderma reesei* (EP 244234), or *Aspergillus* production systems, such as *A. oryzae* or *A. niger* (WO 9708325, U.S. Pat. No. 5,843,745, U.S. Pat. No. 5,770,418), *A. awamori, A. sojae* and *A. japonicus*-type strains, or the production system developed for *Fusarium*, such as *F. oxysporum* (Malardier et al., 1989) or *F. venenatum*, and for *Neurospora crassa, Rhizopus miehei, Mortiriella alpinis, H. lanuginosa* or *H. insolens* or for *Chrysosporium lucknowense* (U.S. Pat. No. 6,573,086). Suitable production systems developed for yeasts are systems developed for *Saccharomyces, Schizosaccharomyces* or *Pichia pastoris*. Suitable production systems developed for bacteria are a production system developed for *Bacillus*, for example for *B. subtilis, B. licheniformis, B. amyloliquefaciens*, for *E. coli*, or for the actinomycete *Streptomyces*. Preferably the CBHII/Cel6A cellobiohydrolase of the invention is produced in a filamentous fungal host of the genus *Trichoderma* or *Aspergillus*, such as *T. reesei*, or *A. niger, A. oryzae, A. sojae*, *A. awamori* or *A. japonicus*-type strains. According the most preferred embodiment of the invention the fungal CBHII/Cel6A cellobiohydrolase is produced in *T. reesei*.

The production host cell may be homologous or heterologous to the CBHII/Cel6A cellobiohydrolase of the invention. Preferably the recombinant host is modified to express and secrete cellulolytic enzymes as its main activity or one of its main activities. This can be done by deleting major homologous secreted genes e.g. the four major cellulases of *Trichoderma* and by targeting heterologous genes to a locus that has been modified to ensure high expression and production levels. For example, the host may be free of homogenous cellobiohydrolases due to removal of said cellobiohydrolases either by inactivation or removal of one or more host cellobiohydrolases, e.g. by deletion of the gene(s) encoding such homogenous or homologous cellobiohydrolase(s).

The present invention relates also to a process for producing a CBHII/Cel6A polypeptide having cellobiohydrolase activity, said process comprising the steps of culturing the natural or recombinant host cell carrying the recombinant expression vector for a CBHII/Cel6A cellobiohydrolase of the invention under suitable conditions and optionally isolating said enzyme. The production medium may be a medium suitable for growing the host organism and containing inducers for efficient expression. Suitable media are well-known from the literature.

The invention relates to a polypeptide having cellobiohydrolase activity, said polypeptide being encoded by the nucleic acid molecule of the invention and which is obtainable by the process described above.

The invention further relates to a process for obtaining an enzyme preparation comprising a CBHII/Cel6A polypeptide, which has cellobiohydrolase activity, said process comprising the steps of culturing a host cell carrying the expression vector of the invention and preparing the whole culture broth, or separating the cells from the spent culture medium and obtaining the supernatant having cellobiohydrolase activity.

The present invention relates also to an enzyme preparation, which comprises the CBHII/Cel6A enzyme characterized above. The enzyme preparation or composition has cellobiohydrolase activity and is obtainable by the process according to the invention.

Within the invention is an enzyme preparation which comprises the fungal CBHII/Cel6A cellobiohydrolase of the invention.

Said enzyme preparation may further comprise different types of enzymes in addition to the CBHII/Cel6A cellobiohydrolase of this invention, for example another cellulase including a cellobiohydrolase, endoglucanase and beta-glucosidase, beta-glucanase, an amylase, a lipase, cutinase, a protease, xylanase, beta-xylosidase, mannanase, beta-mannosidase, α-glucuronidase, acetyl xylan esterase, α-arabinofuranosidase, α-galactosidase, pectinase, involving endo- and exo-α-L-arabinases, α-galactosidase, endo- and exo-galactoronase, xyloglucanase, endopectinlyase, pectate lyase, and pectinesterase, phenol esterase, ligninase involving lignin peroxidase, manganese-dependent peroxidase, $H_2O_2$-generating enzyme and/or an oxidase such as a laccase or peroxidase with or without a mediator. These enzymes are expected to enhance the performance of the CBHII/Cel6A enzyme of the invention by removing the carbohydrates, proteins and oils or fats present in the material to be handled. Said enzymes may be natural or recombinant enzymes produced by the host strain or may be added to the culture supernatant after the production process. The enzyme compositions or enzyme preparations may contain any combination of these enzymes. The CBHII/Cel6A cellobiohydrolases may also be used in combination to commercially available enzyme preparations.

The enzymes needed for the hydrolysis of the cellulosic material according to the invention may be added in an enzymatically effective amount either simultaneously, e.g. in the form of an enzyme mixture, or sequentially, or as a part of the simultaneous saccharification and fermentation (SSF) process or they may be produced by the fermentative microorganism in the consolidated bioprocess.

The enzyme preparation or composition may contain the enzymes in at least partially purified and isolated form. It may even essentially consist of the desired enzyme or enzymes.

Alternatively the preparation may be a whole culture broth or spent culture medium or filtrate containing one or more desired enzymes. In a consolidated bioprocess the enzymes may be produced by the fermentative microorganism used in the process. In addition to the enzymatic activity, the preparation may contain additives, such as mediators, stabilizers, buffers, preservatives, surfactants and/or culture medium components.

Preferred additives are such, which are commonly used in enzyme preparations intended for a particular application. Surfactants are useful in emulsifying grease and wetting surfaces. The surfactant may be a non-ionic including semi-polar and/or anionic and/or cationic and/or zwitterionic. Buffers may be added to the enzyme preparation to modify pH or affect performance or stability of other ingredients. Suitable stabilizers include polyols such as propylene glycol or glycerol, a sugar or sugar alcohol, lactic acid, boric acid, or boric acid derivatives, peptides, etc. Bleaching agent is used to oxidize and degrade organic compounds. Examples of suitable chemical bleaching systems are $H_2O_2$ sources, such as perborate or percarbonate with or without peracid-forming bleach activators such as tetra-acetylethylenediamine, or alternatively peroxyacids, e.g. amide, imide or sulfone type. Chemical oxidizers may be replaced partially or completely by using oxidizing enzymes, such as laccases or peroxidases. Many laccases do not function effectively in the absence of mediators. Builders or complexing agents include substances, such as zeolite, diphosphate, triphosphate, carbonate, citrate, etc. The enzyme preparation may further comprise one or more polymers, such as carboxymethylcellulose, poly(ethylene glycol), poly(vinyl alcohol), poly(vinylpyrrolidone), etc. Also, softeners, caustics, preservatives for preventing spoilage of other ingredients, abrasives and substances modifying the foaming and viscosity properties can be added.

According to one preferred embodiment of the invention said enzyme preparation is in the form of spent culture medium, liquid, powder or granulate. Preferably the enzyme preparation is spent culture medium.

The present invention relates also to various uses of the fungal CBHII/Cel6A cellobiohydrolase of the invention, in which hydrolysis or modification of cellulosic material is desired. Such uses include any application, in which cellulolytic enzymes are conventionally used, such as in fuel, textile, detergent, pulp and paper, food, feed or beverage industry. Addition of the fungal CBHII/Cel6A cellobiohydrolase of the invention to an enzyme composition comprising other cellulose degrading enzymes such as cellobiohydrolase I, endoglucanases and beta-glucosidases, greatly enhances the hydrolysis and leads to almost total hydrolysis of the polymeric cellulose backbone to glucose monomers. The major product of CBHII/Cel6A action is cellobiose composed of two glucose units.

One preferred embodiment is the use of the method of the invention in applications requiring stability/performance of the CBHII/Cel6A cellobiohydrolase at moderate/conventional or to elevated temperatures, i.e. requiring thermophilic or thermostable enzymes. Elevated temperatures are known to enhance the hydrolysis of crystalline cellulose present in cellulosic or lignocellulosic materials, thus reducing the total amount of enzymes needed in hydrolysis or reducing the required hydrolysis time. Also, since at elevated temperatures the viscosity of the lignocellulosic substrate is decreased, thermostable enzymes make it possible to work at higher solid loadings and save in investment costs.

Another preferred embodiment is the use of the CBHII/Cel6A polypeptide of the invention or the enzyme preparation comprising said polypeptide in hydrolyzing cellulosic material for the production of biofuel comprising ethanol, propanol, butanol and alike. In production of biofuel the CBHII/Cel6A cellobiohydrolases of the invention are like other cellulolytic enzymes especially suitable for producing glucose monomers from the polymeric cellulosic material which may then be fermented by yeast strains into ethanol, and used as fuel.

The lignocellulosic material may be pretreated before the enzymatic hydrolysis to disrupt the fiber structure of cellulosic substrates and make the cellulose fraction more accessible to the cellulolytic enzymes. Current pretreatments include mechanical, chemical or thermal processes and combinations thereof. The material may for example be pretreated by steam explosion or acid hydrolysis. The saccharification process, i.e. production of sugar monomers, and fermentation by yeast strains may be performed separately or simultaneously in the same reactor. The CBHII/Cel6A cellobiohydrolase of the invention has a great advantage to the commercial enzymes presently for sale in that it is stable also at elevated temperatures, i.e. is thermostable. Hydrolysis of cellulosic or lignocellulosic materials is known to enhance at elevated temperatures and yield sugar monomers more efficiently.

The use of the CBHII/Cel6A polypeptides of the invention enables the use of high biomass consistency and lead to high sugar and ethanol concentrations. This approach may lead to significant savings in energy and investments costs. The high temperature also decreases the risk of contamination during hydrolysis.

The sugar hydrolysates may also serve as raw material for other non-microbial processes, e.g., for enrichment, isolation and purification of high value sugars or various polymerization processes.

The glucose monomers can also be used as intermediates or raw materials for the production of various chemicals or building blocks for the processes of chemical industry, e.g. in so called biorefinery.

In the pulp and paper industry the polypeptides may be used to modify cellulosic fiber for example in treating kraft pulp, mechanical pulp, or recycled paper.

In textile industry the CBHII/Cel6A cellobiohydrolases find applications in softening and/or improving the feel of cotton fabrics and removing indigo dyes in replacement of stone washing.

In feed industry the CBHII/Cel6A cellobiohydrolases of the invention may be used in degrading the cellulosic or hemicellulosic materials present in feedstocks.

In detergent industry the CBHII/Cel6A cellobiohydrolase may be used in hand or machine laundry or dishwashing compositions for removal of cellulosic stains.

The invention is illustrated by the following non-limiting examples. From the experimental results it can be concluded that the fungal CBHII/Cel6A cellobiohydrolases of the invention are capable of satisfying the greatly varying demands of different industry requiring efficient hydrolysis of cellulosic material present in varying feedstocks.

EXAMPLE 1

Cloning of the Cellobiohydrolase 2 (cbh2) Genes

Standard molecular biology methods were used in the isolation and enzyme treatments of DNA (e.g. isolation of plasmid DNA, digestion of DNA to produce DNA fragments), in *E. coli* transformations, sequencing etc. The basic methods used were either as described by the enzyme, reagent or kit manufacturer or as described in the standard molecular biology handbooks, e.g. Sambrook and Russell (2001). Isolation of genomic DNA was performed as described in detail by Raeder and Broda (1985).

Four thermophilic fungal strains from the Roal Oy culture collection were selected for cloning based on the previous findings that the strains produce thermostable cellulases (WO2007071818; Maheshwari et al., 2000; Murray et al., 2003; Miettinen-Oinonen et al., 2004). The probes for cloning the cbh2 genes from *Acremonium thermophilum* ALKO4245 and *Melanocarpus albomyces* ALKO4237 were synthesised by PCR. Degenerate oligos were planned basing on the alignment of the previously published amino acid sequences of cellobiohydrolase II (CBHII) proteins. The sequences of the homologous primers for the cloning of the cbh2 genes from *Chaetomium thermophilum* ALK4265 and *Talaromyces emersonii* RF8069 strains were obtained from the published nucleotide sequences (AY861348; DQ020255; CQ838150; Murray et al., 2003; AY075018; AF439936). The sequences of the primers are shown in Table 2 (SEQ ID NOs: 1-6).

The probes were amplified by PCR with primers described in Table 2 using the genomic DNA as a template in the reactions. The PCR mixtures of *Acremonium thermophilum* ALKO4245 and *Melanocarpus albomyces* ALKO4237 contained 10 mM Tris-HCl, pH 8.8, 50 mM KCl, 0.1% Triton X-100, 1.5 mM $MgCl_2$, 0.2 mM dNTPs, 5 µM each primer and 1-2 units of Dynazyme EXT DNA polymerase (Finnzymes, Finland) and 0.5-1 µg of the corresponding genomic DNA. The conditions for the PCR reactions were the following: 5 min initial denaturation at 95° C., followed by 30 cycles of 1 min at 95° C., 1 min annealing at 60° C. (±5° C. gradient), 2 min extension at 72° C. and a final extension at 72° C. for 10 min. For PCR-cloning of the cbh2 genes from *Chaetomium thermophilum* ALKO4265 and *Talaromyces emersonii* RF8069 strains, the reactions contained 1× Phusion GC and 1× Phusion HF buffers, respectively, with 0.2 mM dNTPs, 5 µM each primer and 1-2 units of Phusion DNA polymerase (Finnzymes, Finland) and 0.5-1 µg of the corresponding genomic DNA. The conditions for the PCR reactions were the following: 3 min initial denaturation at 98° C., followed by 30 cycles of 30 sec at 98° C., 30 sec annealing at 55° C. (±5° C. gradient), 1-2 min extension at 72° C. and a final extension at 72° C. for 10 min.

Primer combinations described in Table 2 produced a specific DNA product having the expected size (according to calculations basing on published cbh2 sequences). The DNA products were isolated and purified from the PCR reaction mixtures and cloned to pCe4Blunt-TOPO® vector according to the manufacturer's instructions (Invitrogen, USA). The inserts were characterized by sequencing and by performing Southern blot hybridizations to the genomic DNAs digested with several restriction enzymes. The PCR fragments, which were chosen to be used as probes for gene cloning from the *Acremonium thermophilum* ALKO4245 and *Melanocarpus albomyces* ALKO4237 strains are presented in Table 3. In addition, the table describes the PCR fragments containing

TABLE 2

The oligonucleotides used as PCR primers to amplify probes for screening of cbh2 genes from *Acremonium thermophilum* ALKO4245 and *Melanocarpus albomyces* ALKO4237 and to amplify full-length cbh2 genes from *Chaetomium thermophilum* ALKO4265 and *Talaromyces emersonii* RF8069.

| Template, genomic DNA from | Oligonucleotide | Length (bp) | Sequence[a] | SEQ ID NO: |
|---|---|---|---|---|
| ALKO4245 | CBH_1S | 17 | TGGGGNCARTGYGGNGG (s) | 1 |
|  | CBH_1AS | 17 | GCNGGCCANCCNARCCA (as) | 2 |
| ALKO4237 | CBH_1S | 17 | TGGGGNCARTGYGGNGG (s) | 1 |
|  | CBH_1AS | 17 | GCNGGCCANCCNARCCA (as) | 2 |
| ALKO4265 | CBH_8 | 21 | ATGGCTAAGCAGCTGCTGCTC (s) | 3 |
|  | CBH_9 | 20 | TCAGARCGGAGGGTTGGCAT (as) | 4 |
| RF8069 | Te_CBH_A | 44 | TATTATCCGCGGACTGCGCATCA TGCGGAATCTTCTTGCTCTTG (s) | 5 |
|  | Te_CBH_B | 38 | AATTTGGATCCTCAGAACAGCG GGTTAGCATTCGTGAG (as) | 6 |

[a] R = A or G, N = A or G or T or C, Y = T or C;
"s" in the parenthesis = sense strand,
"as" in the parenthesis = antisense strand.

the full-length cbh2 genes from *Chaetomium thermophilum* ALKO4265 and *Talaromyces emersonii* RF8069 strains.

TABLE 3

The primers used in the PCR reactions, probes chosen for screening of the cbh2 genes from *Acremonium thermophilum* ALKO4245 and *Melanocarpus albomyces* ALKO4237 and DNA fragments containing the full-length cbh2 genes from *Chaetomium thermophilum* ALKO4265 and *Talaromyces emersonii* RF8069. The genomic template DNA and the name of the plasmid containing the probe fragment are shown.

| Gene | Forward primer | Reverse primer | Genomic DNA used as a template in PCR reaction | Fragment obtained (kb) | Insert in plasmid | SEQ ID NO: |
|---|---|---|---|---|---|---|
| ALKO4245_cel6A | CBH_1S | CBH_1AS | ALKO4245 | 1.0 kb | pALK2580 | 7 |
| ALKO4237_cel6A | CBH_1S | CBH_1AS | ALKO4237 | 0.8 kb | pALK2576 | 8 |
| ALKO4265_cel6A | CBH_8 | CBH_9 | ALKO4265 | 1.8 kb | pALK2904 | 9 |
| RF8069_cel6A | Te_CBH_A | Te_CBH_B | RF8069 | 1.8 kb | pALK3006 | 10 |

The deduced amino acid sequences from all these PCR fragments had homology to the published CBHII/Cel6A sequences (BLAST program, version 2.2.9 at NCBI, National Center for Biotechnology Information; Altschul et al., 1990). The 1757 bp PCR fragment in pALK2904 plasmid (SEQ ID NO: 9) and the 1788 bp PCR fragment in pALK3006 plasmid (SEQ ID NO: 10) contained the full-length cbh2/cel6A genes from *Chaetomium thermophilum* ALKO4265 and *Talaromyces emersonii* RF8069, respectively. The gene encoding the *Chaetomium thermophilum* ALKO4265 was named as Ct_ALKO4265_cel6A and *Talaromyces emersonii* RF8069 gene was named as Te_RF8069_cel6A. The *E. coli* strains RF8214 (=pALK2904) and RF8333 (=pALK3006) were deposited to the DSM collection under the accession numbers DSM 22947 and DSM 23185, respectively.

*Acremonium thermohilum* ALKO4245 and *Melanocarpus albomyces* ALKO4237 genomic DNAs were digested with several restriction enzymes for Southern blot analysis. The probes for the hybridizations were the 1032 bp (SEQ ID NO: 7) and 831 bp (SEQ ID NO:8) EcoRI fragments, cut from the plasmids pALK2580 and pALK2576, respectively. The above probes were labeled by using digoxigenin according to supplier's instructions (Roche, Germany). Hybridizations were performed over night at 68° C. After hybridization the filters were washed 2×5 min at RT using 2×SSC-0.1% SDS followed by 2×15 min at 68° C. using 0.1×SSC-0.1% SDS.

From the genomic DNA of *Acremonium thermophilum* ALKO4245, approximate 8 kb XbaI-digested fragment was hybridized using dioxigenin-labeled 1032 bp EcoRI fragment from the pALK2580 as a probe. Correspondingly, about 4.5 kb BamHI-digested fragment was hybridized with dioxigenin-labeled 831 bp EcoRI fragment of the pALK2576 from the genomic DNA of the *Melanocarpus albomyces* ALKO4237. The hybridizing genomic DNA fragments were isolated from the pool of the digested genomic fragments based on their size. The genomic fragments were isolated from agarose gel and were cloned to pBluescript II KS+ (Stratagene, USA) vectors cleaved with either XbaI (*Acremonium thermophilum* ALKO4245) or BamHI (*Melanocarpus albomyces* ALKO4237). Ligation mixtures were transformed to *Escherichia coli* XL10-Gold cells (Stratagene) and plated on LB (Luria-Bertani) plates containing 50-100 μg/ml ampicillin. The *E. coli* colonies were screened for positive clones using colonial hybridization with the pALK2580 and pALK2576 inserts as probes in the hybridization conditions correspondingly to that described above for Southern blot analyses, except using the hybridization temperature of 65° C. instead of 68° C. Several positive clones were collected from the plates. They were shown by restriction digestion to contain inserts of expected sizes. The full-length gene encoding the *Acremonium thermophilum* ALKO4245 CBHII/Cel6A (At_ALKO4245_Cel6A, SEQ ID NO: 11) was sequenced from the 7 kb XbaI insert and the plasmid containing this insert was named pALK2582. The *E. coli* strain RF8175 including the plasmid pALK2582 was deposited to the DSM collection under the accession number DSM 22946. The gene encoding the *Acremonium thermohilum* ALKO4245 protein was named as At_ALKO4245_cel6A. Correspondingly, the full-length gene encoding the *Melanocarpus albomyces* ALKO4237 CBHII/Cel6A (Ma_ALKO4237_Cel6A, SEQ ID NO: 12) was sequenced from the 5 kb BamHI insert and the plasmid containing this insert was named pALK2581. The *E. coli* strain RF8174 including the plasmid pALK2581 was deposited to the DSM collection under the accession number DSM 22945. The gene encoding the *Melanocarpus albomyces* ALKO4237 was named as Ma_ALKO4237_cel6A. The relevant information on the genes and the deduced protein sequences (SEQ ID NOs: 9-16) are summarized in Table 4 and Table 5, respectively.

TABLE 4

The summary on the cbh2/cel6A genes isolated from *Acremonium thermophilum* ALKO4245, *Melanocarpus albomyces* ALKO4237, *Chaetomium thermophilum* ALKO4265 and *Talaromyces emersonii* RF8069.

| Gene | Length with introns (bp)[a] | Coding region (bp)[b] | No of putative introns | Lengths of putative introns (bp) | SEQ ID NO: |
|---|---|---|---|---|---|
| At_ALKO4245_cel6A | 1830 | 1434 | 4 | 79, 72, 117, 126 | 11 |
| Ma_ALKO4237_cel6A | 1607 | 1416 | 2 | 93, 95 | 13 |

TABLE 4-continued

The summary on the cbh2/cel6A genes isolated from *Acremonium thermophilum* ALKO4245, *Melanocarpus albomyces* ALKO4237, *Chaetomium thermophilum* ALKO4265 and *Talaromyces emersonii* RF8069.

| Gene | Length with introns (bp)[a] | Coding region (bp)[b] | No of putative introns | Lengths of putative introns (bp) | SEQ ID NO: |
|---|---|---|---|---|---|
| Ct_ALKO4265_cel6A | 1757 | 1425 | 3 | 77, 196, 56 | 9 |
| Te_RF8069_cel6A | 1754 | 1377 | 7 | 50, 44, 52, 56, 53, 59, 60 | 10 |

[a] The STOP codon is included.
[b] The STOP codon is not included.

TABLE 5

The summary of the amino acid sequences deduced from the cbh2/cel6A genes sequences from *Acremonium thermophilum* ALKO4245, *Melanocarpus albomyces* ALKO4237, *Chaetomium thermophilum* ALKO4265 and *Talaromyces emersonii* RF8069.

| CBHII/Cel6A protein | No of aas | Length of ss NN/HMM[a] | CBD[b] | Predicted MW (Da), ss not incl[c] | Predicted pI, ss not incl | SEQ ID NO: |
|---|---|---|---|---|---|---|
| At_ALKO4245_Cel6A | 478 | 18 | Q26 to L63 | 48918 | 4.82 | 12 |
| Ma_ALKO4237_Cel6A | 472 | 17 | Q25 to L62 | 48627 | 4.50 | 14 |
| Ct_ALKO4265_Cel6A | 475 | 17 | Q25 to I62 | 49408 | 5.31 | 15 |
| Te_RF8069_Cel6A | 459 | 19 | Q20 to V55 | 46618 | 4.27 | 16 |

[a] The prediction on the signal sequence was made using the program SignalP V3.0 (Nielsen et al., 1997; Nielsen and Krogh, 1998; Bendtsen et al., 2004); the NN value was obtained using neural networks.
[b] The cellulose-binding domain (CBD), the amino acids of the CBD region are indicated [M1(Met #1) included in numbering].
[c] The predicted signal sequence was not included. The prediction was made using the Compute pI/MW tool at ExPASy server (Gasteiger et al., 2003).

The comparison of the deduced CBHII/Cel6A sequences from *Acremonium thermophilum* ALKO4245, *Melanocarpus albomyces* ALKO4237, *Chaetomium thermophilum* ALKO4265 and *Talaromyces emersonii* DSM 2432 (RF8069) to each other is presented in Table 6. A program of Clone Manager (version 9) including the functions "Compare Two Sequences/Global/Compare sequences as amino acids/BLOSUM62 scoring matrix" was used for determining the degree of identity.

TABLE 6

The identity values (%) obtained from alignment of the deduced CBHII/Cel6A amino acid sequences from *Acremonium thermophilum* ALKO4245, *Melanocarpus albomyces* ALKO4237, *Chaetomium thermophilum* ALKO4265 and *Talaromyces emersonii* RF8069.

|  | ALKO4245_Cel6A | ALKO4237_Cel6A | ALKO4265_Cel6A | RF8069_Cel6A |
|---|---|---|---|---|
| ALKO4245_Cel6A | 100 | 67 | 68 | 66 |
| ALKO4237_Cel6A |  | 100 | 71 | 60 |
| ALKO4265_Cel6A |  |  | 100 | 61 |
| RF8069_Cel6A |  |  |  | 100 |

The full-length amino acid sequences including the signal sequences were aligned. A program of Clone Manager 9 (Compare Two Sequences/Global/Compare sequences as amino acids/BLOSUM62 scoring matrix) was used for determining the degree of identity.

The comparison of the deduced CBHII/Cel6A sequences from *Acremonium thermophilum* ALKO4245, *Melanocarpus albomyces* ALKO4237, *Chaetomium thermophilum* ALKO4265 and *Talaromyces emersonii* RF8069 to the sequences found from the databases are shown in Tables 7 and 8.

TABLE 7

The highest identity sequences to the deduced CBHII/Cel6A amino acid sequences from *Acremonium thermophilum* ALKO4245, *Melanocarpus albomyces* ALKO4237, *Chaetomium thermophilum* ALKO4265 and *Talaromyces emersonii* RF8069.

| Organism and accession number | Identity (%) |
|---|---|
| At_ALKO4245_Cel6A | 100 |
| *Podospora anserina*, XP_001903170 | 69 |
| *Neurospora crassa*, XM_955677 | 69 |
| Ma_ALKO4237_Cel6A | 100 |
| *Chaetomium globosum*, XP_001226029 | 75 |
| Ct_ALKO4265_Cel6A | 100 |
| *Chaetomium thermophilum*, AY861348 | 94 |
| Te_RF8069_Cel6A | 100 |
| *Talaromyces emersonii*, AY075018 | 90 |

The full-length amino acid sequences including the signal sequences were aligned. The database search was performed using BLAST (tblastn, nr/nt database), and Clone Manager 9 program (Compare Two Sequences/Global/Compare sequences as amino acids/BLOSUM62 scoring matrix) was used for determining the degree of identity.

TABLE 8

The highest identity patent sequences to the deduced CBHII/Cel6A amino acid sequences from *Acremonium thermophilum* ALKO4245, *Melanocarpus albomyces* ALKO4237, *Chaetomium thermophilum* ALKO4265 and *Talaromyces emersonii* RF8069.

| Organism and accession number | Identity (%) |
|---|---|
| At_ALKO4245_Cel6A | 100 |
| U.S. Pat. No. 7,220,565 B2, SEQ ID: 2 | 75 |
| WO2009085868 A1, SEQ ID: 49 | 75 |
| Ma_ALKO4237_Cel6A | 100 |
| WO2008095033 A2, SEQ ID: 413 | 72 |
| WO2009085868 A1, SEQ ID: 49 | 71 |
| Ct_ALKO4265_Cel6A | 100 |
| EP1578964 B1, SEQ ID: 2 | 94 |
| WO2009059234 A2, SEQ ID: 45*[)] | 94 |
| CN1757709A | 94 |

TABLE 8-continued

The highest identity patent sequences to the deduced CBHII/Cel6A amino acid sequences from *Acremonium thermophilum* ALKO4245, *Melanocarpus albomyces* ALKO4237, *Chaetomium thermophilum* ALKO4265 and *Talaromyces emersonii* RF8069.

| Organism and accession number | Identity (%) |
|---|---|
| Te_RF8069_Cel6A | 100 |
| WO2006074005 A2, FIG. 3A-C | 90 |

The full-length amino acid sequences including the signal sequences were aligned. The Chemical Abstracts Service (CAS) Registry System and Patented Protein Sequences NCBI database searches were performed using BLAST, and Clone Manager 9 program (Compare Two Sequences/Global/Compare sequences as amino acids/BLOSUM62 scoring matrix) was used for determining the degree of identity.
*[)]WO200959234 description refers to SEQ ID NO: 45 (DNA) or SEQ ID NO: 46 (protein). WO200959234 Sequence listing refers to SEQ ID NO: 35 (DNA) or SEQ ID NO: 36 (protein).

EXAMPLE 2

Production of Recombinant CBHII/Cel6A Proteins in *Trichoderma reesei*

Expression plasmids were constructed for production of recombinant CBHII/Cel6A proteins from *Acremonium thermophilum* ALKO4245, *Melanocarpus albomyces* ALKO4237, *Chaetomium thermophilum* ALKO4265 and *Talaromyces emersonii* RF8069 in *Trichoderma reesei*. The expression plasmids constructed are listed in Table 9. The recombinant cbh2/cel6A genes, including their own signal sequences, were exactly fused to the *T. reesei* cbh1/cel7A promoter by PCR. The transcription termination was ensured by the *T. reesei* cbh1/cel7A terminator and the *A. nidulans* amdS marker gene was used for selection of the transformants as described in Paloheimo et al. (2003). The linear expression cassettes (FIG. 1) were isolated from the vector backbones after EcoRI or EcoRI-SpeI digestion and were transformed into *T. reesei* protoplasts. The host strain used does not produce any of the four major *T. reesei* cellulases (CBHI, CBHII, EGI, EGII). The transformations were performed as in Penttilä et al. (1987) with the modifications described in Karhunen et al. (1993), selecting acetamide as a sole nitrogen source (amdS marker gene). The transformants were purified on selection plates through single conidia prior to sporulating them on PD.

TABLE 9

The expression cassettes constructed to produce CBHII/Cel6A recombinant proteins from *Acremonium thermophilum* ALKO4245, *Melanocarpus albomyces* ALKO4237, *Chaetomium thermophilum* ALKO4265 and *Talaromyces emersonii* RF8069 in *Trichoderma reesei*.

| Cellobiohydrolase II protein | Expression plasmid | Expression cassette [a] | Terminator [b] |
|---|---|---|---|
| At_ALKO4245_Cel6A | pALK2906 | 9.4 kb EcoRI | 125 bp (XbaI) |
| Ma_ALKO4237_Cel6A | pALK2901 | 9.3 kb EcoRI-SpeI | 258 bp (DraIII) |
| Ct_ALKO4265_Cel6A | pALK2903 | 9.2 kb EcoRI | |
| Te_RF8069_Cel6A | pALK3010 | 7.9 kb EcoRI | |

The overall structure of the expression cassettes was as described in FIG. 1. The cloned cbh2/cel6A genes were exactly fused to the *T. reesei* cbh1/cel7A promoter.

[a] The expression cassette for *T. reesei* transformation was isolated from the vector backbone by using either EcoRI or EcoRI-SpeI digestion.

[b] The number of the nucleotides after the STOP codon of the cloned recombinant gene that was included in the expression cassette. The restriction site at the 3'-end of the genomic gene fragment that was used in the construction of the expression cassette is indicated in parenthesis. The Ct_ALKO4265_cel6A gene fragment was excised from the 3'-end by EcoRI (a site present in the pCR ®4Blunt-TOPO ® vector). Correspondigly, the Te_RF8069_cel6A gene fragment was excised from its 3'-end by BamHI (a site created after stop codon in PCR). This leaves no original Ct_ALKO4265_cel6A or Te_RF8069_cel6A terminator in the constructs prior to the cbh1 terminator sequence.

The CBHII/Cel6A production of the transformants was analyzed from the culture supernatants of the shake flask cultivations. The transformants were inoculated from the PD slants to shake flasks containing 50 ml of complex lactose-based cellulase inducing medium (Joutsjoki et al., 1993) buffered with 5% $KH_2PO_4$. The CBHII/Cel6A protein production of the transformants was analyzed from the culture supernatants after growing them for 7 days at 30° C., 250 rpm. Heterologous production of recombinant proteins was analyzed by SDS-PAGE with subsequent Coomassie staining. The genotypes of the chosen transformants were confirmed by using Southern blot analyses in which several genomic digests were included and the respective expression cassette was used as a probe.

The best-producing transformants were chosen to be cultivated in laboratory scale bioreactors. The transformants were cultivated in lab bioreactors at 28° C. in the cellulase inducing complex medium for 3-4 days with pH control 4.4±0.2 ($NH_3/H_3PO_4$) to obtain material for the application tests. The supernatants were recovered by centrifugation and filtering through Seitz-K 150 and EK filters (Pall SeitzSchenk Filtersystems GmbH, Bad Kreuznach, Germany).

EXAMPLE 3

Figure 2:
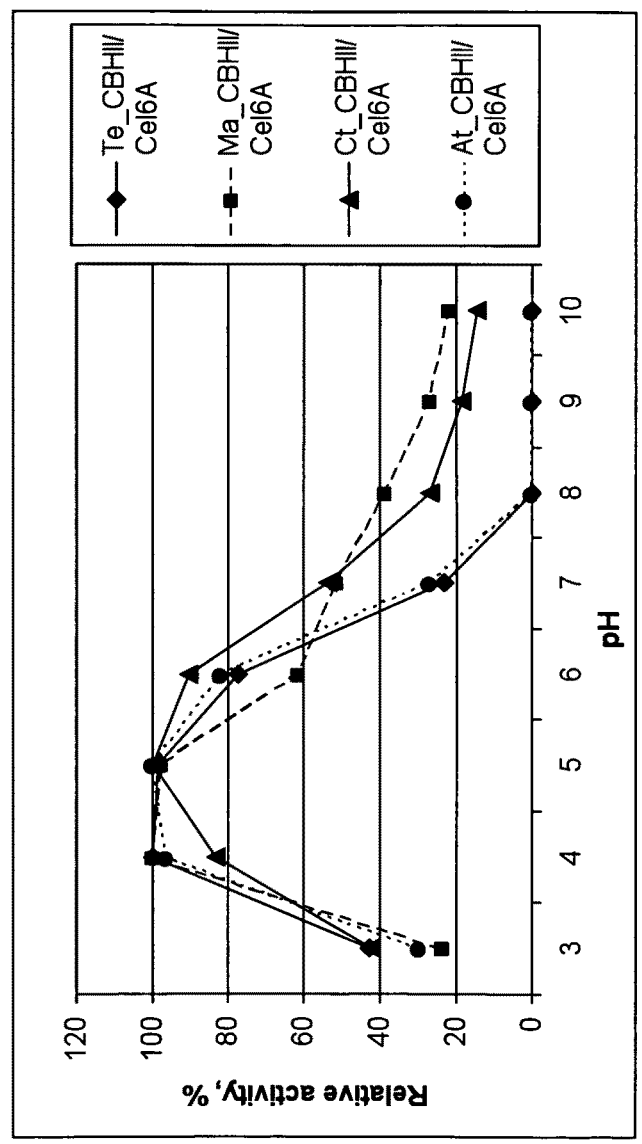
FIG. 2 shows determination of pH dependency for the enzyme compositions (100 μg protein in reaction) comprising the recombinant CBHII/Cel6A cellobiohydrolases of *Acremonium thermophilum* CBS 116240, *Melanocarpus albomyces* CBS 685.95; *Chaetomium thermophilum* CBS 730.95 and *Talaromyces emersonii* DSM 2432. The hydrolysis was performed on Avicel Ph 101 cellulose within a pH range from 3 to 10 at 50° C. for 21 hours. The formation of reducing sugars was determined by para-hydroxybenzoic-acidhydrazide (PAHBAH) method (Lever, 1972) using a cellobiose standard curve.
Figure 3:
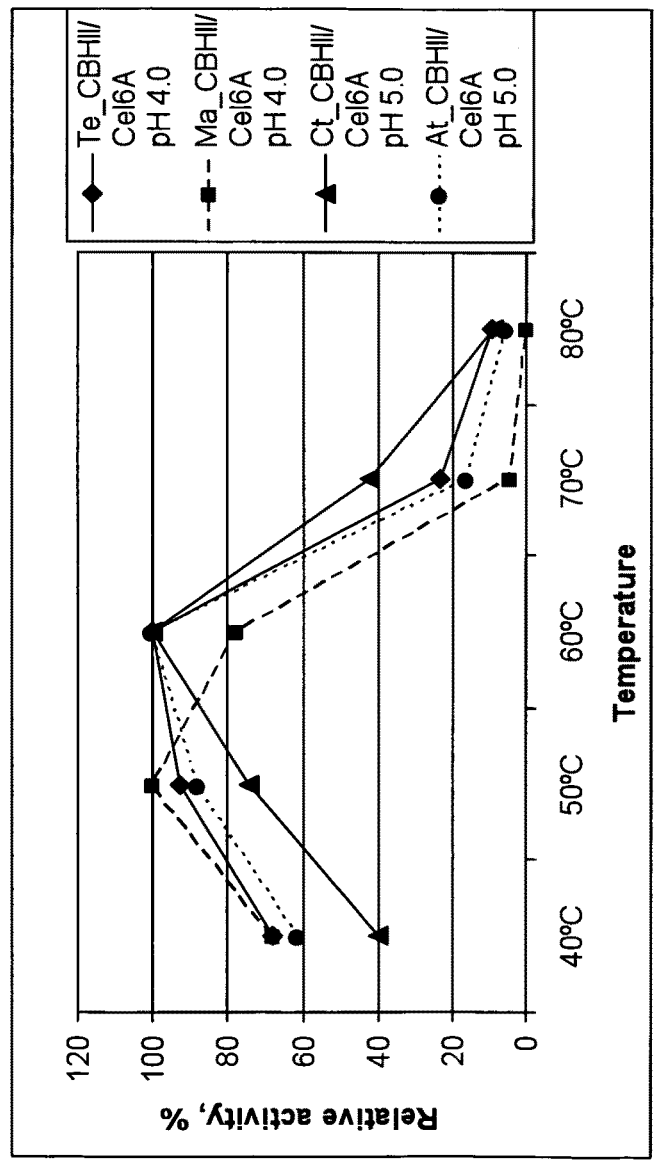
FIG. 3 shows determination of thermal stability for the enzyme compositions (100 μg protein in reaction) comprising the recombinant CBHII/Cel6A cellobiohydrolases of *Acremonium thermophilum* CBS 116240, *Melanocarpus albomyces* CBS 685.95; *Chaetomium thermophilum* CBS 730.95 and *Talaromyces emersonii* DSM 2432. The hydrolysis was performed on Avicel Ph 101 cellulose within a temperature range from 40° C. to 80° Cat optimal pH of the enzyme compositions for 21 hours. The formation of reducing sugars was determined by para-hydroxybenzoic-acidhydrazide (PAHBAH) method (Lever, 1972) using a cellobiose standard curve.

Hydrolysis of Crystalline Cellulose (Avicel) by the Recombinant CBHII/Cel6A Enzymes The recombinant CBHII/Cel6A enzyme preparations were characterized in terms of pH dependence and thermal stability using crystalline cellulose (Avicel) as a substrate. The pH dependence and thermal stability for recombinant CBHII/Cel6A proteins from *Acremonium thermophilum* ALKO4245, *Melanocarpus albomyces* ALKO4237, *Chaetomium thermophilum* ALKO4265 and *Talaromyces emersonii* RF8069 were determined within a pH range of 3.0-10.0 and temperature range of 40° C.-80° C., respectively. The crystalline cellulose (Ph 101, Avicel; Fluka, Bucsh, Switzerland) hydrolysis assays were performed in 2.0 ml tube scale in 50 mM sodium acetate pH 6.0. For determination of the pH optima, substrate solutions (Avicel, 50 mg/ml in sodium acetate, pH 6.0) of pH range from 3 to 10 were shaken with the enzyme preparations (100 μg protein in reaction) at 50° C., and the final volume of the reaction mixture was 650 The hydrolysis was continued for 21 hours and stopped by adding 326 μl of stop reagent containing 9 vol of 94% ethanol and 1 vol of 1 M glycine (pH 11). The solution was filtered through a Millex GV13 0.22 μm filtration unit (Millipore, Billerica, Mass., USA). The formation of soluble reducing sugars in the supernatant was determined by para-hydroxybenzoic-acidhydrazide (PAHBAH) method (Lever, 1972) using a cellobiose standard curve (200 μM to 1200 μM cellobiose). A freshly made 0.1 M PAHBAH (Sigma-Aldrich, St. Louis, Mo., USA) in 0.5 M NaOH solution (200 μl) was added to 300 μl of the filtered sample and boiled for 10 minutes after which the solution was cooled to room temperature. The absorbance at 405 nm was measured from duplicate samples by Multiskan EX (Thermo Labsystems, Franklin, Mass., USA). Correspondingly, thermal stability of the recombinant CBHII/Cel6A proteins was determined in Avicel substrate solutions of temperature range from 40° C. to 80° C. at the optimum pH with the reaction time of 21 hours. Results indicate that the pH optimum for *Talaromyces emersonii* RF8069 CBHII/Cel6A and *Melanocarpus albomyces* ALKO4237 CBHII/Cel6A is at 4.0, whereas *Chaetomium thermophilum* ALKO4265 and *Acremonium thermophilum* ALKO4245 enzymes have pH optimum at 5.0 (FIG. 2). Thermal stability was found to be substantially higher for *Acremonium thermophilum* ALKO4245, *Chaetomium thermophilum* ALKO4265 and *Talaromyces emersonii* RF8069 CBHII/Cel6A as compared to that of *Melanocarpus albomyces* ALKO4237 protein (FIG. 3).

EXAMPLE 4

Hydrolysis of Hardwood Substrate with Enzyme Preparations Comprising a Recombinant CBHII/Cel6A Cellobiohydrolase Steam exploded hardwood was suspended in 0.05 M sodium acetate buffer, pH 4.8. The final weight of the hydrolysis mixture was 20 g of which the total solids concentration was 2% (w/w). The substrate was hydrolysed using different enzyme mixtures at a dosage of 5 mg of protein per g of total solids in 50 ml shake flasks. The protein contents of the enzyme components and the mixes were determined using the Pierce BCA assay kit (Thermo Scientific, Product number 23227) with Bovine Serum Albumin (Thermo Scientific, Product number 23209) as standard. The shake flasks were agitated in a linear-shaking waterbath adjusted in different temperatures. For each sample point, a sample of 1 ml was taken from duplicate shake flasks, and boiled for 10 minutes to terminate the enzymatic hydrolysis, centrifuged, and the supernatant was analysed for reaction products from the hydrolysis. The blanks containing substrate alone (only buffer added instead of enzymes) were prepared identically to the other samples.

Three separate mixture combinations were prepared (a thermophilic MIXTURE 2, a mesophilic MIXTURE ACC and a mesophilic MIXTURE *T. REESEI* ENZYMES) with different Cel6A/CBHII replacements.

A mixture of thermostable cellulases was prepared using the following components:

Thermophilic Cel7A/CBHI preparation containing *Thermoascus aurantiacus* ALKO4242 Cel7A with genetically attached CBD of *T. reesei* CBH1/Cel7A (WO2007071818).

Thermophilic endoglucanase preparation containing *Acremonium thermophilum* ALKO4245 Cel45A endoglucanase (At EG_40/Cel45A, WO2007071818).

Thermophilic β-glucosidase preparation containing *Thermoascus aurantiacus* ALKO4242 β-glucosidase (Ta βG_81/Cel3A, WO2007071818).

Thermophilic xylanase preparation containing *Nonomurea flexuosa* Xyn11A (AM24, WO2005100557, AB Enzymes Oy, FI)).

All cellulases were heterologously produced as monocomponents in *Trichoderma reesei* host strain having cellulase-free background (the genes encoding the four major cellulases Cel7A/CBHI, Cel6A/CBHII, Cel7B/EGI and Cel5A/EGII were deleted). Crude culture supernatants were used in the mixture. The enzyme components were combined as follows (per 10 ml of mixture): CBHI/Cel7A preparation 330 mg (71.2%), endoglucanase preparation 105 mg (22.7%), β-glucosidase preparation 7.5 mg (1.6%) and xylanase preparation 21 mg (4.5%). The volume was made up to 10 ml with tap water. The final protein concentration of the mixture was 46.35 mg/ml. This enzyme mixture was designated as MIXTURE 2.

For testing Cel6A/CBHII performance in the hydrolysis with MIXTURE 2, 15% (49.5 mg) of the CBHI/Cel7A component of MIXTURE 2 was replaced by Ma_ALKO4237_Cel6A (MIXTURE 2_MA), Ct_ALKO4265_Cel6A (MIXTURE 2_CT), or At_ALKO4245_Cel6A (MIXTURE 2_AT), respectively.

A state-of-the-art mixture was prepared by combining the following components (per 10 ml of mixture): ECONASE® CE (Roal Oy, a classical *T. reesei* enzyme product) 470 mg (94%), β-glucosidase preparation (At βG_101/Cel3A, WO2007071818) 20 mg (4%) and xylanase preparation (Ta XYN_30, WO2007071818) 10 mg (2%). The volume was made up to 10 ml with tap water. The final protein concentration in this mixture was 50 mg/ml. This enzyme mixture was designated as MIXTURE *T. REESEI* ENZYMES. At βG_101/Cel3A and Ta XYN_30 enzymes were heterologously produced as monocomponents in *Trichoderma reesei* host strain having cellulase-free background.

For testing Cel6A/CBHII performance in the hydrolysis with MIXTURE *T. REESEI* ENZYMES, 15% (70.5 mg) of the ECONASE® CE component of MIXTURE T. REESEI ENZYMES was replaced by Ma_ALKO4237Cel6A (MIXTURE TR_MA), Ct_ALKO4265_Cel6A (MIXTURE TR_CT), or At_ALKO4245_Cel6A (MIXTURE TR_AT), respectively.

MIXTURE ACC was prepared from commercial Accellerase® 1000 (from Genencor International/Danisco A/S) product (per 10 ml): Accellerase® 1000 400 mg protein (100%). The volume was made up to 10 ml with tap water. The final protein concentration in this mixture was 40 mg/ml.

For testing Cel6A/CBHII performance in the hydrolysis with MIXTURE ACC, 15% (60 mg) of the Accellerase® 1000 component of MIXTURE ACC was replaced by Ma_ALKO4237_Cel6A (MIXTURE ACC_MA), Ct_ALKO4265_Cel6A (MIXTURE ACC_CT), or At_ALKO4245_Cel6A (MIXTURE ACC_AT), respectively.

For MIXTURE 2 combinations, the hydrolysis was performed at 55° C., while the hydrolysis temperature for MIXTURE *T. REESEI* ENZYMES and MIXTURE ACC experiments was 37° C. Samples were taken from the hydrolysis after 72 h, quantified by HPLC and the concentrations of glucose and xylose were determined. The results from the substrate blanks were subtracted from the samples with enzymes, and the concentration of glucose and xylose combined is shown in FIG. 4A-C.

The results clearly show better performance of the MIXTURE 2 with the thermostable Cel6A/CBHII enzymes at 55° C. The amount of sugars released from the hardwood substrate was found to increase 12%, 14% and 26% by supplementing with Ma_ALKO4237_Cel6A, Ct_ALKO4265_Cel6A or At_ALKO4245_Cel6A enzymes in the MIXTURE 2, respectively. *Acremonium thermophilum* ALKO4245 enzyme was found to be best-performing Cel6A/CBHII herein studied (FIG. 4A). At_ALKO4245_Cel6A shows increased hydrolysis also at 37° C. added either in the state-of-the-art *Trichoderma* mixture (MIXTURE *T. REESEI* ENZYMES) (FIG. 4B) or in the commercial product (MIXTURE ACC) (FIG. 4C).

EXAMPLE 5

Hydrolysis of Corn Cobs with Enzyme Preparations Comprising a Recombinant CBHII/Cel6A Cellobiohydrolase Steam exploded corn cobbs was suspended in 0.05 M sodium acetate buffer, pH 4.8. The final weight of the hydrolysis mixture was 20 g of which the total solids concentration was 2% (w/w). The substrate was hydrolysed using different enzyme mixtures at a dosage of 5 mg of protein per g of total solids in 50 ml shake flasks. The protein contents of the enzyme components and the mixes were determined using the Pierce BCA assay kit (Thermo Scientific, Product number 23227) with Bovine Serum Albumin (Thermo Scientific, Product number 23209) as standard. The shake flasks were agitated in a linear-shaking waterbath adjusted at 55° C. For each sample point, a sample of 1 ml was taken from duplicate shake flasks, and boiled for 10 minutes to terminate the enzymatic hydrolysis, centrifuged, and the supernatant was analysed for reaction products from the hydrolysis. The blanks containing substrate alone (only buffer added instead of enzymes) were prepared identically to the other samples.

A mixture of thermostable cellulases was prepared using the following components:

Thermophilic Cel7A/CBHI preparation containing *Thermoascus aurantiacus* ALKO4242 Cel7A with genetically attached CBD of *T. reesei* CBHI/Cel7A (WO2007071818).

Thermophilic endoglucanase preparation containing *Acremonium thermophilum* ALKO4245 Cel45A endoglucanase (At EG_40/Cel45A, WO2007071818).

Thermophilic β-glucosidase preparation containing *Thermoascus aurantiacus* ALKO4242 β-glucosidase (Ta βG_81/Cel3A, WO2007071818).

Thermophilic xylanase preparation containing *Nonomurea flexuosa* Xyn11A (AM24, WO2005100557).

All cellulases were heterologously produced as monocomponents in *Trichoderma reesei* host strain having cellulase-free background (the genes encoding the four major cellulases Cel7A/CBHI, Cel6A/CBHII, Cel7B/EGI and Cel5A/EGII were deleted). Crude culture supernatants were used in the mixture. The enzyme components were combined as follows (per 10 ml of mixture): CBHI/Cel7A preparation 330 mg (71.2%), endoglucanase preparation 105 mg (22.7%), β-glucosidase preparation 7.5 mg (1.6%) and xylanase preparation 21 mg (4.5%). The volume was made up to 10 ml with tap water. The final protein concentration of the mixture was 46.35 mg/ml. This enzyme mixture was designated as MIXTURE 2.

For testing At_ALKO4245_Cel6A performance in the hydrolysis with MIXTURE 2, 15% (49.5 mg) of the CBHI/Cel7A component of MIXTURE 2 was replaced by At_ALKO4245_Cel6A (MIXTURE 2_AT), respectively.

Samples were taken from the hydrolysis after 72 h, quantified by HPLC and the concentrations of glucose and xylose were determined. The results from the substrate blanks were subtracted from the samples with enzymes, and the concentration of glucose and xylose combined is shown in FIG. 5.

Similar to that described in the Example 4, the results here clearly show better performance of the MIXTURE 2 with the At_ALKO4245_Cel6A enzyme at 55° C. for the corn cobs substrate.

REFERENCES

Altschul S F, W Gish, W Miller, E W Myers and D J Lipman. 1990. Basic local alignment search tool. J. Mol. Biol. 215: 403-410.

AMFEP, 2007. Association of Manufacturers and Formulators of Enzyme products, List of commercial enzymes at http://www.amfep.org/list.html (updated 30 Nov. 2007).

Badger, P C. 2002. Ethanol from cellulose: a general review. In Trends in new crops and new uses. J Janick and A Whipkey (eds.). ASHS Press, Alexandria, Va., USA, pp. 17-21.

Bendtsen J D, H Nielsen, G von Heijne and S Brunak. 2004. Improved prediction of signal peptides: SignalP 3.0. J. Mol. Biol. 340:783-795.

Biely P, M Vrsanska, M Tenkanen and D Kluepfel. 1997. Endo-beta-1,4-xylanase families: differences in catalytic properties. Journal of Biotechnology 57: 151-166.

Bolton E T and B J McCarthy. 1962. A general method for the isolation of RNA complementary to DNA. Proc. Nat. Acad. Sci. USA 48:1390-1397.

Collins C M, P G Murray, S Denman, A Grassick, T T Teeri, L Byrnes and M G Tuohy. 2003. Molecular cloning of the cellobiohydrolase genes of *Talaromyces emersonii*. Biochem Biophys Res. Comm. 301:280-286.

Cullen D and P J Kersten. 2004. Enzymology and molecular biology of lignin degradation. In: The Mycota III. Biochemistry and molecular biology. R Brambl and GA Marzluf (eds.). $2^{nd}$ edition, Springer-Verlag, Berlin-Heidelberg, pages 249-273.

Del Cañizo A N, R A Hours, M V Miranda, O Cascone. 1994. Fractionation of fungal pectic enzymes by immobilised metal ion affinity chromatography. J. Sci. Food Agric. 64:527-531.

Edman P and G Begg. 1967. A protein sequenator. Eur. J. Biochem. 1:80-91.

Galagan J E, S E Calvo, K A Borkovich, E U Selker, N D Read, D Jaffe, W FitzHugh, L J Ma, S Smirnov, S Purcell, B Rehman, T Elkins, R Engels, S Wang, C B Nielsen, J Butler, M Endrizzi, D Qui, P Ianakiev, D Bell-Pedersen, M A Nelson, M Werner-Washburne, C P Selitrennikoff, J A Kinsey, E L Braun, A Zelter, U Schulte, G O Kothe, G Jedd, W Mewes, C Staben, E Marcotte, D Greenberg, A Roy, K Foley, J Naylor, N Stange-Thomann, R Barrett, S Gnerre, M Kamal, M Kamvysselis, E Mauceli, C Bielke, S Rudd, D Frishman, S Krystofova, C Rasmussen, R L Metzenberg, D D Perkins, S Kroken, C Cogoni, G Macino, D Catcheside, W Li, R J Pratt, S A Osmani, C P DeSouza, L Glass, M J Orbach, J A Berglund, R Voelker, O Yarden, M Plamann, S Seiler, J Dunlap, A Radford, R Aramayo, D O Natvig, L A Alex, G Mannhaupt, D J Ebbole, M Freitag, I Paulsen, M S Sachs, E S Lander, C Nusbaum, B Birren. 2003. The genome sequence of the filamentous fungus *Neurospora crassa*. Nature 422:859-868.

Gasteiger E, A Gattiker, C Hoogland, I Ivanyi, R D Appel and A Bairoch. 2003. ExPASy: the proteomics server for indepth protein knowledge and analysis. Nucleic Acids Res. 31: 3784-3788.

Ghose T K. 1987. International Union of Pure and Applied Chemistry. Measurement of cellulase activities. Pure and Appl. Chem. 59: 257-268.

Henrissat B. 1991. A classification of glycosyl hydrolases based on amino acid sequence similarities. Biochem. J. 280: 309-316.

Henrissat B and A Bairoch. 1993. New families in the classification of glycosyl hydrolases based on amino acid sequence similarities. Biochem. J. 293: 781-788.

Henrissat B and A Bairoch. 1996. Updating the sequence-based classification of glycosyl hydrolases. Biochem. J. 316: 695-696

Henrissat B, T T Teeri and R A J Warren. 1998. A scheme for designating enzymes that hydrolyse the polysaccharides in the cell wall of plants. FEBS Letters 425: 352-354.

Hong J, H Tamaki, K Yamamoto and H Kumagai. 2003a. Cloning of a gene encoding a thermo-stabile endo-β-1,4-glucanase from *Thermoascus aurantiacus* and its expression in yeast. Biotechnol. Letters 25: 657-661.

Hong J, H Tamaki, K Yamamoto and H Kumagai. 2003b. Cloning of a gene encoding thermostable cellobiohydrolase from *Thermoascus aurantiacus* and its expression in yeast. Appl. Microbiol. Biotechnol. 63: 42-50.

Joutsjoki V V, T K Torkkeli and K M H Nevalainen. 1993. Transformation of *Trichoderma reesei* with the *Hormoconis resinae* glucoamylase P (gamP) gene: production of a heterologous glucoamylase by *Trichoderma reesei*. Curr. Genet. 24: 223-228.

Karhunen T, A Mantyla, K M H Nevalainen and P L Suominen. 1993. High frequency one-step gene replacement in *Trichoderma reesei*. I. Endoglucanase I overproduction. Mol. Gen. Genet. 241:515-522.

Karlsson J, M Saloheimo, M Siika-aho, M Tenkanen, M Penttilä and F Tjerneld. 2001. Homologous expression and characterization of Cel61A (EGIV) of *Trichoderma reesei*. Eur. J. Biochem. 268:6498-6507.

Kurabi A, A Berlin, N Gilkes, D Kilburn, A Markov, A Skomarovsky, A Gusakov, O Okunev, A Sinitsyn, D Gregg, D Xie and J Saddler. 2005. Enzymatic hydrolysis of steam-exploded and ethanol organosols-pretreated Douglas-Fir by novel and commercial fungal cellulases. Appl. Biochem and Biotechnol. Vol 121-124: 219-229.

Laemmli U K. 1970. Cleavage of structural proteins during the assembly of the head of bacteriophage T4. Nature 227: 680-685.

Lever M. 1972. A new reaction for colorimetric determination of carbohydrates. Anal. Biochem., 47: 276-279.

Maheshwari R, G Bharadwaj and M K Bhat. 2000. Thermophilic fungi: their physiology and enzymes. Microbiol. Mol. Biol. Rev. 64:461-488.

Malardier L, M J Daboussi, J Julien, C Roussel, C Scazzocchio and Y Brygoo. 1989. Cloning of the nitrate reductase gene (niaD) of *Aspergillus nidulans* and its use for transformation of *Fusarium oxysporum*. Gene 78:147-156.

Miettinen-Oinonen A, J Londesborough, V Joutsjoki, R Lantto, J Vehmaanpera. 2004. Three cellulases from *Melanocarpus albomyces* with application in textile industry. Enzyme Microb. Technol. 34:332-341.

Miller G L. 1959. Use of dinitrosalisylic acid reagent for determination of reducing sugars. Anal. Chem. 31:426-428.

Murray P G, C M Collins, A Grassick and M G Tuohy. 2003. Molecular cloning, transcriptional, and expression analysis of the first cellulase gene (cbh2), encoding cellobiohydrolase II, from the moderately thermophilic fungus *Talaromyces emersonii* and structure prediction of the gene product. Biochem. Biophys. Res. Commun. 301:280-286.

Nielsen H, J Engelbrecht, S Brunak and G von Heijne. 1997. Identification of prokaryotic and eykaryotic signal peptides and prediction of their cleavage sites. Protein Engineering 10:1-6.

Nielsen H and A Krogh. 1998. Prediction of signal peptides and signal anchors by a hidden Markov model. In: Proceedings of the Sixth International Conference on Intelligent Systems for Molecular Biology (ISMB 6), AAAI Press, Menlo Park, Calif., pp. 122-130.

Paloheimo M, A Mantyla, J Kallio, and P Suominen. 2003. High-yield production of a bacterial xylanase in the filamentous fungus *Trichoderma reesei* requires a carrier polypeptide with an intact domain structure. Appl. Env. Microbiol. 69:7073-7082.

Penttilä M, H Nevalainen, M Rano, E Salminen and J Knowles. 1987. A versatile transformation system for the cellulolytic filamentous fungus *Trichoderma reesei*. Gene 61:155-164.

Raeder U and P Broda. 1985. Rapid preparation of DNA from filamentous fungi. Lett. Appl. Microbiol. 1:17-20.

Robyt J F and W J Whelan. 1972. Reducing value methods for maltodextrins: I. Chain length dependence of alkaline 3,5- dinitrosalisylate and chain-length independence of alkaline copper. Anal. Biochem. 45:510-516.

Sambrook J and D W Russell. 2001. Molecular cloning, a laboratory manual. Cold Spring Harbor Laboratory, New York, US.

Shaw A J, K K Podkaminer, S G Desai, J S Bardsley, S R Rogers, P G Thorne, D A Hogsett and L R Lynd. 2008. Metabolic engineering of a thermophilic bacterium to produce ethanol at high yield. Proc. Natl. Acad. Sci. USA 105: 13769-13774.

Sinnott M L. 1990. Catalytic mechanisms of enzymic glycosyl transfer. Chem. Rev. 90: 1171-1202.

Somogyi M. 1952. Notes on sugar determination. J. Biol. Chem. 195:19-23.

Srisodsuk M, T Reinikainen, M Penttilä and T Teeri. 1993. Role of the interdomain linker peptide of *Trichoderma reesei* cellobiohydrolase I in its interaction with crystalline cellulose. J. Biol. Chem. 268(28): 20756-61.

Stålbrand H, A Saloheimo, J Vehmaanpera, B Henrissat and M Penttilä. 1995. Cloning and expression in *Saccharomyces cerevisiae* of a *Trichoderma reesei* β-mannanase gene containing a cellulose binding domain. Appl. Environ. Microbiol. 61:1090-1097.

Sundberg M and K Poutanen. 1991. Purification and properties of two acetylxylan esterases of *Trichoderma reesei*. Biotechnol. Appl. Biochem. 13: 1-11.

Suurnäkki A, M Tenkanen, M Siika-aho, M-L Niku-Paavola, L Viikari and J Buchert. 2000. *Trichoderma reesei* cellulases and their core domains in the hydrolysis and modification of chemical pulp. Cellulose 7: 189-209.

van Tilbeurgh H, F Loonties, C de Bruyne and M Claeyssens. 1988. Fluorogenic and chromogenic glycosides as substrates and ligands of carbohydrases. Methods Enzymol. 160:45-59.

Tomme P, S McRae, T Wood and M Claeyssens. 1988. Chromatographic separation of cellulolytic enzymes. Methods in Enzymol. 160: 187-192.

Tuohy M, J Walsh, P Murray, M Claeyssens, M Cuffe, A Savage and M Coughan. 2002. Kinetic parameters and mode of action of cellobiohydrolases produced by *Talaromyces emersonii*. Biochem. Biophys. Acta 1596: 366-380.

Waffenschmidt S and L Jaenicke. 1987. Assay of reducing sugars in the nanomole range with 2,2'bicinchoninate. Anal. Biochem. 165:337-340.

Withers S G, D Dombroski, L A Berven, D G Kilburn, R C Miller Jr, R A J Warren and N R Gilkes. 1986. Direct $^1$H NMR determination of the stereochemical course of hydrolases catalysed by glucanase components of the cellulose complex. Biochem. Biophys. Res. Commun. 139: 487-494.

Withers S G and Aebersold R. 1995. Approaches to labeling and identification of active site residues in glycosidases. Protein Sci. 4:361-372.

The invention claimed is:

1. A recombinant polypeptide, wherein said polypeptide has cellobiohydrolase activity and comprises an amino acid sequence having at least 80% identity to:
   (i) the full-length polypeptide of SEQ ID NO: 12;
   (ii) a fragment comprising amino acids 19-478 of SEQ ID NO: 12;
   (iii) a fragment comprising amino acids 1-25 directly linked to amino acids 64-478 of SEQ ID NO: 12; or
   (iv) a fragment comprising amino acids 19-25 directly linked to amino acids 64-478 of SEQ ID NO: 12.

2. The recombinant polypeptide of claim 1, wherein the polypeptide comprises amino acids 19-478.

3. The isolated recombinant polypeptide of claim 1, wherein said polypeptide comprises the amino acid sequence of SEQ ID NO: 12.

4. The isolated recombinant polypeptide of claim 1, wherein said polypeptide hydrolyzes cellulosic material at a temperature in the range of 30° C. to 80° C.

5. The recombinant polypeptide of claim 1, wherein said polypeptide is encoded by an isolated nucleic acid molecule, which comprises a polynucleotide sequence encoding a polypeptide comprising the amino acid sequence of SEQ ID NO: 12 or an amino acid sequence having at least 80% identity to the amino acid sequence of the full-length polypeptide of SEQ ID NO:12.

6. The recombinant polypeptide of claim 1, wherein said polypeptide is encoded by the polynucleotide sequence included in plasmid pALK2582. which is contained in Escherichia coli that is deposited under accession number DSM 22946.

7. The recombinant polypeptide of claim 1, wherein said polypeptide is produced from a recombinant expression vector comprising a nucleic acid molecule comprising a polynucleotide sequence encoding the isolated polypeptide of claim 10, the polynucleotide sequence being operably linked to regulatory sequences capable of directing expression of the nucleic acid molecule in a host cell.

8. The recombinant polypeptide of claim 7, wherein the host cell is a microbial host cell.

9. The recombinant polypeptide of claim 7, wherein the host cell is of the genus Trichoderma, Aspergillus, Fusarium, Humicola, Chrysosporium, Neurospora, Rhizopus, Penicillium, or Mortierella.

10. The recombinant polypeptide of claim 9, wherein the host cell is of the genus Trichoderma or Aspergillus.

11. An enzyme preparation that comprises the recombinant polypeptide of claim 1.

12. The enzyme preparation of claim 11, wherein the recombinant polypeptide comprises the amino acid sequence of SEQ ID NO: 12.

13. The enzyme preparation of claim 11, wherein said enzyme preparation further comprises an enzyme selected from the group consisting of cellobiohydrolase, endoglucanase, beta-glucosidase, beta-glucanase, xyloglucanase, xylanase, beta-xylosidase, mannanase, beta-mannosidase, α-glucuronidase, acetyl xylan esterase, α-arabinofuranosidase, α-galactosidase, pectinase, involving endo- and exo-α-L-arabinases, α-galactosidase, endo- and exo-galactoronase, endopectinlyase, pectate lyase and pectinesterase, phenol esterase, ligninase involving lignin peroxidase, manganese-dependent peroxidase, $H_2O_2$ generating enzyme, and laccase with or without a mediator.

14. The enzyme preparation of claim 11, wherein said enzyme preparation is in a form of whole culture broth, spent culture medium, liquid, powder or granulate.

15. A detergent comprising the recombinant polypeptide of claim 1.

16. The detergent of claim 15, wherein the detergent is a laundry detergent.

17. The detergent of claim 15, wherein the detergent is a dishwashing detergent.

18. The recombinant polypeptide of claim 1, wherein the polypeptide comprises amino acids 1-25 directly linked to amino acids 64-478 of SEQ ID NO: 12.

19. The recombinant polypeptide of claim 1, wherein the polypeptide comprises amino acids 19-25 directly linked to amino acids 64-478 of SEQ ID NO: 12.

20. The recombinant polypeptide of claim 1, wherein the polypeptide comprises an amino acid sequence that is not the amino acid sequence set forth in SEQ ID NO: 12.

21. The recombinant polypeptide of claim 1, wherein the polypeptide comprises an amino acid sequence that is 80% identical to the full-length polypeptide of SEQ ID NO: 12.

22. The recombinant polypeptide of claim 1, wherein the polypeptide comprises an amino acid sequence that is 82% identical to the full-length polypeptide of SEQ ID NO: 12.

23. The recombinant polypeptide of claim 1, wherein the polypeptide comprises an amino acid sequence that is 84% identical to the full-length polypeptide of SEQ ID NO: 12.

24. The recombinant polypeptide of claim 1, wherein the polypeptide comprises an amino acid sequence that is 86% identical to the full-length polypeptide of SEQ ID NO: 12.

25. The recombinant polypeptide of claim 1, wherein the polypeptide comprises an amino acid sequence that is 88% identical to the full-length polypeptide of SEQ ID NO: 12.

26. The recombinant polypeptide of claim 1, wherein the polypeptide comprises an amino acid sequence that is 90% identical to the full-length polypeptide of SEQ ID NO: 12.

27. The recombinant polypeptide of claim 1, wherein the polypeptide comprises an amino acid sequence that is 92% identical to the full-length polypeptide of SEQ ID NO: 12.

28. The recombinant polypeptide of claim 1, wherein the polypeptide comprises an amino acid sequence that is 94% identical to the full-length polypeptide of SEQ ID NO: 12.

29. The recombinant polypeptide of claim 1, wherein the polypeptide comprises an amino acid sequence that is 96% identical to the full-length polypeptide of SEQ ID NO: 12.

30. The recombinant polypeptide of claim 1, wherein the polypeptide comprises an amino acid sequence that is 97% identical to the full-length polypeptide of SEQ ID NO: 12.

31. The recombinant polypeptide of claim 1, wherein the polypeptide comprises an amino acid sequence that is 98% identical to the full-length polypeptide of SEQ ID NO: 12.

32. The recombinant polypeptide of claim 1, wherein the polypeptide comprises an amino acid sequence that is 99% identical to the full-length polypeptide of SEQ ID NO: 12.

33. The recombinant polypeptide of 26 wherein the polypeptide comprises an amino acid sequence that is not the amino acid sequence set forth in SEQ ID NO: 12.

34. A detergent comprising the recombinant polypeptide of claim 20.

35. A detergent comprising the recombinant polypeptide of claim 22.

36. A method for treating cellulosic material with a recombinant polypeptide or an enzyme preparation comprising said recombinant polypeptide, wherein said polypeptide has cellobiohydrolase activity and comprises an amino acid sequence having at least 80% identity to the full-length polypeptide of SEQ ID NO: 12, or a fragment thereof having cellobiohydrolase II activity, wherein the fragment is selected from the group consisting of amino acids 19-478 of SEQ ID NO: 12, amino acids 1-25 directly linked to amino acids 64-478 of SEQ ID NO: 12, and amino acids 19-25 directly linked lo amino acids 64-478 of SEP ID NO; 12, and wherein said method comprises the following steps:
  i) producing said polypeptide or the enzyme preparation comprising said polypeptide or a fermentative microorganism producing said polypeptide;
  ii) reacting the cellulosic material with said polypeptide or the enzyme preparation comprising said polypeptide or the fermentative microorganism producing said polypeptide; and
  iii) obtaining partially or fully hydrolyzed cellulosic material.

37. The method according to claim 36, wherein the recombinant polypeptide comprises the amino acid sequence of SEQ ID NO: 12.

38. The method according to claim 36, wherein the recombinant polypeptide hydrolyzes cellulosic material at a temperature in the range of 30° C. to 80° C.

39. The method according to claim 36, wherein the cellulosic material is treated with an enzyme composition comprising said recombinant polypeptide in combination with at least one further enzyme capable of hydrolyzing said cellulosic material selected from the group consisting of cellobionhydrolase, endoglucanase, beta-glucosidase, beta-glucanase, xyloglucanase, xylanase, beta-xylosidase, mannanase, beta-mannosidase, α-glucuronidase, acetyl xylan esterase, α-arabinofuranosidase, α-galactosidase, pectinase, involving endo- and exo-α-L-arabinases, α-galactosidase, endo- and exo-galactoronase, endopectinlyase, pectate lyase, and pectinesterase, phenol esterase, ligninase involving lignin peroxidase, manganese-dependent peroxidase. $H_2O_2$-generating enzyme, and laccase with or without mediators.

40. The method according to claim 39, wherein the recombinant polypeptide and the at least one further enzyme arc added to the cellulosic material cither simultaneously or sequentially.

41. The method according lo claim 36, wherein the cellulosic material is selected from the group consisting of plant materials, agricultural biomass, waste products and dedicated energy crops.

42. The method according to claim 36, further comprising contacting the partially or fully hydrolyzed cellulosic material with the recombinant polypeptide or the enzyme preparation comprising the recombinant polypeptide thereby producing glucose monomers and fermenting the glucose monomers in the presence of a fermentative microorganism into ethanol. wherein the ethanol is used in production of biofuel.

43. The method of claim 42, wherein the fermentative microorganism is yeast.

44. A method of hydrolyzing cellulosic material, the method comprising contacting the cellulosic material with the recombinant polypeptide of claim 10 or the enzyme preparation of claim 11.

45. A method for preparing biofuel. the method comprising contacting cellulosic or lignocellulosic biomass with the recombinant polypeptide of claim 10 or the enzyme preparation of claim 11 thereby producing glucose monomers and fermenting said glucose monomers in the presence of a fermentative microorganism into ethanol, wherein the ethanol is used in preparation of biofuel.

46. A method for degrading cellulosic or hemicellulosic materials in feedstock, the method comprising contacting the feedstock with a composition comprising the recombinant polypeptide of claim 1.

47. A method for removing cellulosic stains from a fabric, the method comprising contacting the fabric with a composition comprising the recombinant polypeptide of claim 1.

48. A method for softening a cotton fabric, the method contacting the fabric with a composition comprising the recombinant polypeptide of claim 1.

49. A method for removing indigo dyes from a fabric, the method comprising contacting the fabric with a composition comprising the recombinant polypeptide of claim 1.

50. A method of hydrolyzing cellulosic material, the method comprising contacting the cellulosic material with the recombinant polypeptide of claim 20.

51. A method for preparing biofuel. the method comprising contacting cellulosic or lignocellulosic biomass with the recombinant polypeptide of claim 20 thereby producing glucose monomers and fermenting said glucose monomers in the presence of a fermentative microorganism into ethanol, wherein the ethanol is used in preparation of biofuel.

52. A method for degrading cellulosic or hemicellulosic materials in feedstock, the method comprising contacting the feedstock with a composition comprising the recombinant polypeptide of claim 20.

53. A method for removing cellulosic stains from a fabric, the method comprising contacting the fabric with a composition comprising the recombinant polypeptide of claim 20.

54. A method for softening a cotton fabric, the method comprising contacting the fabric with a composition comprising the recombinant polypeptide of claim 20.

55. A method for removing indigo dyes from a fabric, the method comprising contacting the fabric with a composition comprising the recombinant polypeptide of claim 20.

* * * * *

UNITED STATES PATENT AND TRADEMARK OFFICE
CERTIFICATE OF CORRECTION

PATENT NO. : 8,580,552 B2  
APPLICATION NO. : 12/930189  
DATED : November 12, 2013  
INVENTOR(S) : Terhi Puranen Page 1 of 4

It is certified that error appears in the above-identified patent and that said Letters Patent is hereby corrected as shown below:

Title page, item (73), Assignee name should read -- Roal Oy --

In the Specification

Col. 2, line 2, delete "ethanolgen," and insert -- ethanologen, --, therefor.

Col. 3, line 19, delete "*Myceliophtora*" and insert -- *Myceliophthora* --, therefor.

Col. 3, line 21, delete "*anualata*" and insert -- *annulata* --, therefor.

Col. 3, line 21, delete "Malbrancheae cinnamonea." and insert -- *Malbranchea cinnamomea.* --, therefor.

Col. 3, line 66, delete "*Myceliophtora*" and insert -- *Myceliophthora* --, therefor.

Col. 4, line 6, delete "*Myceliophtora*" and insert -- *Myceliophthora* --, therefor.

Col. 5, line 32, delete "biofuel," and insert -- biofuel. --, therefor.

Col. 6, line 60, delete "*Mortiriella.*" and insert -- *Mortierella.* --, therefor.

Col. 7, line 19, delete "exo-galactoronase," and insert -- exo-galacturonase, --, therefor.

Col. 8, line 13, delete "At_ALKO4245Cel6A," and insert -- At_ALKO4245_Cel6A, --, therefor.

Col. 9, line 38, delete "Upsalalaan" and insert -- Uppsalalaan --, therefor.

Col. 10, line 48, delete "lyocel." and insert -- lyocell. --, therefor.

Col. 11, line 11, delete "dissaccharide" and insert -- disaccharide --, therefor.

Signed and Sealed this  
Twenty-fifth Day of March, 2014

Michelle K. Lee  
*Deputy Director of the United States Patent and Trademark Office*

CERTIFICATE OF CORRECTION (continued)

U.S. Pat. No. 8,580,552 B2

Col. 12, line 38, delete "dinitrosalisylic" and insert -- dinitrosalicylic --, therefor.

Col. 13, lines 30-31, delete "(http://expasy" and insert -- (expasy --, therefor.

Col. 13, line 44, delete "(http://expasy" and insert -- (expasy --, therefor.

Col. 15, line 56, delete "*Magnaporthea*," and insert -- *Magnaporthe*, --, therefor.

Col. 17, line 11, delete "and to" and insert -- and --, therefor.

Col. 19, line 4, delete "exo-galactoronase," and insert -- exo-galacturonase, --, therefor.

Col. 20, line 7, delete "exo-galactoronases," and insert -- exo-galacturonases, --, therefor.

Col. 23, line 44, delete "*Mortiriella*," and insert -- *Mortierella*, --, therefor.

Col. 23, lines 51-52, delete "(http://www" and insert -- (www --, therefor.

Col. 25, line 16, delete "1830 by" and insert -- 1830 bp --, therefor.

Col. 28, line 54, delete "*sublitis*" and insert -- *subtilis* --, therefor.

Col. 28, line 62, delete "on a to" and insert -- on a --, therefor.

Col. 29, line 46, delete "*Mortiriella*," and insert -- *Mortierella*, --, therefor.

Col. 29, line 57, delete "*Mortiriella alpinis*" and insert -- *Mortierella alpina* --, therefor.

Col. 30, lines 55-56, delete "exo-galactoronase," and insert -- exo-galacturonase, --, therefor.

Col. 32, line 4, delete "or to" and insert -- or --, therefor.

Col. 34, line 27, delete "pCe4Blunt-TOPO®" and insert -- pCR®4Blunt-TOPO® --, therefor.

Col. 35, line 37, delete "*thermohilum*" and insert -- *thermophilum* --, therefor.

Col. 35, line 50, delete "dioxigenin-labeled" and insert -- digoxigenin-labeled --, therefor.

Col. 35, lines 52-53, delete "dioxigenin-labeled" and insert -- digoxigenin-labeled --, therefor.

Col. 36, line 37, delete "*thermohilum*" and insert -- *thermophilum* --, therefor.

Col. 36, line 43, delete "*thermohilum*" and insert -- *thermophilum* --, therefor.

Col. 40, last but one sentence, delete "Correspondigly," and insert -- Correspondingly, --, therefor.

Col. 40, last sentence, delete "cbhl" and insert -- *cbh1* --, therefor.

Col. 41, line 44, delete "650" and insert -- 650 μl. --, therefor.

Col. 42, line 48, delete "*Nonomurea*" and insert -- *Nonomuraea* --, therefor.

Col. 44, line 24, delete "*Nonomurea*" and insert -- *Nonomuraea* --, therefor.

Col. 44, line 60, delete "http://www" and insert -- www --, therefor.

Col. 46, line 18, delete "organosols-pretreated" and insert -- organosolv-pretreated --, therefor.

Col. 46, line 37, delete "dinitrosalisylic" and insert -- dinitrosalicylic --, therefor.

Col. 46, line 47, delete "eykaryotic" and insert -- eukaryotic --, therefor.

Col. 46, line 60, delete "Rano," and insert -- Råttö, --, therefor.

In the Claims

Col. 69, line 50, in Claim 3, delete "The isolated" and insert -- The --, therefor.

Col. 69, line 53, in Claim 4, delete "The isolated" and insert -- The --, therefor.

Col. 69, line 65, in Claim 6, delete "pALK2582." and insert -- pALK2582, --, therefor.

Col. 70, line 41, in Claim 7, delete "claim 10," and insert -- claim 1, --, therefor.

Col. 70, lines 62-63, in Claim 13, delete "exo-α-L-arabinascs," and insert -- exo-α-L-arabinases, --, therefor.

Col. 70, line 63, in Claim 13, delete "exo-galactoronase," and insert -- exo-galacturonase, --, therefor.

Col. 71, line 55, in Claim 33, delete "26" and insert -- claim 26, --, therefor.

Col. 71, line 61, in Claim 35, delete "claim 22." and insert -- claim 33. --, therefor.

Col. 72, line 5, in Claim 36, delete "lo amino" and insert -- to amino --, therefor.

Col. 72, line 5, in Claim 36, delete "SEP ID" and insert -- SEQ ID --, therefor.

Col. 72, lines 27-28, in Claim 39, delete "cellobionhydrolase," and insert -- cellobiohydrolase, --, therefor.

Col. 72, line 33, in Claim 39, delete "exo-galactoronase," and insert -- exo-galacturonase, --, therefor.

Col. 72, line 36, in Claim 39, delete "peroxidase. $H_2O_2$-" and insert -- peroxidase, $H_2O_2$- --, therefor.

Col. 72, line 39, in Claim 40, delete "arc" and insert -- are --, therefor.

Col. 72, line 40, in Claim 40, delete "cither" and insert -- either --, therefor.

Col. 72, line 42, in Claim 41, delete "lo claim" and insert -- to claim --, therefor.

CERTIFICATE OF CORRECTION (continued)
U.S. Pat. No. 8,580,552 B2

Col. 72, line 53, in Claim 42, delete "ethanol." and insert -- ethanol, --, therefor.

Col. 72, line 59, in Claim 44, delete "claim 10" and insert -- claim 1 --, therefor.

Col. 72, line 61, in Claim 45, delete "biofuel." and insert -- biofuel, --, therefor.

Col. 72, line 63, in Claim 45, delete "claim 10" and insert -- claim 1 --, therefor.

Col. 73, line 8, in Claim 48, delete "method contacting" and insert -- method comprising contacting --, therefor.

Col. 73, line 17, in Claim 51, delete "biofuel." and insert -- biofuel, --, therefor.

```
                           SEQUENCE LISTING

<160> NUMBER OF SEQ ID NOS: 16

<210> SEQ ID NO 1
<211> LENGTH: 17
<212> TYPE: DNA
<213> ORGANISM: Artificial Sequence
<220> FEATURE:
<223> OTHER INFORMATION: Sequence of the oligonucleotide primer CBH_1S
<220> FEATURE:
<221> NAME/KEY: misc_feature
<222> LOCATION: (6)..(6)
<223> OTHER INFORMATION: N is A, G, T or C
<220> FEATURE:
<221> NAME/KEY: misc_feature
<222> LOCATION: (9)..(9)
<223> OTHER INFORMATION: R is A or G
<220> FEATURE:
<221> NAME/KEY: misc_feature
<222> LOCATION: (12)..(12)
<223> OTHER INFORMATION: Y is T or C
<220> FEATURE:
<221> NAME/KEY: misc_feature
<222> LOCATION: (15)..(15)
<223> OTHER INFORMATION: N is A, G, T or C

<400> SEQUENCE: 1
tggggncart gyggngg                                                    17

<210> SEQ ID NO 2
<211> LENGTH: 17
<212> TYPE: DNA
<213> ORGANISM: Artificial Sequence
<220> FEATURE:
<223> OTHER INFORMATION: Sequence of the oligonucleotide primer CBH_1AS
<220> FEATURE:
<221> NAME/KEY: misc_feature
<222> LOCATION: (3)..(3)
<223> OTHER INFORMATION: N is A, G, T or C
<220> FEATURE:
<221> NAME/KEY: misc_feature
<222> LOCATION: (9)..(9)
```

```
<223> OTHER INFORMATION: N is A, G, T or C
<220> FEATURE:
<221> NAME/KEY: misc_feature
<222> LOCATION: (12)..(12)
<223> OTHER INFORMATION: N is A, G, T or C
<220> FEATURE:
<221> NAME/KEY: misc_feature
<222> LOCATION: (14)..(14)
<223> OTHER INFORMATION: R is A or G

<400> SEQUENCE: 2
gcnggccanc cnarcca                                                     17

<210> SEQ ID NO 3
<211> LENGTH: 21
<212> TYPE: DNA
<213> ORGANISM: Artificial Sequence
<220> FEATURE:
<223> OTHER INFORMATION: Sequence of the oligonucleotide primer CBH_8

<400> SEQUENCE: 3
atggctaagc agctgctgct c                                                21

<210> SEQ ID NO 4
<211> LENGTH: 20
<212> TYPE: DNA
<213> ORGANISM: Artificial Sequence
<220> FEATURE:
<223> OTHER INFORMATION: Sequence of the oligonucleotide primer CBH_9
<220> FEATURE:
<221> NAME/KEY: misc_feature
<222> LOCATION: (6)..(6)
<223> OTHER INFORMATION: R is A or G

<400> SEQUENCE: 4
tcagarcgga gggttggcat                                                  20

<210> SEQ ID NO 5
<211> LENGTH: 44
<212> TYPE: DNA
<213> ORGANISM: Artificial Sequence
<220> FEATURE:
<223> OTHER INFORMATION: Sequence of the oligonucleotide primer Te_CBH_A

<400> SEQUENCE: 5
tattatccgc ggactgcgca tcatgcggaa tcttcttgct cttg                       44

<210> SEQ ID NO 6
<211> LENGTH: 38
<212> TYPE: DNA
<213> ORGANISM: Artificial Sequence
<220> FEATURE:
<223> OTHER INFORMATION: Sequence of the oligonucleotide primer Te_CBH_B

<400> SEQUENCE: 6
aatttggatc ctcagaacag cgggttagca ttcgtgag                              38

<210> SEQ ID NO 7
<211> LENGTH: 1014
<212> TYPE: DNA
<213> ORGANISM: Artificial Sequence
<220> FEATURE:
<223> OTHER INFORMATION: Sequence of the PCR fragment obtained from
      Acremonium thermophilum ALKO4245 (CBS 116240) using the primers
      CBH_1S and CBH_1AS

<400> SEQUENCE: 7
tggggacaat gcggcggcaa cggcttctcg ggaccgacct gttgcacgtc gggcaacacc      60
```

-continued

```
tgcgtcaagc tcaatgactg gtactccag tgcctgccca acagccaggt acgctgcgcc    120
cagccgctct agctggactt ctccttttac gagatgtctt ggctgacctc cttccaaagg    180
tgaccaccac cacaagctcg accaccacca ccaccaccac gaccctcac ggtcccacca     240 ccgccacaac caccaccacc aagccacctc ccaccaccac caccacgacc acgacgacga    300
agcctcctgg caccgcctcg ggcaccgtgt cctacaccgg caacccctc tctggcgtgc     360 agctttgggc caactcccac tacgcctccg agatctcggc ctccgccatc ccagcctga    420 cgggcgccat ggccaccaag gccgccgccg tcgccaaggt gcccagcttc agtggctgt     480 acgtctcctt tctcctctct ctccctcttc tctccttctc ttttttttcc ttttttgtgtg   540 tgtgtgtgtg tgttcacaca catcttaagc caagccactg acagttttct tccagtgaca    600
ccgcctccaa ggtctccctg atggccgaca ccctcagcga catccgccag gccaaccgcg    660
ccggcgccaa cccgccctac gccggccagt tcgttgtcta cgacctgccc gaccgcgact   720
gctccgccgc cgcctccaac ggcgagtaca gcatcgccga caacgcgtc gcccactaca    780 aggcctacat cgacagcatc cgcgagcagc tggtcgccta ctccgacgtg cgcgtcctgc    840
tcgtcgtcga gcccgactcg ctggccaacc tggtcaccaa cctcaacgtg gccaagtgct   900
ccaacgccca gagcgcctac ctcgagtgca ccaatacgcc ctcacccagc tcaacctgcc    960
caacgtcgcc atgtacctcg acgccggcca cgccggctgg ctcggctggc ctgc        1014
```

<210> SEQ ID NO 8
<211> LENGTH: 813
<212> TYPE: DNA
<213> ORGANISM: Artificial Sequence
<220> FEATURE:
<223> OTHER INFORMATION: Sequence of the PCR fragment obtained from
      Melanocarpus albomyces ALKO4237 (CBS 685.95) using the primers
      CBH_1S and CBH_1AS

<400> SEQUENCE: 8

```
tggggccaat gcggcggcaa tggctggacc gggccgacct gctgcgagtc gggcagcacg     60
tgcgtggccc agaacgacta ctactctgca gtgcctgccg gcggcgcgca ccaccacgtc    120
gggcccgggc acgccgtcca ccaccacgtc ggtgacgacc cccaccagcc agggctcgcc    180
cacgtcgccg ccgccgacga cgccgaccac gacgatcccc ggcggcgcgt cgacgacggc    240
cagctacacg ggcaacccgt cgcgggcat gcagatgtgg ccaacagct actacgcctc      300 cgaggtctcg tcgctggcca tccccagcat gacgggcccc atggccacca aggcggccga    360
ggtggccaag gtgcccagct tccagtggct cgaccgcaac gtgacggtcg acacgctctt    420
cacgcagacg ctggccgaga cccgggcggc caacgaggcg ggcgccaacc cgcccaacat    480
gggcatcttc gtcgtctatg acctgccgga ccgcgactgc gccgccgccg cgtccaacgg    540
cgagtgggcc atcgccgacg gcggcgtggc caactacaag gcctacatcg accgcatccg    600
caagcacatc atcgcctact cggacatccg catggccatc gtgctcgagc ccgactcgct    660
cgccaacatg gtgaccaaca tggacgtgcc caagtgcgcc aacgcggccg acacgtacaa    720
ggagctcacc atctacgccg tccagcagct cgacctgccc aacgtggcca tctacctgga    780
cgccggccac gccggctggc tcggctggcc agc                                 813
```

<210> SEQ ID NO 9
<211> LENGTH: 1757
<212> TYPE: DNA
<213> ORGANISM: Chaetomium thermophilum
<220> FEATURE:
<221> NAME/KEY: misc_feature
<223> OTHER INFORMATION: The nucleotide sequence of the Chaetomium thermophilum ALKO4265 (CBS 730.95) cbh2/cel6A gene

<400> SEQUENCE: 9

```
atggctaagc agctgctgct cactgccgct cttgcggcca cttcgctggc tgccctcta      60
cttgaggagc gccagagctg ctcctcggtc tggtatgtct caaccccgga tctgagtgtt    120
cgggatctgc ttgatcatgg atgccgatgc tgacatgttt gtgtttcagg ggtcaatgcg    180
gtggcatcaa ctacaacggc ccgacttgct gcccgtccgg cagtgtttgc acatacctga    240
atgactggta cagccagtgc attcccggcc aggctcagcc cggcacgact agcaccacgg    300
cccggaccac cagcaccagc accagcactt cgtccgtccg cccgaccacc acctccaata    360
cccctgtgac gactgctcct ccggcgacca ccatcccggg cggcgcctcg agcacggcca    420
gctacaacgg caaccccttc tcgggtgtcc agctctgggc caacacctac tactcgtccg    480
aggtgcacac tctggccatc cccagcctgt ctcctgagct ggctgccaag gccgccaagg    540
ttgctgaggt tcccagcttc cagtggctcg accgcaacgt gactgtcgac accctcttcg    600
tcggcacccct caatgacatt cgtggtgcca accagcgcgg tgccaacccg ccttatggta    660
agtgcaatgc ctgccccaca tcagacccta cgccccaagc ttggccactc tccagagtgg    720
agcagtgggt ccgacacaac cctaaccctg acaattccct tacctcaacc ccttttcaac    780
ctcgtccatc gcatcatcac aacctgtttt cttaacgtct atcatgatac tggtgctaaa    840
ctccgtaaag cggcccaatt tgtcgtttat gaccttccgg accgtgattg cgctgccgct    900
gcttcgaacg cgcagtgggc tatcgccaac aatggtgcca acaactacaa gcgttacatc    960
gaccggatcc gcgagatcct tatccagtac tctgatatcc gcactattct ggtcattgag   1020
cctgattccc tggccaacat ggtcaccaac atgaacgtcc agaagtgcgc gaacgccgca   1080
accacctaca aggagcttac catctatgcc ctcaagcagc tcaaccttcc tcatgtcgcc   1140
atgtacatgg atgctggtca cgccggctgg cttggctggc cgccaacat tcagcctgct   1200
gctgagctct ttggtcagct ctaccgtgac gctggcaagc ccgcttccgt ccgcggtctc   1260
gcggtaagaa agctcctgag acctcgactc ctggaacaac agttactgac ataacctaga   1320
ccaacgttgc caactacaat gcttggtcga tcgccagcgc tccgtcgtat acttctccta   1380
accctaacta cgacgagaag cactacattg aggcctttgc tcctcttctc cgcaaccagg   1440
gcttcgatgc caagttcatc gtcgacaccg gccgtaacgg caagcagccc accggccagc   1500
tccaatgggg cgattggtgc aatgtcaagg gaactggctt cggtgtgcgt cccacttcta   1560
acactgggca tgagcttgtt gatgctttcg tgtgggtcaa gccggtggt gagtccgacg   1620
gcaccagcga caccagcgct gctcgttacg actatcactg cggccttttcc gacgcattga   1680
ctccagcgcc tgaggctggc caatggttcc aggcttattt cgaacagctg ctcattaatg   1740
ccaaccctcc gttctga                                                  1757
```

<210> SEQ ID NO 10
<211> LENGTH: 1754
<212> TYPE: DNA
<213> ORGANISM: Talaromyces emersonii
<220> FEATURE:
<221> NAME/KEY: misc_feature
<223> OTHER INFORMATION: The nucleotide sequence of the Talaromyces
      emersonii DSM 2432 (RF8069) cbh2/cel6A gene

<400> SEQUENCE: 10

```
atgcggaatc ttcttgctct tgcaccggca gcgctgcttc tcggcgcagc ggacgcgcaa      60
caatccctct ggggacaatg tgagcagctc ctcgaacgtc tgtctgatga attggtctga    120
```

-continued

| | |
|---|---|
| cagcttcagg cggagggaat tcgtggactg gagcgacgga ttgtgctgca ggagcgacgt | 180 |
| gcagcaccat caattcttgt acgtctgttc tctactgctg tcgagctcag ctaactgcgt | 240 |
| agactacgca caatgcgtcc ctgcaacggc cactcctacc acgttgacga caacgacaaa | 300 |
| gccctcgtcg actgcgccaa cgacccctcc tccgacgtca gcgacgacca caggcactgg | 360 |
| atcggcgaca tcgccctcca tcaccgcgtc tgcgtccggc aacccgtttg tcggatacca | 420 |
| gctctacgcc aacccgtact atgcctctga ggtgattagc ctggccatcc cgtcgctaag | 480 |
| cagcgagctg gttcccaagg cgagcgaggt ggccaaggtg ccgtcttttg tctggctgtg | 540 |
| ggtgatattc caccctgttt gggacttgca gagactgata ttgtcacagc gatcaagcgg | 600 |
| ccaaagtgcc caacatgggc gagtatctga agacatcca gtcccagaat gcggccggcg | 660 |
| cagaccctcc gattgcaggc atcttcgtcg tttacgacct acctgaccgc gactgcgcgg | 720 |
| cggcagcgag caatggcgag ttctccatcg ccaacaacgg cgttgccctg tacaagcaat | 780 |
| acatcgactc gatccgcgag cagctgacga cgtattcgga tgtgcacacc atcctgatca | 840 |
| ttggttagta cgctagtgat atttatcaat ttttttttg tcaatactga ctgccgcaga | 900 |
| acccgacagc ctggccaacc tggtcaccaa cctgaacgtg gcgaaatgcg cgaatgccca | 960 |
| gggcgcctat ctcgaatgca tcaactacgc catcacgcag ctcaacctgc cgaatgtggc | 1020 |
| catgtatctt gatgctggtg agcttccctc acataccagg gaataaaaga cagaactgat | 1080 |
| tgtctttcag gacacgccgg atggctaggc tggtcagcaa acctccaacc cgctgcgcag | 1140 |
| ctgtttgcag aggtctacaa gaacgcctcg tcgccggcct cggtgcgcgg tctcgcgacc | 1200 |
| aacgtcgcca actacaacgc ctggacgatc agcccgtgcc cgtcgtacac gcagggcgac | 1260 |
| cccaactgcg acgaggagga ctatgtgaat gcccttgcgc cgctgcttca gagccagggg | 1320 |
| tttaatgcgt actttatcac tgatacatgt gagtctcacc acacccagac ctcgactgga | 1380 |
| cgtacccaaa tctgacctgt tctgcagccc gcaacggcgt ccaacccacc aagcagaacc | 1440 |
| aatgggcga ctggtgcaac gtcatcggca ccgggttcgg cgtccgcccg acgactgaca | 1500 |
| ctggcaaccc tctcgaggac gccttcgtct gggtcaagcc gggtggcgag agcgatggca | 1560 |
| catctaacac gacctctccg cgatacgact accactgcgg gctgagcgat gcgctgcagc | 1620 |
| cggctccgga ggcgggaact tggttccagg taagttgcaa gcagagatgt actgtacatt | 1680 |
| ggagcgtatg ctaattatgt gtgttacagg cgtactttga gcagctgctt acgaatgcta | 1740 |
| acccgctgtt ctga | 1754 |

<210> SEQ ID NO 11
<211> LENGTH: 1830
<212> TYPE: DNA
<213> ORGANISM: Acremonium thermophilum
<220> FEATURE:
<221> NAME/KEY: misc_feature
<223> OTHER INFORMATION: The nucleotide sequence of the Acremonium
      thermophilum ALKO4245 (CBS 116240) cbh2/cel6A gene

<400> SEQUENCE: 11

| | |
|---|---|
| atggctgcca gacgtctcct gctcgctgcc tccctgtcgg cagtggctct cgccgcgccc | 60 |
| gtggtcgaag agcgccagaa ctgcgcctct acctggtagg caccactccc cagctgtttt | 120 |
| ttctcatctc tgagccaaag caacggtctg actctcttcg cttcttccaa acaggagcca | 180 |
| atgcggcggc aacggcttct cgggaccgac ctgttgcacg tcgggcaaca cctgcgtcaa | 240 |
| gctcaatgac tggtactccc agtgcctgcc caacagccag gtacgctgcg cccagccgct | 300 |
| ctagctggac ttctcctttt acgagatgtc ttggctgacc tccttccaaa ggtgaccacc | 360 |

```
accacaagct cgaccaccac caccaccacc acgaccoctc acggtcccac caccaccaca    420
accaccacca ccaagccacc tcccaccacc accaccacga ccacgacgac gaagcctcct    480
ggcaccgcct cgggcaccgt gtcctacacc ggcaaccoct tctctggcgt gcagcttttgg   540 gccaactcct actacgcctc cgagatctcg gcctccgcca tccccagcct gacgggcgcc    600
atggccacca aggccgccgc cgtcgccaag gtgcccagct ccagtggct gtacgtctcc     660 tttctcctct ctctccctct tctctccttc tcttttttt cctttttgtg tgtgtgtgtg    720
tgtgttcaca cacatcttaa gccaagccac tgacagtttt cttccagtga caccgcctcc   780
aaggtctccc tgatggccga caccctcagc gacatccgcc aggccaaccg cgccggcgcc    840
aacccgccct acgccggcca gttcgttgtc tacgacctgc ccgaccgcga ctgctccgcc    900
gccgcctcca acggcgagta cagcatcgcc gacaacggcg tcgcccacta caaggcctac    960
atcgacagca tccgcgagca gctggtcgcc tactccgacg tgcgcgtcct gctcgtcgtc    1020
gagcccgact cgctggccaa cctggtcacc aacctcaacg tggccaagtg ctccaacgcc    1080
cagagcgcct acctcgagtg caccaactac gccctcaccc agctcaacct gcccaacgtc    1140
gccatgtacc tcgacgccgg ccacgccggc tggctgggct ggcccgccaa cctgcagccc    1200
gccgccaccc tgttcgccaa ggtctacaac gacgccaaca agcccgctgc cgtgcgcggc    1260
ctcgccacca acgtcgccaa ctacaacggc tggaacctga cctcgccgcc ctcgtacacc    1320
caaggtatgc ccttcacgta tccctcccc ttcataccga gcctcgcatg ggactttccg    1380
gcctctcttt tgtctccgcc cccactctcc gtatctccag ttgggaaagc aatactgata   1440
cctcgggcag gcaacaacaa ctacgacgag atccactacg tccaggccat cgccccctc    1500 ctcaagtctg ccggcttcga cgcccacttc atcaccgaca ccggccgcaa cggcaagcag    1560
cccaccggcc agcagcaatg gggcgactgg tgcaacgtca tcggcaccgg cttcggcgtg    1620
cgccccacca ccaacacggg ccttgagctc gaggacgcct tcgtctgggt gaagcccggc    1680
ggcgagtgcg acggcaccag cgacaccagc gccgcccgct acgactacca ctgcggtctg    1740
tccgatgccc tgcagcccgc gcccgaggcc ggcacctggt tcgaggccta tttcgagcag    1800
ctgctcacca acgccaaccc gtcgttctga                                     1830
```

<210> SEQ ID NO 12
<211> LENGTH: 478
<212> TYPE: PRT
<213> ORGANISM: Acremonium thermophilum
<220> FEATURE:
<221> NAME/KEY: misc_feature
<223> OTHER INFORMATION: The deduced amino acid sequence of the
      Acremonium thermophilum ALKO4245 (CBS 116240) CBHII/Cel6A

<400> SEQUENCE: 12

Met Ala Ala Arg Arg Leu Leu Leu Ala Ala Ser Leu Ser Ala Val Ala
1               5                   10                  15

Leu Ala Ala Pro Val Val Glu Glu Arg Gln Asn Cys Ala Ser Thr Trp
                20                  25                  30

Ser Gln Cys Gly Gly Asn Gly Phe Ser Gly Pro Thr Cys Cys Thr Ser
            35                  40                  45

Gly Asn Thr Cys Val Lys Leu Asn Asp Trp Tyr Ser Gln Cys Leu Pro
        50                  55                  60

Asn Ser Gln Val Thr Thr Thr Ser Ser Thr Thr Thr Thr Thr
65                  70                  75                  80

Thr Thr Pro His Gly Pro Thr Thr Thr Thr Thr Thr Lys Pro
                85                  90                  95

```
Pro Pro Thr Thr Thr Thr Thr Thr Thr Thr Lys Pro Pro Gly Thr
            100                 105                 110

Ala Ser Gly Thr Val Ser Tyr Thr Gly Asn Pro Phe Ser Gly Val Gln
        115                 120                 125

Leu Trp Ala Asn Ser Tyr Tyr Ala Ser Glu Ile Ser Ala Ser Ala Ile
130                 135                 140

Pro Ser Leu Thr Gly Ala Met Ala Thr Lys Ala Ala Val Ala Lys
145                 150                 155                 160

Val Pro Ser Phe Gln Trp Leu Asp Thr Ala Ser Lys Val Ser Leu Met
                165                 170                 175

Ala Asp Thr Leu Ser Asp Ile Arg Gln Ala Asn Arg Ala Gly Ala Asn
        180                 185                 190

Pro Pro Tyr Ala Gly Gln Phe Val Val Tyr Asp Leu Pro Asp Arg Asp
        195                 200                 205

Cys Ser Ala Ala Ala Ser Asn Gly Glu Tyr Ser Ile Ala Asp Asn Gly
    210                 215                 220

Val Ala His Tyr Lys Ala Tyr Ile Asp Ser Ile Arg Glu Gln Leu Val
225                 230                 235                 240

Ala Tyr Ser Asp Val Arg Val Leu Leu Val Val Glu Pro Asp Ser Leu
                245                 250                 255

Ala Asn Leu Val Thr Asn Leu Asn Val Ala Lys Cys Ser Asn Ala Gln
                260                 265                 270

Ser Ala Tyr Leu Glu Cys Thr Asn Tyr Ala Leu Thr Gln Leu Asn Leu
        275                 280                 285

Pro Asn Val Ala Met Tyr Leu Asp Ala Gly His Ala Gly Trp Leu Gly
290                 295                 300

Trp Pro Ala Asn Leu Gln Pro Ala Ala Thr Leu Phe Ala Lys Val Tyr
305                 310                 315                 320

Asn Asp Ala Asn Lys Pro Ala Ala Val Arg Gly Leu Ala Thr Asn Val
                325                 330                 335

Ala Asn Tyr Asn Gly Trp Asn Leu Thr Ser Pro Pro Ser Tyr Thr Gln
                340                 345                 350

Gly Asn Asn Asn Tyr Asp Glu Ile His Tyr Val Gln Ala Ile Ala Pro
        355                 360                 365

Leu Leu Lys Ser Ala Gly Phe Asp Ala His Phe Ile Thr Asp Thr Gly
370                 375                 380

Arg Asn Gly Lys Gln Pro Thr Gly Gln Gln Gln Trp Gly Asp Trp Cys
385                 390                 395                 400

Asn Val Ile Gly Thr Gly Phe Gly Val Arg Pro Thr Thr Asn Thr Gly
                405                 410                 415

Leu Glu Leu Glu Asp Ala Phe Val Trp Val Lys Pro Gly Gly Glu Cys
                420                 425                 430

Asp Gly Thr Ser Asp Thr Ser Ala Ala Arg Tyr Asp Tyr His Cys Gly
        435                 440                 445

Leu Ser Asp Ala Leu Gln Pro Ala Pro Glu Ala Gly Thr Trp Phe Glu
        450                 455                 460

Ala Tyr Phe Glu Gln Leu Leu Thr Asn Ala Asn Pro Ser Phe
465                 470                 475

<210> SEQ ID NO 13
<211> LENGTH: 1607
<212> TYPE: DNA
<213> ORGANISM: Melanocarpus albomyces
<220> FEATURE:
<221> NAME/KEY: misc_feature
<223> OTHER INFORMATION: The nucleotide sequence of the Melanocarpus
``` albomyces ALKO4237 (CBS 685.95) cbh2/cel6A gene

<400> SEQUENCE: 13

```
atggtcaaga aactcctgct caccaccgcc ctggcggccg cctcgctggc ggctcccgtc      60
atcgaggagc gccagagctg cgcctctctc tggtgagcga gcccgtccga gcccgtcccc     120
gtccatccga gtgtcgagtg tgactgacac gaacgggatt cgtcccgtcc cgtcccgttc     180
cacaggggcc aatgcggcgg caatggctgg accgggccga cctgctgcga gtcgggcagc     240
acgtgcgtgg cccagaacga ctactactcg cagtgcctgc cgggcggcgc gaccaccacg     300
tcgggcccgg gcacgccgtc caccaccacg tcggtgacga cctccaccag ccagggctcg     360
cccacgtcgc cgccgccgac gacgccgacc acgacgatcc ccggcggcgc gtcgacgacg     420
gccagctaca cgggcaaccc gttcgcgggc atgcagatgt gggccaacag ctactacgcc     480
tccgaggtct cgtcgctggc catccccagc atgacgggcc ccatggccac caaggcggcc     540
gaggtggcca aggtgcccag cttccagtgg ctcgaccgca acgtgacggt cgacacgctc     600
ttcacgcaga cgctggccga gatccgggcg ccaacgagg cgggcgccaa cccgcccaac     660
atgggcatct cgtcgtcta tgacctgccc gaccgcgact cgccgccgc cgcgtccaac     720
ggcgagtggg ccatcgccga cggcggcgtg gccaactaca aggcctacat cgaccgcatc     780
cgcgagcaca tcatcgccta ctcggacatc cgcatggcca tcgtgctcga gcccgactcg     840
ctcgccaaca tggtgaccaa catggacgtg cccaagtgcg ccaacgcggc cgacacgtac     900
aaggagctca ccatctacgc cgtccagcag ctcgacctgc ccaacgtggc catctacctg     960
gacgccggcc acgccggctg gctcggctgg cccgccaacc tgcagcccgc cgccgacctc    1020
ttcgccggca tctaccgcga cgccggccgc cccgcgccc tgcgcggcct cgccaccaac    1080
gtggccaact acaacgcctg gagcctgagc tcgccgcccc cgtacacgtc gcccaacccc    1140
aactacgacg agctgcgctt catccaggcc ttccgcccgc tcctcgaggc caacggctgg    1200
tccgcccagt tcatcaccga ccagggccgc tccggcaagc agccgactgg tacgtttcca    1260
ccgttttttt ttttcccttt cttttttgttc tttcttcgtc acggcaacgt ctggctgacc    1320
tttgtttgtg tgtgtctatt acaggccagg aggaatgggg ccactggtgc aaccaggtcg    1380
gcaccggctt cggcatgcgc ccgacggccg acacgggcta cgacttccag gacgccatcg    1440
tctgggtcaa gccggcggc gagagcgacg gcaccagcga cacctccgcc gagcgctacg    1500
accaccactg cggcctgtcc gacgccctca gcccgctccc ggaggccggc cagtggttcc    1560
aggcctactt tgagcagctg ctcgagaacg cgaacccgcc gttctaa                  1607
```

<210> SEQ ID NO 14
<211> LENGTH: 472
<212> TYPE: PRT
<213> ORGANISM: Melanocarpus albomyces
<220> FEATURE:
<221> NAME/KEY: misc_feature
<223> OTHER INFORMATION: The deduced amino acid sequence of the
      Melanocarpus albomyces ALKO4237 (CBS 685.95) CBHII/Cel6A

<400> SEQUENCE: 14

Met Val Lys Lys Leu Leu Leu Thr Thr Ala Leu Ala Ala Ala Ser Leu
1               5                   10                  15

Ala Ala Pro Val Ile Glu Glu Arg Gln Ser Cys Ala Ser Leu Trp Gly
            20                  25                  30

Gln Cys Gly Gly Asn Gly Trp Thr Gly Pro Thr Cys Cys Glu Ser Gly
        35                  40                  45

Ser Thr Cys Val Ala Gln Asn Asp Tyr Tyr Ser Gln Cys Leu Pro Gly

```
            50                  55                  60
Gly Ala Thr Thr Thr Ser Gly Pro Gly Thr Pro Ser Thr Thr Thr Ser
65                  70                  75                  80

Val Thr Thr Ser Thr Ser Gln Gly Ser Pro Thr Ser Pro Pro Pro Thr
                85                  90                  95

Thr Pro Thr Thr Thr Ile Pro Gly Gly Ala Ser Thr Thr Ala Ser Tyr
            100                 105                 110

Thr Gly Asn Pro Phe Ala Gly Met Gln Met Trp Ala Asn Ser Tyr Tyr
        115                 120                 125

Ala Ser Glu Val Ser Ser Leu Ala Ile Pro Ser Met Thr Gly Pro Met
130                 135                 140

Ala Thr Lys Ala Ala Glu Val Ala Lys Val Pro Ser Phe Gln Trp Leu
145                 150                 155                 160

Asp Arg Asn Val Thr Val Asp Thr Leu Phe Thr Gln Thr Leu Ala Glu
                165                 170                 175

Ile Arg Ala Ala Asn Glu Ala Gly Ala Asn Pro Pro Asn Met Gly Ile
            180                 185                 190

Phe Val Val Tyr Asp Leu Pro Asp Arg Asp Cys Ala Ala Ala Ala Ser
        195                 200                 205

Asn Gly Glu Trp Ala Ile Ala Asp Gly Gly Val Ala Asn Tyr Lys Ala
210                 215                 220

Tyr Ile Asp Arg Ile Arg Glu His Ile Ile Ala Tyr Ser Asp Ile Arg
225                 230                 235                 240

Met Ala Ile Val Leu Glu Pro Asp Ser Leu Ala Asn Met Val Thr Asn
                245                 250                 255

Met Asp Val Pro Lys Cys Ala Asn Ala Ala Asp Thr Tyr Lys Glu Leu
            260                 265                 270

Thr Ile Tyr Ala Val Gln Gln Leu Asp Leu Pro Asn Val Ala Ile Tyr
        275                 280                 285

Leu Asp Ala Gly His Ala Gly Trp Leu Gly Trp Pro Ala Asn Leu Gln
290                 295                 300

Pro Ala Ala Asp Leu Phe Ala Gly Ile Tyr Arg Asp Ala Gly Arg Pro
305                 310                 315                 320

Arg Ala Leu Arg Gly Leu Ala Thr Asn Val Ala Asn Tyr Asn Ala Trp
                325                 330                 335

Ser Leu Ser Ser Pro Pro Tyr Thr Ser Pro Asn Pro Asn Tyr Asp
            340                 345                 350

Glu Leu Arg Phe Ile Gln Ala Phe Arg Pro Leu Leu Glu Ala Asn Gly
        355                 360                 365

Trp Ser Ala Gln Phe Ile Thr Asp Gln Gly Arg Ser Gly Lys Gln Pro
370                 375                 380

Thr Gly Gln Glu Glu Trp Gly His Trp Cys Asn Gln Val Gly Thr Gly
385                 390                 395                 400

Phe Gly Met Arg Pro Thr Ala Asp Thr Gly Tyr Asp Phe Gln Asp Ala
                405                 410                 415

Ile Val Trp Val Lys Pro Gly Gly Glu Ser Asp Gly Thr Ser Asp Thr
            420                 425                 430

Ser Ala Glu Arg Tyr Asp His His Cys Gly Leu Ser Asp Ala Leu Lys
        435                 440                 445

Pro Ala Pro Glu Ala Gly Gln Trp Phe Gln Ala Tyr Phe Glu Gln Leu
450                 455                 460

Leu Glu Asn Ala Asn Pro Pro Phe
465                 470
```

```
<210> SEQ ID NO 15
<211> LENGTH: 475
<212> TYPE: PRT
<213> ORGANISM: Chaetomium thermophilum
<220> FEATURE:
<221> NAME/KEY: misc_feature
<223> OTHER INFORMATION: The deduced amino acid sequence of the
      Chaetomium thermophilum ALKO4265 (CBS 730.95) CBHII/Cel6A

<400> SEQUENCE: 15

Met Ala Lys Gln Leu Leu Thr Ala Ala Leu Ala Ala Thr Ser Leu
1               5                   10                  15

Ala Ala Pro Leu Leu Glu Glu Arg Gln Ser Cys Ser Ser Val Trp Gly
            20                  25                  30

Gln Cys Gly Gly Ile Asn Tyr Asn Gly Pro Thr Cys Cys Pro Ser Gly
        35                  40                  45

Ser Val Cys Thr Tyr Leu Asn Asp Trp Tyr Ser Gln Cys Ile Pro Gly
    50                  55                  60

Gln Ala Gln Pro Gly Thr Ser Thr Thr Ala Arg Thr Thr Ser Thr
65                  70                  75                  80

Ser Thr Ser Thr Ser Ser Val Arg Pro Thr Thr Thr Ser Asn Thr Pro
                85                  90                  95

Val Thr Thr Ala Pro Pro Ala Thr Thr Ile Pro Gly Gly Ala Ser Ser
            100                 105                 110

Thr Ala Ser Tyr Asn Gly Asn Pro Phe Ser Gly Val Gln Leu Trp Ala
        115                 120                 125

Asn Thr Tyr Tyr Ser Ser Glu Val His Thr Leu Ala Ile Pro Ser Leu
    130                 135                 140

Ser Pro Glu Leu Ala Ala Lys Ala Ala Lys Val Ala Glu Val Pro Ser
145                 150                 155                 160

Phe Gln Trp Leu Asp Arg Asn Val Thr Val Asp Thr Leu Phe Val Gly
                165                 170                 175

Thr Leu Asn Asp Ile Arg Gly Ala Asn Gln Arg Gly Ala Asn Pro Pro
            180                 185                 190

Tyr Ala Gln Phe Val Val Tyr Asp Leu Pro Asp Arg Asp Cys Ala Ala
        195                 200                 205

Ala Ala Ser Asn Gly Glu Trp Ala Ile Ala Asn Asn Gly Ala Asn Asn
    210                 215                 220

Tyr Lys Arg Tyr Ile Asp Arg Ile Arg Glu Ile Leu Ile Gln Tyr Ser
225                 230                 235                 240

Asp Ile Arg Thr Ile Leu Val Ile Glu Pro Asp Ser Leu Ala Asn Met
                245                 250                 255

Val Thr Asn Met Asn Val Gln Lys Cys Ala Asn Ala Ala Thr Thr Tyr
            260                 265                 270

Lys Glu Leu Thr Ile Tyr Ala Leu Lys Gln Leu Asn Leu Pro His Val
        275                 280                 285

Ala Met Tyr Met Asp Ala Gly His Ala Gly Trp Leu Gly Trp Pro Ala
    290                 295                 300

Asn Ile Gln Pro Ala Ala Glu Leu Phe Gly Gln Leu Tyr Arg Asp Ala
305                 310                 315                 320

Gly Lys Pro Ala Ser Val Arg Gly Leu Ala Thr Asn Val Ala Asn Tyr
                325                 330                 335

Asn Ala Trp Ser Ile Ala Ser Ala Pro Ser Tyr Thr Ser Pro Asn Pro
            340                 345                 350

Asn Tyr Asp Glu Lys His Tyr Ile Glu Ala Phe Ala Pro Leu Leu Arg
        355                 360                 365
```

```
Asn Gln Gly Phe Asp Ala Lys Phe Ile Val Asp Thr Gly Arg Asn Gly
    370                 375                 380

Lys Gln Pro Thr Gly Gln Leu Gln Trp Gly Asp Trp Cys Asn Val Lys
385                 390                 395                 400

Gly Thr Gly Phe Gly Val Arg Pro Thr Ser Asn Thr Gly His Glu Leu
                405                 410                 415

Val Asp Ala Phe Val Trp Val Lys Pro Gly Gly Glu Ser Asp Gly Thr
                420                 425                 430

Ser Asp Thr Ser Ala Ala Arg Tyr Asp Tyr His Cys Gly Leu Ser Asp
            435                 440                 445

Ala Leu Thr Pro Ala Pro Glu Ala Gly Gln Trp Phe Gln Ala Tyr Phe
    450                 455                 460

Glu Gln Leu Leu Ile Asn Ala Asn Pro Pro Phe
465                 470                 475

<210> SEQ ID NO 16
<211> LENGTH: 459
<212> TYPE: PRT
<213> ORGANISM: Talaromyces emersonii
<220> FEATURE:
<221> NAME/KEY: misc_feature
<223> OTHER INFORMATION: The deduced amino acid sequence of the
      Talaromyces emersonii DSM 2432 (RF8069) CBHII/Cel6A

<400> SEQUENCE: 16

Met Arg Asn Leu Leu Ala Leu Ala Pro Ala Ala Leu Leu Leu Gly Ala
1               5                   10                  15

Ala Asp Ala Gln Gln Ser Leu Trp Gly Gln Cys Gly Gly Asn Ser Trp
            20                  25                  30

Thr Gly Ala Thr Asp Cys Ala Ala Gly Ala Thr Cys Ser Thr Ile Asn
        35                  40                  45

Ser Tyr Tyr Ala Gln Cys Val Pro Ala Thr Ala Thr Pro Thr Thr Leu
    50                  55                  60

Thr Thr Thr Thr Lys Pro Ser Ser Thr Ala Pro Thr Thr Pro Pro Pro
65                  70                  75                  80

Thr Ser Ala Thr Thr Thr Gly Thr Gly Ser Ala Thr Ser Pro Ser Ile
                85                  90                  95

Thr Ala Ser Ala Ser Gly Asn Pro Phe Val Gly Tyr Gln Leu Tyr Ala
            100                 105                 110

Asn Pro Tyr Tyr Ala Ser Glu Val Ile Ser Leu Ala Ile Pro Ser Leu
        115                 120                 125

Ser Ser Glu Leu Val Pro Lys Ala Ser Glu Val Ala Lys Val Pro Ser
    130                 135                 140

Phe Val Trp Leu Asp Gln Ala Ala Lys Val Pro Asn Met Gly Glu Tyr
145                 150                 155                 160

Leu Lys Asp Ile Gln Ser Gln Asn Ala Ala Gly Ala Asp Pro Pro Ile
                165                 170                 175

Ala Gly Ile Phe Val Val Tyr Asp Leu Pro Asp Arg Asp Cys Ala Ala
            180                 185                 190

Ala Ala Ser Asn Gly Glu Phe Ser Ile Ala Asn Asn Gly Val Ala Leu
        195                 200                 205

Tyr Lys Gln Tyr Ile Asp Ser Ile Arg Glu Gln Leu Thr Thr Tyr Ser
    210                 215                 220

Asp Val His Thr Ile Leu Ile Ile Glu Pro Asp Ser Leu Ala Asn Leu
225                 230                 235                 240

Val Thr Asn Leu Asn Val Ala Lys Cys Ala Asn Ala Gln Gly Ala Tyr
```

-continued

```
                  245                 250                 255
Leu Glu Cys Ile Asn Tyr Ala Ile Thr Gln Leu Asn Leu Pro Asn Val
            260                 265                 270

Ala Met Tyr Leu Asp Ala Gly His Ala Gly Trp Leu Gly Trp Ser Ala
            275                 280                 285

Asn Leu Gln Pro Ala Ala Gln Leu Phe Ala Glu Val Tyr Lys Asn Ala
            290                 295                 300

Ser Ser Pro Ala Ser Val Arg Gly Leu Ala Thr Asn Val Ala Asn Tyr
305                 310                 315                 320

Asn Ala Trp Thr Ile Ser Pro Cys Pro Ser Tyr Thr Gln Gly Asp Pro
                325                 330                 335

Asn Cys Asp Glu Glu Asp Tyr Val Asn Ala Leu Ala Pro Leu Leu Gln
            340                 345                 350

Ser Gln Gly Phe Asn Ala Tyr Phe Ile Thr Asp Thr Ser Arg Asn Gly
            355                 360                 365

Val Gln Pro Thr Lys Gln Asn Gln Trp Gly Asp Trp Cys Asn Val Ile
            370                 375                 380

Gly Thr Gly Phe Gly Val Arg Pro Thr Thr Asp Thr Gly Asn Pro Leu
385                 390                 395                 400

Glu Asp Ala Phe Val Trp Val Lys Pro Gly Gly Glu Ser Asp Gly Thr
                405                 410                 415

Ser Asn Thr Thr Ser Pro Arg Tyr Asp Tyr His Cys Gly Leu Ser Asp
            420                 425                 430

Ala Leu Gln Pro Ala Pro Glu Ala Gly Thr Trp Phe Gln Ala Tyr Phe
            435                 440                 445

Glu Gln Leu Leu Thr Asn Ala Asn Pro Leu Phe
    450                 455
```